(12) United States Patent
Gestwicki

(10) Patent No.: US 9,642,843 B2
(45) Date of Patent: May 9, 2017

(54) PHARMACEUTICAL COMPOUNDS AND USE OF SAME IN CANCER AND TAUOPATHIES

(71) Applicant: THE REGENTS OF THE UNIVERSITY OF MICHIGAN, Ann Arbor, MI (US)

(72) Inventor: Jason E. Gestwicki, Moss Beach, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/770,850

(22) PCT Filed: Feb. 27, 2014

(86) PCT No.: PCT/US2014/018843
§ 371 (c)(1),
(2) Date: Jan. 12, 2016

(87) PCT Pub. No.: WO2014/134243
PCT Pub. Date: Sep. 4, 2014

(65) Prior Publication Data
US 2016/0000770 A1   Jan. 7, 2016

Related U.S. Application Data

(60) Provisional application No. 61/769,942, filed on Feb. 27, 2013.

(51) Int. Cl.
| | | |
|---|---|---|
| *A61K 31/395* | (2006.01) |
| *A61K 31/428* | (2006.01) |
| *A61K 31/4439* | (2006.01) |
| *A61K 38/05* | (2006.01) |
| *C07D 277/64* | (2006.01) |
| *C07D 417/14* | (2006.01) |

(52) U.S. Cl.
CPC ........ *A61K 31/4439* (2013.01); *A61K 31/395* (2013.01); *A61K 31/428* (2013.01); *A61K 38/05* (2013.01); *C07D 277/64* (2013.01); *C07D 417/14* (2013.01)

(58) Field of Classification Search
None
See application file for complete search history.

(56) References Cited

U.S. PATENT DOCUMENTS 5,360,803 A * 11/1994 Shishido ................ A61K 31/42
514/224.2
2006/0252800 A1   11/2006 Ihara et al.

FOREIGN PATENT DOCUMENTS

JP    4090133 B2    5/2008

OTHER PUBLICATIONS

Davies et al., Formation of neuronal intranuclear inclusions underlies the neurological dysfunction in mice transgenic for the HD mutation, Cell, 90(3):537-48 (1997).
(Continued)

*Primary Examiner* — Timothy R Rozof
(74) *Attorney, Agent, or Firm* — Marshall, Gerstein & Borun LLP

(57) ABSTRACT

Disclosed are compounds of formula (1)-(V): where the substituents are as provided herein. Further disclosed are methods of inhibiting tau aggregation, treating or ameliorating a tauopathy or cancer by administration of such a compound. Tau is a microtubule-binding protein that accumulates in a number of neurodegenerative disorders, including frontotemporal dementia and Alzheimer's disease (AD). The presence of abnormal tau correlates with neuron loss and memory deficits in patients with AD and other neurodegenerative disorders that involve tau accumulation.

6 Claims, 10 Drawing Sheets

(56) References Cited

OTHER PUBLICATIONS

DiFiglia et al., Aggregation of huntingtin in neuronal intranuclear inclusions and dystrophic neurites in brain, Science, 277(5334):1990-3 (1997).
International Search Report and Written Opinion, International Application No. PCT/US2014/018843, mailed Jul. 28, 2014.
Jinwal et al., Chemical manipulation of hsp70 ATPase activity regulates tau stability, J. Neurosci., 29(39):12079-88 (2009).
Kaytor et al., Aberrant protein deposition and neurological disease, J. Biol. Chem., 274(53):37507-10 (1999).
Koide et al., Unstable expansion of CAG repeat in hereditary dentatorubral-pallidoluysian atrophy (DRPLA), Nat. Genet., 6(1):9-13 (1994).
Koren et al., Chaperone signalling complexes in Alzheimer's disease, J. Cell Mol. Med., 13(4):619-30 (2009).
La Spada et al., Androgen receptor gene mutations in X-linked spinal and bulbar muscular atrophy, Nature, 352(6330):77-9 (1991).
Mazanetz et al., Untangling tau hyperphosphorylation in drug design for neurodegenerative diseases, Nat. Rev. Drug Discov., 6(6):464-79 (2007).
Oddo et al., Blocking Abeta42 accumulation delays the onset and progression of tau pathology via the C terminus of heat shock protein70-interacting protein: a mechanistic link between Abeta and tau pathology, J. Neurosci., 28(47):12163-75 (2008).
PubChem Compound Summary for CID 10886458 (Oct. 26, 2006).
PubChem Compound Summary for CID 11758010 (Oct. 27, 2006).
Taniguchi et al., Inhibition of heparin-induced tau filament formation by phenothiazines, polyphenols, and porphyrins, J. Biol. Chem., 280(9):7614-23 (2005).
Trottier et al., Polyglutamine expansion as a pathological epitope in Huntington's disease and four dominant cerebellar ataxias, Nature, 378(6555):403-6 (1995).
Wischik et al., Selective inhibition of Alzheimer disease-like tau aggregation by phenothiazines, Proc. Natl. Acad. Sci. USA, 93(20):11213-8 (1996).

\* cited by examiner (A) Chemical structures of MKT-077 and YM-08

(B) Synthesis of MKT-077 and YM-08

(C) Synthesis of YM-08

(C) YM-08 retains anti-tau activity in HeLaC3 cells (D) Comparison of the biological activities of MKT-077, YM-08 and their analogs

| | anti-tau (HeLaC3 cells) | | | cancer cell viability (EC50 μM) | | |
|---|---|---|---|---|---|---|
| Compound | p-tau (%) | total tau (%) | EC$_{50}$ (μM) | MCF7 | MCF10A | MDA-MB-231 |
| MKT-077[a] | 81 | 80 | 8.0 ± 1.3 | 2.2 ± 0.2 | 3.0 ± 0.2 | 1.4 ± 0.3 |
| YM-01 | 88 | 89 | 3.2 ± 0.9 | 5.2 ± 0.8 | 3.3 ± 0.3 | 2.0 ± 0.2 |
| YM-08 | 42 | 64 | 15 ± 3.1 | 10.5 ± 1.9 | 7.8 ± 0.7 | 8.5 ± 1.4 |
| YM-02 | 12 | 21 | >30 | 5.8 ± 1.9 | 13.8 ± 2.2 | >30 |
| YM-03 | 39 | 40 | 22 ± 6.5 | >30 | >30 | >30 |
| YM-04 | 0 | 0 | >30 | >30 | >30 | >30 |
| YM-07 | 5 | 7 | >30 | 6.5 ± 2.9 | >30 | >30 |

[a]tau data from reference 23

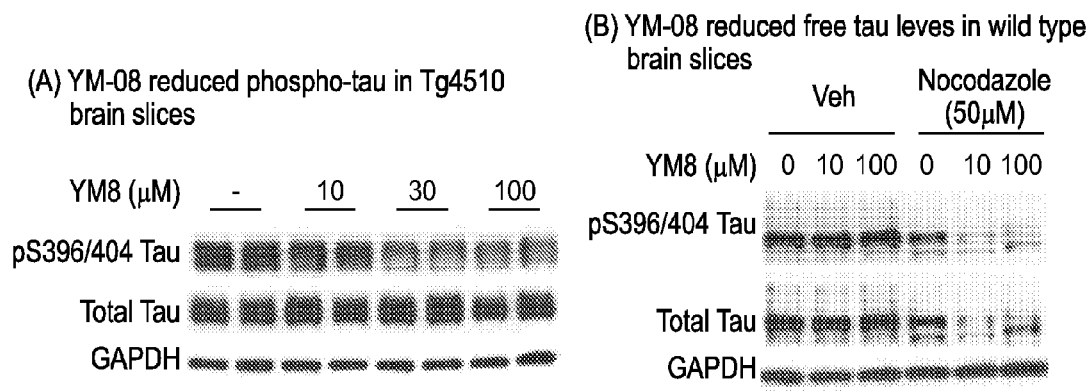
FIG. 5
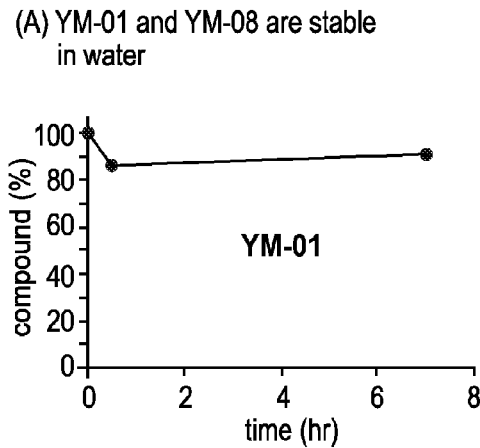
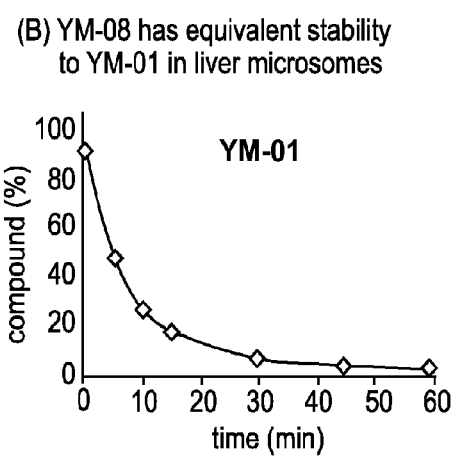
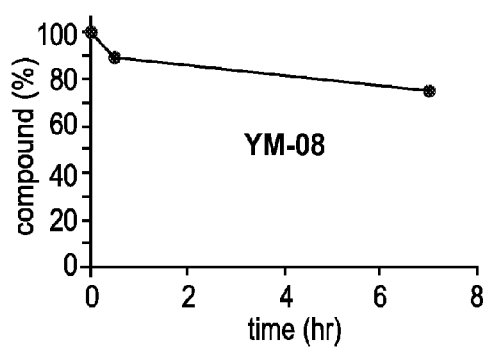
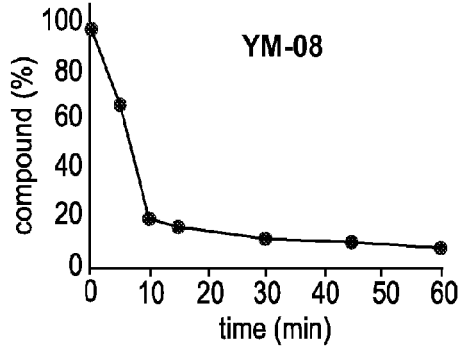
FIG. 6A
FIG. 6B (A) Initial pharmacokinetics of
    YM-01 and YM-08

YM-01 (20mg/kg ; i.v.)

| hour | plasma (ng/mL) | brain (ng/g) | kidney (ng/g) |
|---|---|---|---|
| 0.16 | 359 | 0 | 74378 |
| 1 | 324 | 0 | 63231 |

YM-08 (10mg/kg ; i.v.)

| hour | plasma (ng/mL) | brain (ng/g) | kidney (ng/g) |
|---|---|---|---|
| 0.16 | 1600 | 5743 | 7231 |
| 1 | 14.8 | n.a | 55.2 |

(B) YM-08 (6.6 mg/kg) is BBB permeable (C) YM-08 maintains B/P ~0.25 for 18 hrs

PHARMACEUTICAL COMPOUNDS AND USE OF SAME IN CANCER AND TAUOPATHIES

CROSS REFERENCE TO RELATED APPLICATIONS

The benefit of U.S. provisional application No. 61/769,942, filed Feb. 27, 2013, is claimed, the disclosure of which is incorporated by reference in its entirety.

STATEMENT OF GOVERNMENT INTEREST

This invention was made with government support under Grant Number NS059690, awarded by the National Institutes of Health. The government has certain rights in the invention.

BACKGROUND

Tau is a microtubule-binding protein that accumulates in a number of neurodegenerative disorders, including frontotemporal dementia and Alzheimer's disease (AD). The presence of abnormal tau correlates with neuron loss and memory deficits in patients with AD and other neurodegenerative disorders that involve tau accumulation. Therefore, selectively reducing tau levels or tau aggregation is an effective therapeutic strategy.

Efforts towards that goal have largely focused on either inhibitors of tau aggregation (see Taniguchi, et al. *J Biol Chem*, 280:7614 (2005), and Wischik, et al. *Proc Natl Acad Sci USA*, 93:11213 (1996)), inhibitors of tau phosphorylation (Mazanetz and Fischer, *Nat Rev Drug Discov*, 6:464 (2007)), or compounds that stimulate tau degradation (Koren, et al., *J Cell Mol Med*, 13:619 (2009); Jinwal, et al., *J Neurosci*, 29:12079 (2009); and Oddo, et al., *J Neurosci*, 28:12163 (2008)). Each of these strategies is potentially promising and well supported by genetic evidence, but many of the compounds identified to date have relatively modest activity. For example, methylene blue (MB), which both inhibits tau aggregation and stimulates tau degradation through heat shock protein 70 (Hsp70), has an $EC_{50}$ value of approximately 10 µM. Other promising compounds, such as the Hsp90 inhibitors 17-AAG and EC1012, reduce tau levels but they also produce a robust stress response, which is expected to diminish their long-term efficacy.

Neurodegenerative disorders are also associated with expansion of polyCAG tracts (Kaytor et al., *J Biol Chem*, 274:37507 (1999)). Huntington's disease and several other neurodegenerative disorders are characterized by expansion of a polyglutamine sequence (LaSpada et al., *Nature*, 352:77 (1991); Koide et al., *Nat. Genet.*, 6:9 (1994)). The expanded polyCAG tracts encode abnormally long polyglutamine sequences within specific proteins promoting their nuclear and/or cytoplasmic aggregation. The protein aggregation is believed to contribute to cellular toxicity including cell death or apoptosis (Trottier et al., *Nature*, 378:403 (1995); Davies et al., *Cell*, 90:537 (1997); and DiFiglia et al., *Science*, 277:1990 (1997)).

MKT-077 is a delocalized lipophilic cationic rhodacyanine (FIG. 1A) that selectively binds Hsp70 in cells, based on biochemical and genetic studies. Recent NMR studies have shown that MKT-077 binds to an allosteric pocket in the nucleotide-binding domain (NBD) of Hsc70, an abundant, cytoplasmic member of the Hsp70 family. This binding site is highly conserved and MKT-077 is active against other family members, such as mitochondrial and prokaryotic Hsp70s. Prior efforts have shown that MKT-077 and its analogs bind Hsp70 family members and have anti-cancer activity in multiple cancer lines, including melanoma cells and carcinomas of the colon, breast and pancreas. Based on these observations, MKT-077 advanced to a Phase I clinical study as an anti-cancer agent. However, progress was halted due to nephrotoxicity in a subset of patients. Renal damage was likely exacerbated by the dramatic accumulation of MKT-077 in the kidney, as shown by whole animal imaging and pharmacodynamic studies. Moreover, these same studies confirmed that MKT-077 does not cross the BBB, blunting any potential use in treating or studying neurodegenerative diseases. Together, these problems have limited use of MKT-077, especially in CNS disorders.

Thus, new compounds that have anti-cancer properties or can regulate tau and/or polyglutamine are of interest.

SUMMARY

Provided herein are compounds and compositions and their use in anticancer and tauopathy applications. More specifically, provided herein are compounds having a formulae of (I)-(V):

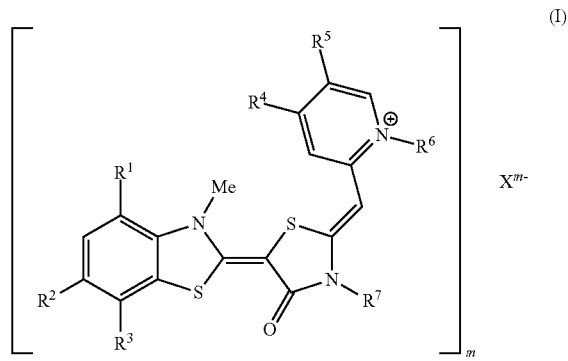

wherein $R^1$, $R^2$, and $R^3$ are each selected from the group consisting of hydrogen, fluoro, chloro, methoxy, methyl, or trifluoromethyl, $R^4$ and $R^5$ are each selected from hydrogen, fluoro, and chloro, $R^6$ is $C_1$-$C_4$ alkyl or $CH_2Ar$; Ar is aryl; $R^7$ is ethyl, allyl, or benzyl; X is a pharmaceutically acceptable anion, and m is 1, 2, or 3; with the proviso that (1) if $R^6$ is alkyl, $R^7$ is ethyl, and each of $R^4$ and $R^5$ is hydrogen, then at least one of $R^1$, $R^2$, and $R^3$ is other than hydrogen; and (2) when each of $R^1$, $R^2$, $R^3$, $R^4$, and $R^5$ is hydrogen, $R^6$ is $CH_2Ar$;

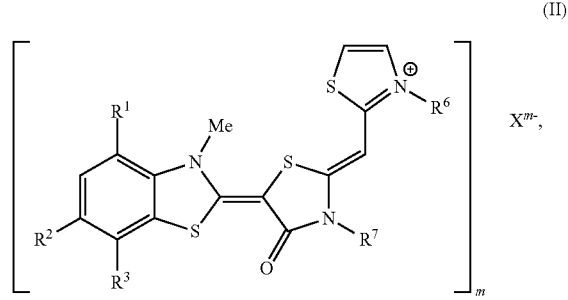

wherein $R^1$, $R^2$, and $R^3$ are each independently selected from the group consisting of hydrogen, chloro, fluoro, methoxy, and trifluoromethyl; $R^6$ is $CH_2Ar$ or allyl; Ar is aryl; $R^7$ is ethyl, allyl, or benzyl; and X is a pharmaceutically acceptable anion, and m is 1, 2, or 3;

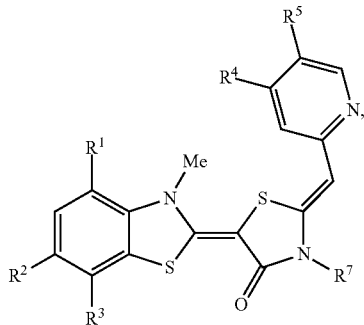
(III)

wherein $R^1$, $R^2$, and $R^3$ are each independently selected from the group consisting of hydrogen, chloro, fluoro, methoxy, and trifluoromethyl; $R^4$ and $R^5$ are each selected from the group consisting of hydrogen, fluoro, and chloro; $R^7$ is ethyl, allyl, or benzyl; with the proviso that when $R^7$ is ethyl, at least one of $R^4$ and $R^5$ is other than hydrogen, or a salt thereof;

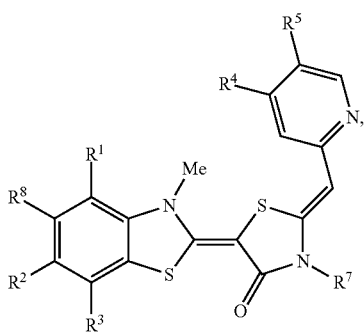
(IV)

wherein $R^1$, $R^2$, $R^3$, and $R^8$ are each selected from the group consisting of hydrogen, fluoro, chloro, methoxy, and trifluoromethyl; $R^4$ and $R^5$ are each selected from the group consisting of hydrogen, fluoro, chloro, methyl, and; $R^7$ is methyl, ethyl, or benzyl, or a salt thereof; and

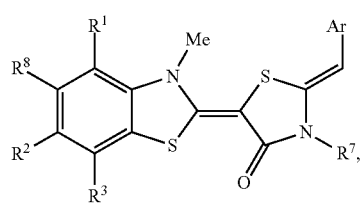
(V)

wherein Ar is pyridinyl, thiazolyl, pyrazinyl, or pyridinone; $R^1$, $R^2$, $R^3$, and $R^8$ are each selected from the group consisting of hydrogen, fluoro, chloro, methoxy, ethoxy, methyl, ethyl, propyl, isopropyl, trifluromethyl, $SO_2Me$, $NO_2$, trifluoromethoxy, CN, ethoxy, propoxy, and isopropoxy, with the proviso that at least one of $R^1$, $R^2$, $R^3$, and $R^8$ is not hydrogen; $R^7$ is selected from ethyl, allyl, benzyl, methoxy, ethoxy, and $(CH_2)_{1-3}CO_2R$, where R is a $C_{1-3}$alkyl, or a salt thereof. Also provided are compositions comprising a compound as disclosed herein and a pharmaceutically acceptable carrier.

Further provided are methods of using one of the compounds as disclosed herein by contacting it with a cell, and in some embodiments, administering it to a subject (e.g., a mammal, such as human). The cell can be a cancerous cell. The compound can be contacted (or administered) in an amount effective to inhibit, or decrease, heat shock protein 70 (HSP70) activity. The cancer can be a melanoma, hepatoma, glioma, neurobalstoma, sarcoma, carcinoma of the lung, carcinoma of the colon, carcinoma of the breast, carcinoma of the bladder, carcinoma of the ovary, carcinoma of the testes, carcinoma of the prostate, carcinoma of the cervix, carcinoma of the pancreas, carcinoma of the stomach, or carcinoma of the small intestine. In some cases, the cancer is breast cancer or myeloma. The methods disclosed herein can further comprise contacting (or administering) a second therapeutic. The second therapeutic can be a chemotherapeutic, an immunotherapeutic agent, an a HSP90 inhibitor, or a proteasome inhibitor. In some cases, the second therapeutic is a proteasome inhibitor or a HSP90 inhibitor. The second therapeutic and compound as disclosed herein can be administered simultaneously. In some cases, they are co-formulated. The second therapeutic and compound as disclosed herein can be administered sequentially. In some cases, the second therapeutic is administered before the compound, while in other cases, the second therapeutic is administered after the compound. In various cases, the second therapeutic is carfilzomib, 17-DMAG, NVP-AUY922, or bortezomib.

Further provided herein are methods of treating a subject suffering from cancer comprising administering to the subject a compound as disclosed herein in an amount effective to treat the cancer. The cancer can be a melanoma, hepatoma, glioma, neurobalstoma, sarcoma, carcinoma of the lung, carcinoma of the colon, carcinoma of the breast, carcinoma of the bladder, carcinoma of the ovary, carcinoma of the testes, carcinoma of the prostate, carcinoma of the cervix, carcinoma of the pancreas, carcinoma of the stomach, carcinoma of the small intestine, leukemia, lymphoma, myeloma, or a liquid tumor. In various cases, the cancer is breast cancer or myeloma.

Also provided herein are methods of inhibiting tau protein aggregate formation in a cell by contacting the cell with a compound as disclosed herein in an amount effective to inhibit the tau protein aggregate formation. In some cases, the method comprises inhibiting polyQ aggregate formation by contacting a cell with a compound as disclosed herein in an amount effective to inhibit the polyQ aggregate formation. In various embodiments, the contacting comprises administering the compound to a subject in need thereof. The subject can be a mammal, e.g., a human. The subject can suffer from a tauopathy. The tauopathy can be from Alzheimer's disease, Pick's disease, Progressive Supranuclear Palsy (PSP), fronto-temporal dementia (FTD), parkinsonism linked to chromosome 17 (FTDP-17), disinhibition-dementia-parkinsonism-amyotrophy complex (DDPAC), pallido-ponto-nigral degeneration (PPND), Guam-ALS syndrome, pallido-nigro-luysian degeneration (PNLD), Huntington's disease, Kennedy disease, dentatorubropallidoluysian atrophy, Spinocerebellar ataxia, Machado-Joseph disease, cortico-basal degeneration (CBD), amyotrophic lateral sclerosis (ALS), or a traumatic brain injury. In some embodiments, the method further comprises administering an anti-tau therapeutic agent. The anti-tau therapeutic agent can be of β-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of phosphodiesterase-4 (PDE-4), TNF-α inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin), methylene blue, an HSP90 inhibitor, celasterol, SAIK-MS, or a combination thereof.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Aspects of the invention described as methods of treatment should also be understood to include first or subsequent "medical use" aspects of the invention or "Swiss use" of compositions for the manufacture of a medicament for treatment of the same disease or condition.

Multiple embodiments are contemplated for combination inventions described herein. For example, some aspects of the invention that are described as a method of treatment (or medical use) combining two or more compounds or agents, whether administered separately (sequentially or simultaneously) or in combination (co-formulated or mixed). For each aspect described in this manner, the invention further includes a composition comprising the two or more compounds or agents co-formulated or in admixture with each other; and the invention further includes a kit or unit dose containing the two or more compounds/agents packaged together, but not in admixture. Optionally, such compositions, kits or doses further include one or more carriers in admixture with one or both agents or co-packaged for formulation prior to administration to a subject. The reverse also is true: some aspects of the invention are described herein as compositions useful for therapy and containing two or more therapeutic agents. Equivalent methods and uses are specifically contemplated.

Although the applicant(s) invented the full scope of the claims appended hereto, the claims appended hereto are not intended to encompass within their scope the prior art work of others. Therefore, in the event that statutory or judicially-recognized prior art within the scope of a claim is brought to the attention of the applicants by a Patent Office or other entity or individual, the applicant(s) reserve the right to exercise amendment rights under applicable patent laws to redefine the subject matter of such a claim to specifically exclude such prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE FIGURES

FIG. 5 shows that YM-08 reduces pathogenic tau levels in brain slices. (A) Brain slices from transgenic P301L tau mice (Tg4510) were treated for 6 hours with YM-08 and the levels of phospho- and total tau were measured. (B) Tau levels were unchanged in wild type brain slices treated with YM-08, but disruption of the microtubules with nocodozole promoted the ability of YM-08 to reduce total and phospho-tau levels.

μM) were relatively stable in water, as determined using LC-MS. (B) YM-01 and YM-08 were treated with human liver microsomes and (C) the major metabolites identified by LC-MS/MS. The $t_{1/2}$, values were both approximately 4 minutes and two major oxidation products were found.

Figure 7:
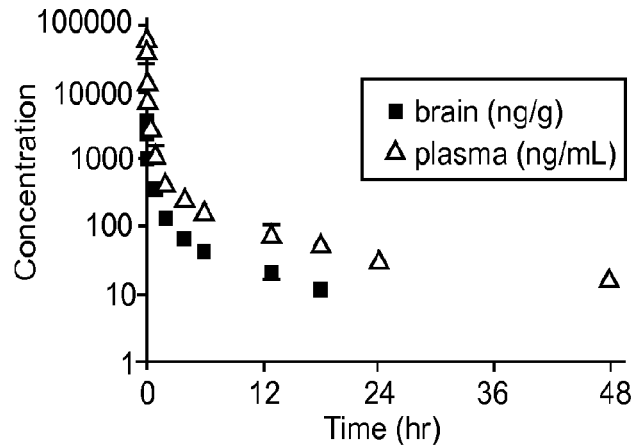
Figure 7:
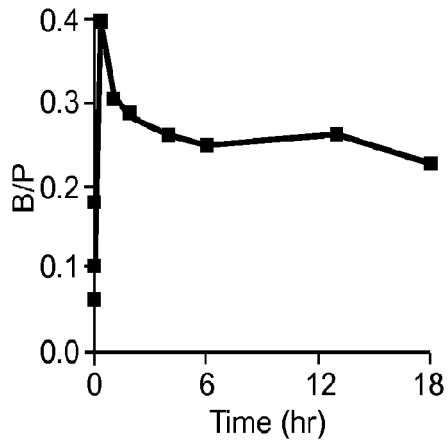

FIG. 7 shows the pharmacokinetics of YM-08 in CD1 mice. (A) Initial pharmacokinetics and biodistribution of YM-01 and YM-08. Compounds were suspended in buffered saline (YM-01) or 10% DMSO/saline (YM-08) and injected at 20 and 10 mg/kg, respectively. YM-08 was not soluble in saline or 10% DMSO/saline at 20 mg/kg. The levels of YM-08 in the brain at 1 hr after injection could not be accurately determined because its value was outside the calibration curve. (B) More detailed study of YM-08 in plasma and brain was performed after single (100 μL) i.v. injection (6.6 mg/kg) in 30% water; 5% Cremophor, 5% ethanol, 60% PBS. Results are average from data acquired from three female mice. (C) YM-08 maintains a B/P ratio of nearly 0.25 for 18 hrs.

Figure 8:
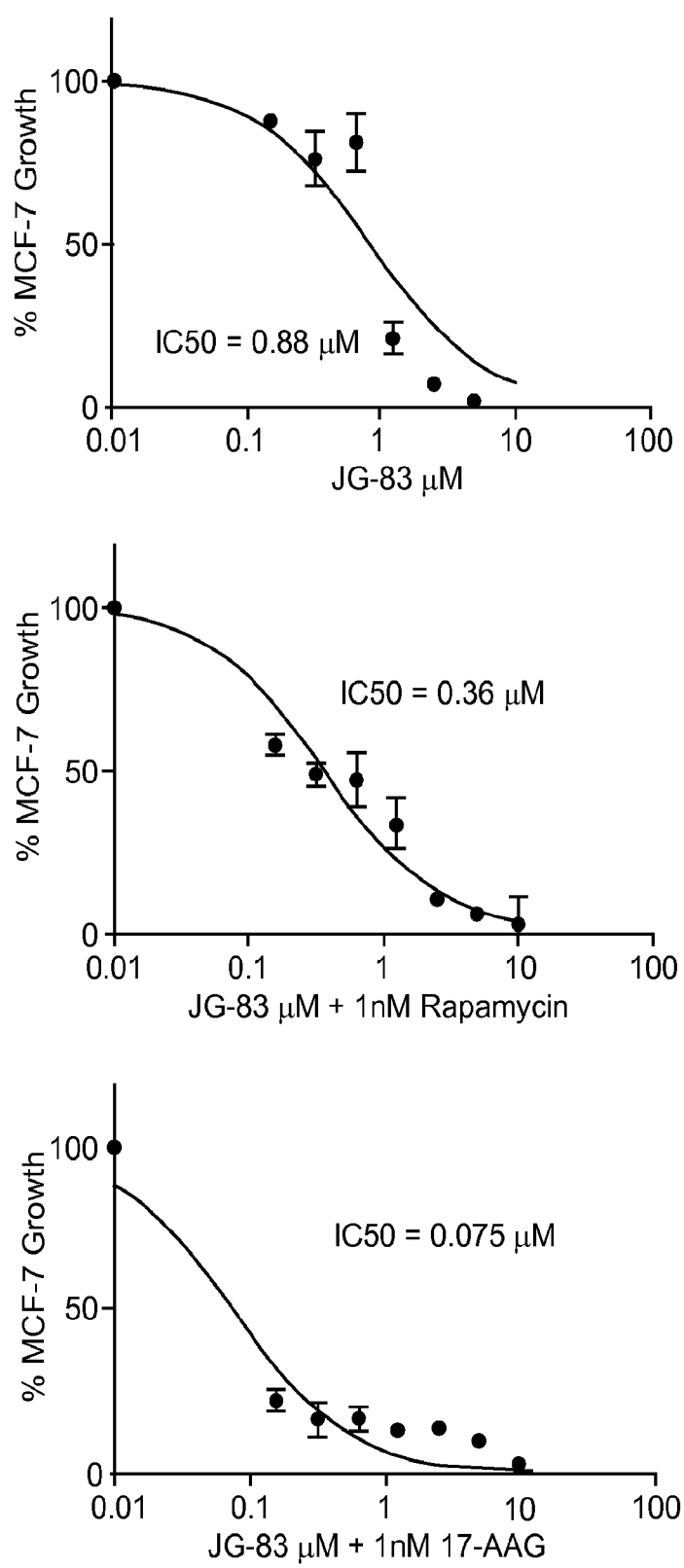

FIG. 8 shows the $IC_{50}$ data for inhibition of MCF-7 cancer cell growth, in the presence of JG-83 (top) or in the presence of JG-83 and the Hsp90 inhibitor 1 nM rapamycin (middle) or 1 nM 17-AAG (bottom).

Figure 9:
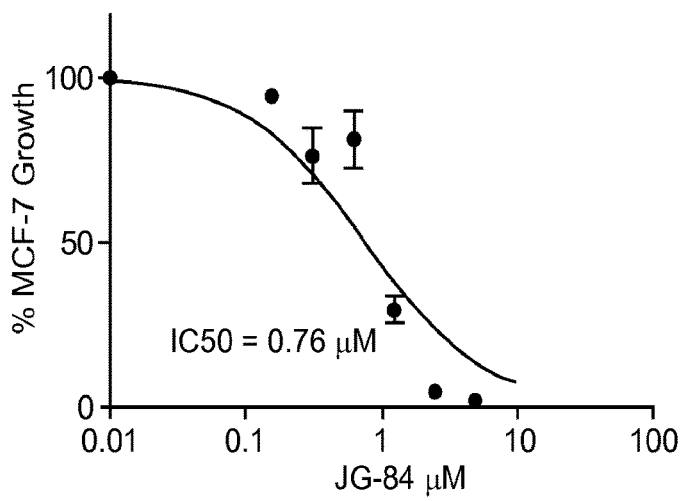
Figure 9:
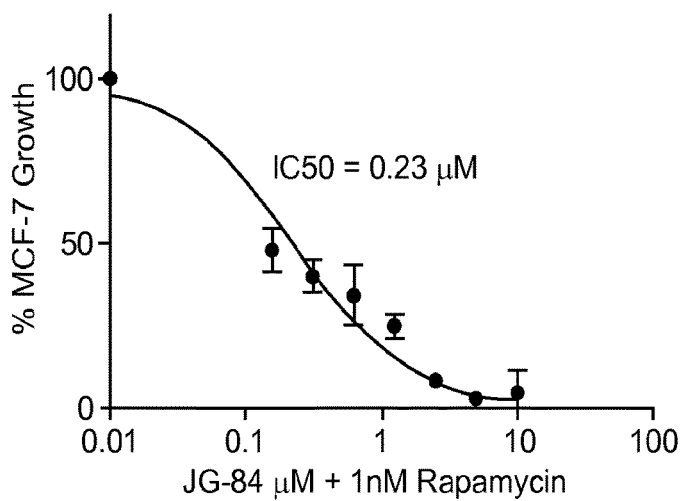
Figure 9:
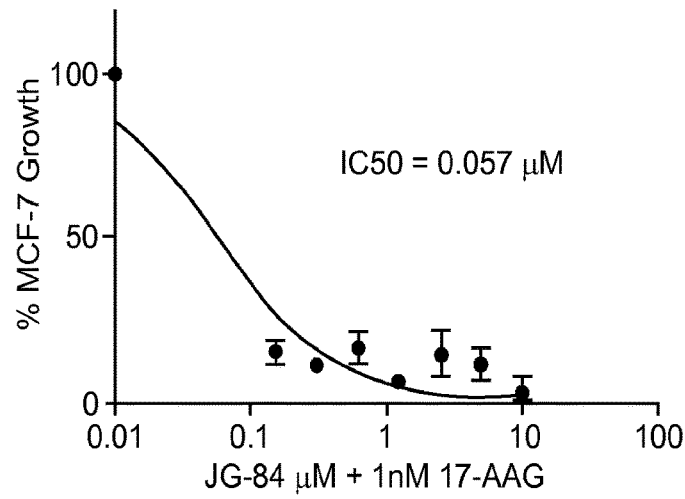

FIG. 9 shows the $IC_{50}$ data for inhibition of MCF-7 cancer cell growth, in the presence of JG-84 (top) or in the presence of JG-84 and the Hsp90 inhibitor 1 nM rapamycin (middle) or 1 nM 17-AAG (bottom).

DETAILED DESCRIPTION

Provided herein are compounds and their use in anti-cancer and/or anti-tau or polyQ applications.

In particular, provided herein are compounds having a structure of formula (I):

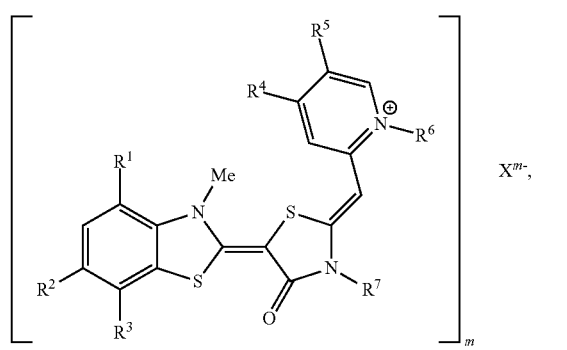

(I)

wherein $R^1$, $R^2$, and $R^3$ are each selected from the group consisting of hydrogen, fluoro, chloro, methoxy, methyl, or trifluoromethyl, $R^4$ and $R^5$ are each selected from hydrogen, fluoro, and chloro, $R^6$ is $C_1$-$C_4$ alkyl or $CH_2Ar$; Ar is aryl; $R^7$ is ethyl, allyl, or benzyl; X is a pharmaceutically acceptable anion, and m is 1, 2, or 3; with the proviso that (1) if $R^6$ is alkyl, $R^7$ is ethyl, and each of $R^4$ and $R^5$ is hydrogen, then at least one of $R^1$, $R^2$, and $R^3$ is other than hydrogen; and (2) when each of $R^1$, $R^2$, $R^3$, $R^4$, and $R^5$ is hydrogen, $R^6$ is $CH_2Ar$.

Further provided herein are compounds having a structure of formula (II):

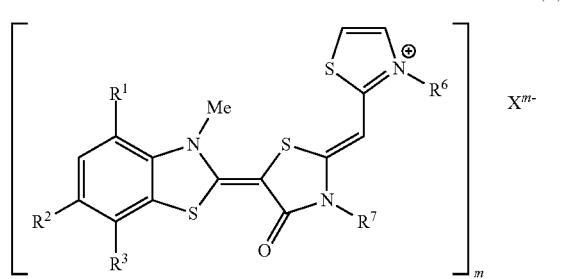

(II)

wherein $R^1$, $R^2$, and $R^3$ are each independently selected from the group consisting of hydrogen, chloro, fluoro, methoxy, and trifluoromethyl; $R^6$ is $CH_2Ar$ or allyl; $R^7$ is ethyl, allyl, or benzyl; and X is a pharmaceutically acceptable anion, and m is 1, 2, or 3.

Also provided are compounds having a structure of formula (III):

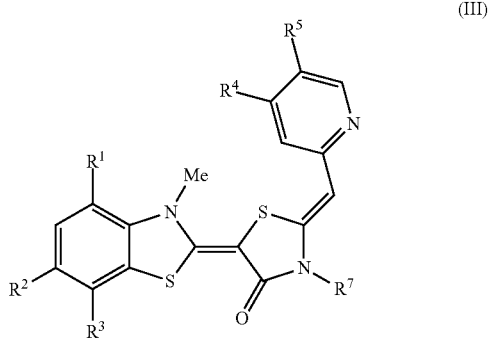

(III)

wherein $R^1$, $R^2$, and $R^3$ are each independently selected from the group consisting of hydrogen, chloro, fluoro, methoxy, and trifluoromethyl; $R^4$ and $R^5$ are each selected from the group consisting of hydrogen, fluoro, and chloro; $R^7$ is ethyl, allyl, or benzyl; with the proviso that when $R^7$ is ethyl, at least one of $R^4$ and $R^5$ is other than hydrogen, or a salt thereof.

Further provided herein are use of compound of formula (IV) in the preparation of medicaments or in methods of treatment applications:

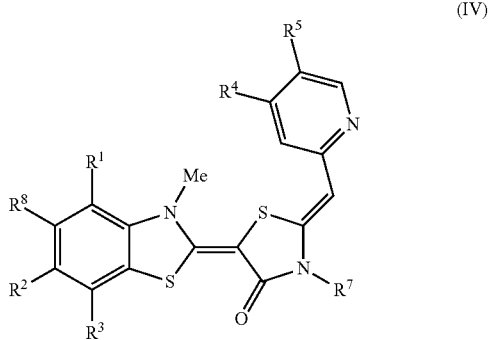

(IV)

wherein R¹, R², R³, and R⁸ are each selected from the group consisting of hydrogen, fluoro, chloro, methoxy, and trifluoromethyl; R⁴ and R⁵ are each selected from the group consisting of hydrogen, fluoro, chloro, methyl, and; R⁷ is methyl, ethyl, or benzyl, or a salt thereof.

Also provided are compounds and uses of compounds of formula (V):

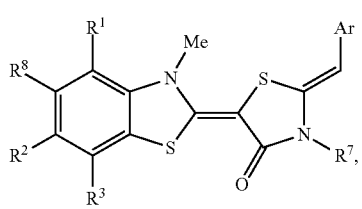

(V)

wherein Ar is pyridinyl, thiazolyl, or pyridinone; R¹, R², R³, and R⁸ are each selected from the group consisting of hydrogen, fluoro, bromo, chloro, methoxy, ethoxy, methyl, ethyl, propyl, isopropyl, trifluromethyl, $SO_2Me$, $NO_2$, $NH_2$, trifluoromethoxy, CN, ethoxy, propoxy, and isopropoxy, and in some cases with the proviso that at least one of R¹, R², R³, and R⁸ is not hydrogen and in some cases with the proviso that only one of R¹, R², R³, and R⁸ is not hydrogen; R⁷ is selected from ethyl, allyl, benzyl, methoxy, ethoxy, $C_{3-6}$cycloalkyl (e.g., cyclopropyl), and $(CH_2)_{1-3}CO_2R$, where R is a $C_{1-3}$alkyl, or a salt thereof. When Ar is pyridyl, the pyridine nitrogen can be ortho or para to the thiazone ring and the pyridine nitrogen can be substituted with an R⁶ substituent selected from $C_{1-6}$alkyl, $C_{1-6}$alkylenecycloalkyl, $C_{1-6}$alkylenearyl, and $C_{1-6}$alkyleneheteroaryl. When Ar is thiazolyl, the thiazolyl is attached at the 2-position on the thiazolyl, and in some cases the nitrogen of the thiazolyl can be substituted with a R⁶ substituent. In various cases, each of R¹, R², and R³ is hydrogen and R⁸ is selected from methyl, ethyl, fluoro, chloro, methoxy, ethoxy, nitro, trifluoromethyl, trifluoromethoxy, $SO_2Me$, and cyano. In various cases, R² and R³ are each fluoro, or one is hydrogen and the other fluoro. In various cases, each of R¹, R³, and R⁸ is hydrogen and R² is selected from $NH_2$, nitro, fluoro, chloro, trifluoromethyl, methoxy, ethoxy, methyl, ethyl, propyl, isopropyl, $SO_2Me$, and cyano. In various cases, each of R¹ and R³ is hydrogen and R² and R⁸ are each fluoro, or one is fluoro and the other hydrogen.

In some cases, the compound of formula (I), (II), or (V) is a salt and R⁶ is selected from Me, Et, $CH_2$pyridyl, propyl, $CH_2CH_2OH$, benzyl, $CH_2$-difluorophenyl, $CH_2$cyclopropyl, $CH_2$-(4-$CH_2NH(CO)Ot$-butyl)phenyl, $CH_2$-5-nitrofuranyl, $CH_2CH_2$-5-nitrofuranyl, $CH_2$-2-(5-$CF_3$)furanyl, $CH_2$-fluorophenyl, $CH_2$-chlorophenyl, $CH_2$-nitrophenyl, $CH_2$-cyanophenyl, $CH(Me)C(O)Ph$, $CH_2$-(methyl)phenyl, $CH_2$-trifluoromethylphenyl, $CH_2$-trifluoromethoxyphenyl, $CH_2$-difluoromethoxyphenyl, $CH_2$-3-(2-$CO_2Me$)thienyl, $CH_2$-3-(2-bromo)thienyl, $CH_2$-3-isoxazolyl, $CH_2$-5-isoxazolyl, $CH_2$-5-(3-phenyl)isoxazolyl, $CH_2$-3-(2-bromo)pyridyl, $CH_2$-3-thienyl, $CH_2$-2-(5-$CO_2Et$)furanyl, $CH_2$-4-(2-methyl)thiazolyl, $CH_2$-2-(5-$CO_2Me$)furanyl, $CH_2$-5-(3-methyl)isoxazolyl, and $CH_2$—$CH(Me)$phenyl. In some cases, the salt is a compound of formula (V). In various cases, the salt is a compound of formula (I). In various cases, the salt is a compound of formula (II). In various cases, R⁶ is a substituent on a pyridyl nitrogen. In various cases, R⁶ is a substituent on a thiazolyl nitrogen. In various cases, R⁶ is a substituent on a pyridonyl nitrogen.

In various embodiments, the compound of any one of formula (I)-(V) has a R⁷ selected from methyl, ethyl, methoxy, ethoxy, and —$(CH_2)_{1-3}CO_2R$, wherein R is methyl or ethyl. In some cases, R⁷ is ethyl. In various cases, R⁷ is $CH_2CO_2Me$. In various cases, R⁷ is methyl. In various cases, R⁷ is cyclopropyl.

One of the challenges facing clinical deployment of use an HSP70 inhibitor as a tauopathy therapeutic is that relatively few Hsp70 inhibitors are known and many of the first generation compounds, such as methylene blue (MB), are not selective for Hsp70. In fact, only a handful of known Hsp70 inhibitors, including 115-7c and MKT-077 are Hsp70-selective in cells and none of these compounds are known to pass the blood-brain barrier (BBB). A BBB penetrant Hsp70 inhibitor can be used to further probe the relationship between Hsp70 and tau homeostasis in vivo and that such a compound might serve as a lead for the development of anti-tau therapies.

The poor brain exposure of MKT-077 likely arises, in part, from its cationic pyridinium, which contributes to predicted physicochemical properties (clogP −0.9; tPSA 26.6) that are not typically associated with CNS penetration. Accordingly, replacing this group with a neutral pyridine improves BBB permeability. A resulting compound, YM-08 (FIG. 1A), is predicted to have more favorable clogP (3.8) and tPSA (35.9) values.

YM-08 retains affinity for Hsp70 in vitro and selectively reduced pathogenic tau in brain slices. In mice, YM-08 crossed the BBB and maintained a B/P greater than 0.25 for 18 hours. Moreover, YM-08 was quickly cleared from the kidney, perhaps reducing the opportunity for renal damage. Thus, YM-08 represents a suitable chemical scaffold for further development as a CNS-penetrant Hsp70 inhibitor.

Figure 2:
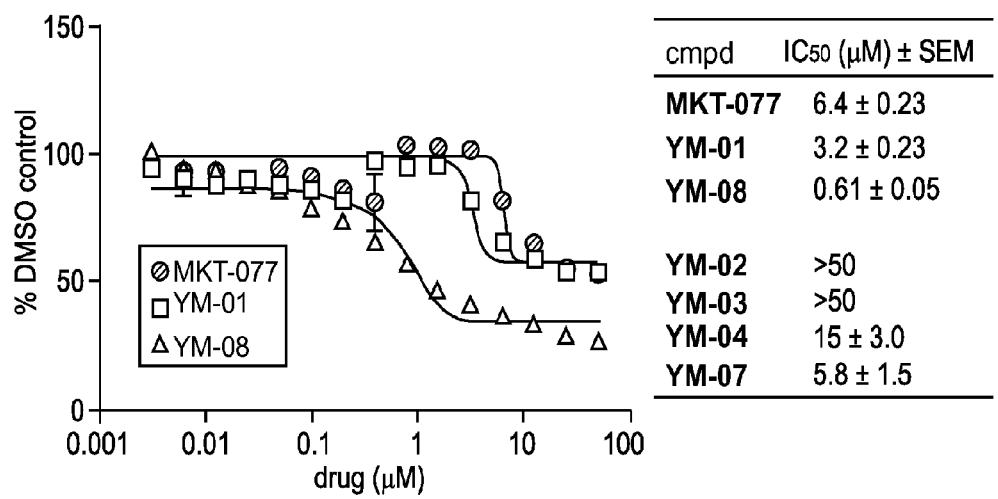
FIG. 2 shows that YM-08 binds to Hsp70. (A) Binding of a biotinylated MKT-077 to immobilized human Hsc70 was measured by ELISA. Results are the average of experiments performed in triplicate and error is SEM. (B) YM-08 binding to biotinylated $Hsc70_{NBD}$ was also measured by Octet Red. Fitting the binding curves gave a $K_D$ value of about 2.3 µM. Similar results were obtained using full length Hsp72 (HSPA1). Results are representative of experiments performed in triplicate.
Figure 2:
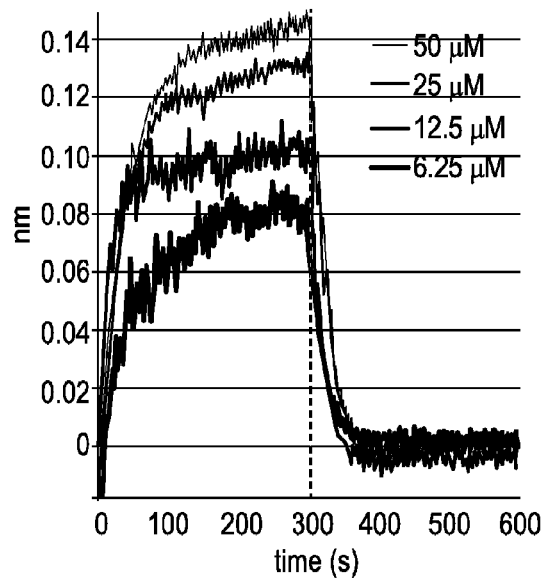

Binding of MKT-077 analogs to immobilized Hsp70 was evaluated using a competitive ELISA. In this established assay, a biotinylated version of MKT-077 is bound to immobilized human Hsc70 (HSPA8) and potential competitors are tested for their ability to block the interaction. It was first confirmed that both MKT-077 and YM-01 could inhibit binding, with inhibition constant ($IC_{50}$) values of 6.4±0.23 and 3.2±0.23 μM, respectively. Interestingly, YM-08 had an apparent $IC_{50}$ of 0.61±0.05 μM in the same assay, strongly suggesting that the charged pyridinium is not required for binding and that the pyridine may even be favored (FIG. 2A). As further controls, the truncated compounds YM-02, YM-03, YM-04 and YM-07 were tested. Removing the benzothiazole from YM-08 (compound YM-07) significantly weakened affinity ($IC_{50}$ about 5.8±1.5 μM; about 10-fold worse than YM-08), suggesting an important role for that group. Likewise, switching the pyridine of YM-07 to a cationic pyridinium (compound YM-04) further weakened affinity ($IC_{50}$ about 15±3 μM; about 2-fold worse than YM-07), re-enforcing the conclusion that the pyridine is preferred over the pyridinium. Finally, removing the ring altogether (compounds YM-02 and YM-03) abolished binding ($IC_{50}$>50 μM) (FIG. 2A). To confirm the binding of YM-08 in a separate experimental platform, its affinity for immobilized $Hsc70_{NBD}$ and Hsp72 (HSPA1) was directly measured by biolayer interferometry (BLI) and obtained $K_D$ values of about 4 and 2 μM, respectively (FIG. 2B). Together, these results show that YM-08 binds to Hsp70 and that both the benzothiazole and pyridine/pyridinium moieties are important for binding.

Figure 3:
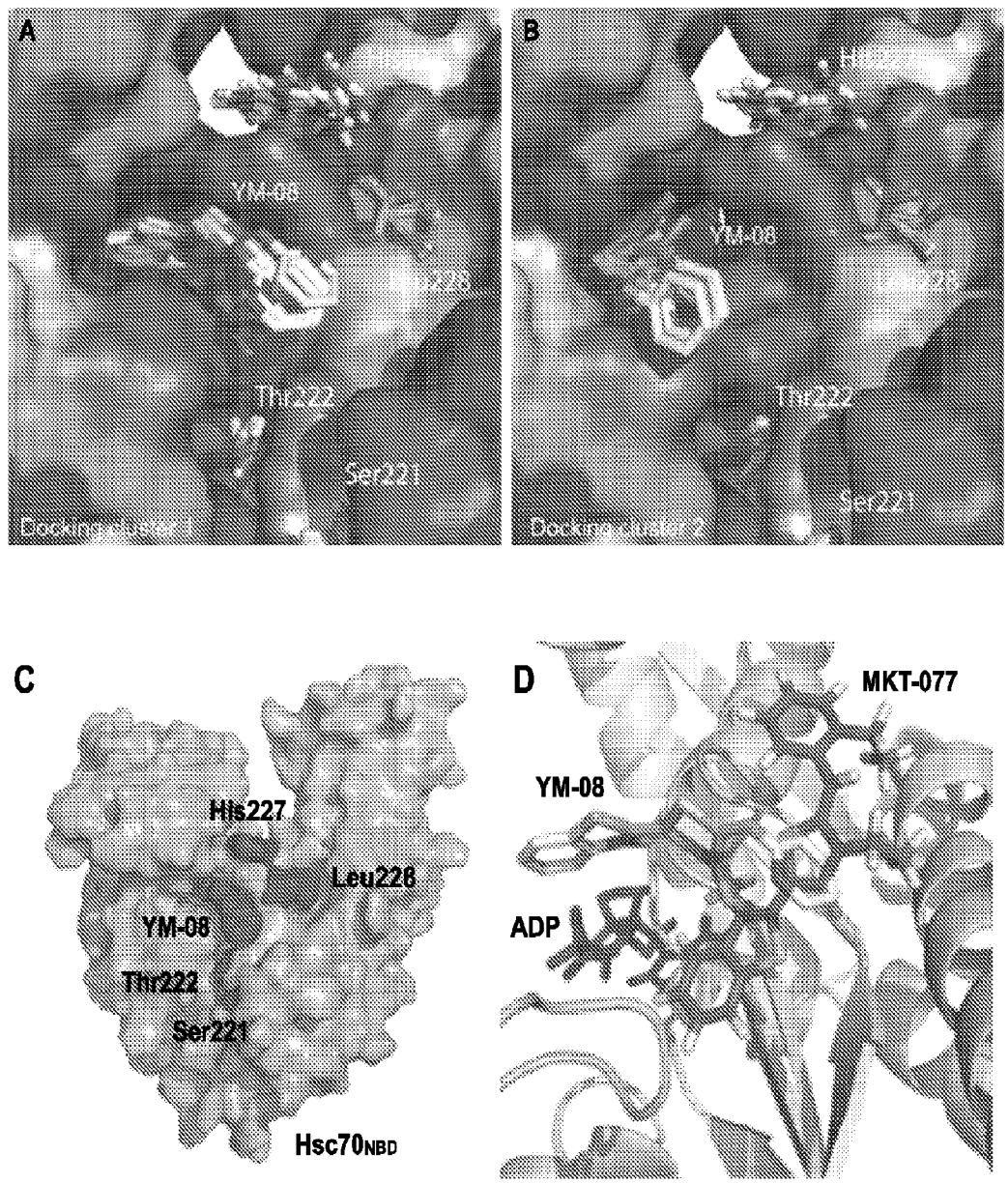
FIG. 3 shows docking of YM-08 to Hsc70. (A) Best cluster with an energy of −6.0 kcal/mol for its best binding member. The search box was restricted by the reported NMR shift perturbations from binding to MKT-077. (B) Second-best cluster with an energy of −5.6 kcal/mol for its best member. (C) Projected binding of YM-08 (best cluster) onto a surface representation of $Hsc70_{NBD}$. YM-08 is displayed as spheres. (D). MKT-077 and YM-08 are predicted to bind partially overlapping pockets in Hsc70. Figure panels were generated using PyMOL.

To further explore the interaction between YM-08 and Hsc70, docking simulations were performed in AUTODOCK 4.2 (see the Methods section). Specifically, YM-08 was docked to $Hsc70_{NBD}$ (PDB: 3C7N), revealing two best clusters (−6.0 and −5.6 kcal/mol, respectively) (FIGS. 3A and 3B) that were both predicted to position YM-08 in a cleft between subdomains IIA and IIB, adjacent to the nucleotide-binding site. This pocket is framed by a number of residues, including S208, S221, T222, D225, H227 and L228 (FIG. 3C) that are known to be sensitive to addition of MKT-077. When the side chains of these residues were allowed to freely rotate, they adjusted to define the YM08-binding pocket (see FIG. 3A). In this orientation, the benzothiazole of YM-08 was predicted to access a deep cleft composed of hydrophobic and cationic residues (T12, K70, R71, R75, V81, Y148, T203, G223 and T225). This orientation is slightly offset from that adopted by MKT-077 (FIG. 3D), indicating, as suggested by the competition binding studies (see FIG. 2A), the two molecules share a partially overlapping binding site.

Figure 4A:
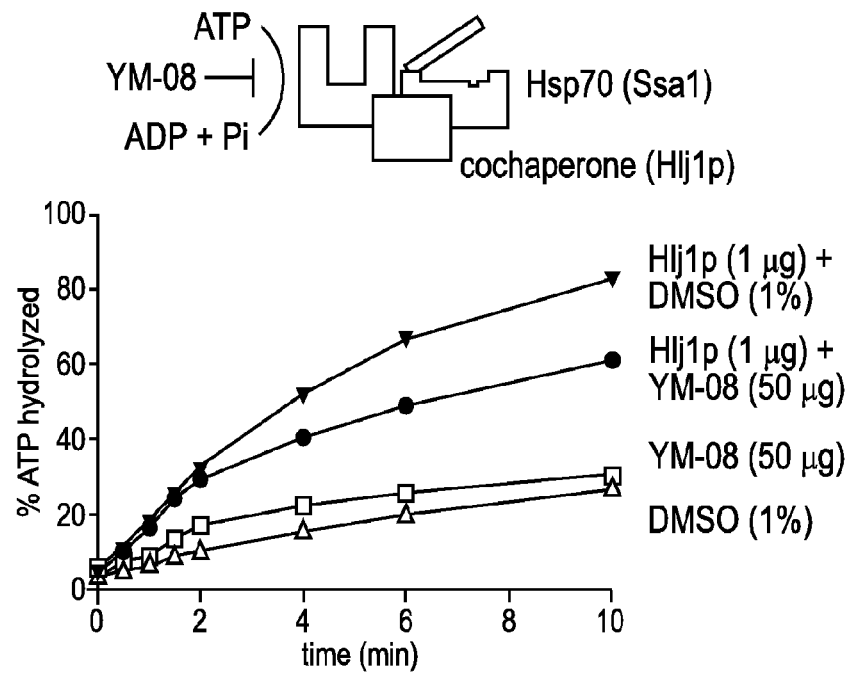
FIG. 4 shows that YM-08 retains anti-Hsp70 activities in vitro and in cells. (A) Single turnover ATPase assays were performed using purified yeast Ssa1p and Hlj1p. Results are the average of experiments performed in triplicate and error bars represent SEM. (B) Binding of DnaK to denatured luciferase (or human 4R0N tau) and the effects of MKT-077 analogs on the apparent affinity. Results are the average of triplicates and error is SEM. The dashed line is a DMSO control and the box is the error of the control. All compounds were tested at 50 µM. (C) Western blots of treated HeLaC3 cells, showing that YM-08 reduced phospho (p396/404) and total tau. Quantification of the results was performed in Image J and the results are shown. (D) Summary of the anti-tau and anti-cancer activity of MKT-077, YM-08 and their analogs. The error is SEM.
Figure 4B:
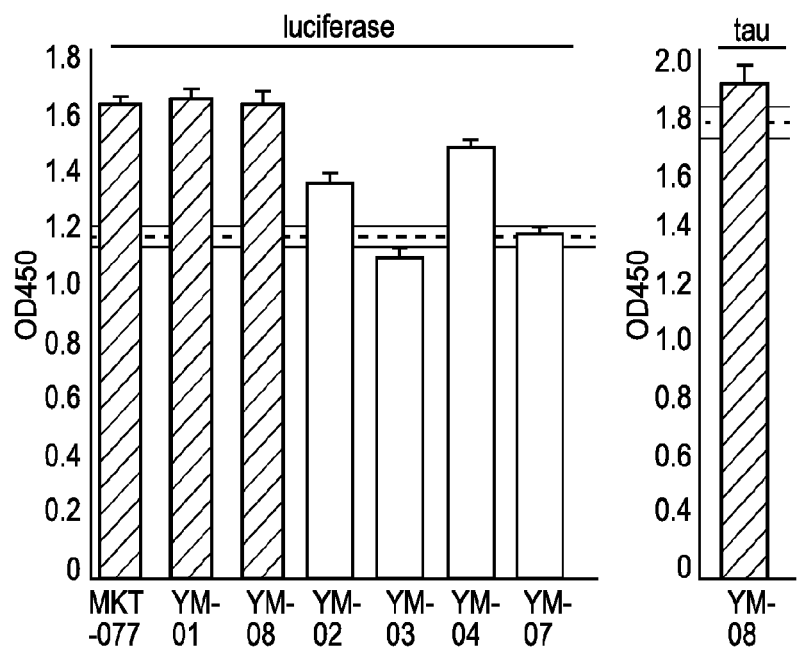

Next, the effect of chaperone functions by binding of YM-08 to Hsp70 was investigated. MKT-077 analogs have been reported to modestly inhibit ATP hydrolysis, using a model Hsp70 system that includes yeast Hsp70 (Ssa1) and the stimulatory co-chaperone, Hlj1. Using an identical assay system, it was found that YM-08 also partially inhibited ATP turnover (FIG. 4A). Interestingly, YM-08 only inhibited the Hlj1-stimulated ATPase activity, with minimal effect on the intrinsic ATPase activity of Ssa1 (FIG. 4A). This profile is shared with other allosteric Hsp70 inhibitors. As another test of chaperone function, the effects of the compounds on the binding of Hsp70 to a misfolded protein were measured. In previous work, MKT-077 stabilized the interaction between prokaryotic Hsp70 (DnaK) and denatured luciferase. Briefly, this assay involves immobilizing unfolded luciferase in microtiter plates and measuring binding to DnaK. Using this approach, the MKT-077 analogs were tested, and it was found that MKT-077, YM-01 and YM-08 (50 μM) all significantly enhance binding by about 30% (FIG. 4B). Conversely, the truncated molecules (YM-02, YM-03, YM-04 and YM-07) had reduced activity. To explore whether YM-08 might also enhance binding of Hsp70 to a more physiologically relevant substrate, binding of tau to immobilized human Hsc70 was measured. In this configuration, YM-08 also enhanced the affinity of chaperone for the protein substrate (FIG. 4B). Together, these studies show that YM-08 partially inhibits the enzymatic functions of Hsp70 family members and promotes tight binding to chaperone "clients".

Figures 4C, 4D:
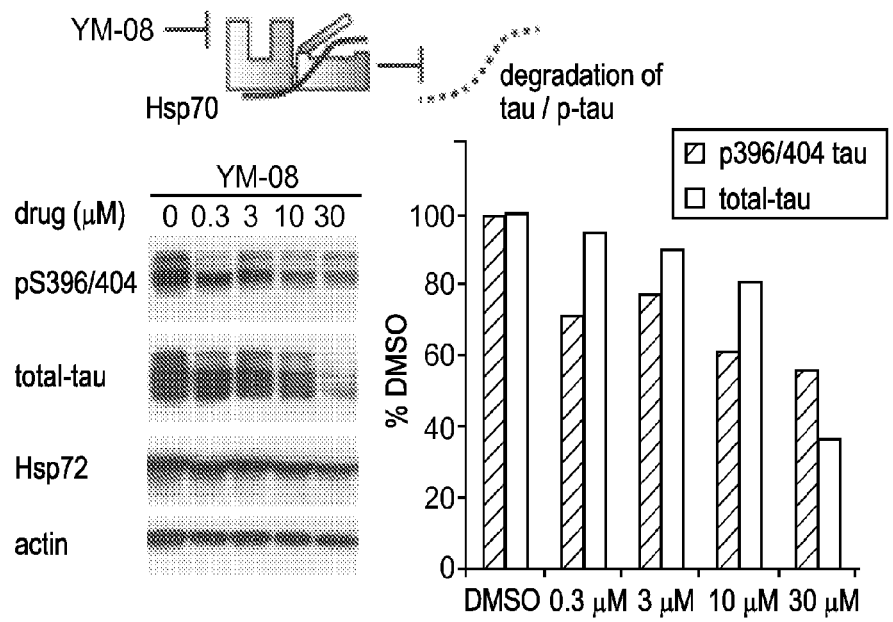

Hsp70 inhibitors, including MKT-077, have been shown to accelerate degradation of tau and affect processing of other chaperone-dependent substrates in cells. To determine whether YM-08 might also accelerated tau degradation, HeLaC3 cells, which stably over-express human 4R0N tau, were treated with compound. After 24 hours, the levels of phosphorylated (p396/404) tau and total tau were measured by Western blot. The results showed that YM-08 (30 μM) decreased the levels of pS396/404 and total tau by about 40% and about 60%, respectively (FIG. 4C). This cellular activity is not as dramatic as that of MKT-077, which reduced tau levels by >80% at 30 μM (FIG. 4D); however, reducing tau by only about 50% is predicted to provide benefits in some AD models Importantly, it was confirmed that, like MKT-077 and other Hsp70 inhibitors, YM-08 did not induce a stress response, based on the unchanged levels of stress inducible Hsp72 (HSPA1) in the treated cell lysates (FIG. 4C). Finally, all of the truncated compounds had significantly reduced anti-tau activity (FIG. 4D), consistent with the in vitro binding studies and the proposed importance of each of the three ring systems.

YM-08 was tested whether it might retain the anti-cancer activity of MKT-077. MTT assays showed that MKT-077 had $EC_{50}$ values between 1.4 and 3.0 μM against MCF-7, MCF-10A and MB-MDA-231 cells (FIG. 4D). YM-01 had similar activity ($EC_{50}$ values between 2.0 and 5.2 μM), while YM-08 had diminished potency, with $EC_{50}$ values between 7.8 and 10.5 μM (FIG. 4D). Notably, the truncated molecules tended to have poor activity (most $EC_{50}$ values >30 μM), consistent with the binding results. It is possible that the residual activity for YM-02 and YM-07, especially in MCF7 cells (FIG. 4D), may arise from off-target effects.

Because MKT-077 binds to a dynamic, allosteric site on Hsp70 that is not overlapping with the nucleotide-binding cleft (see FIG. 3) and is far removed from the peptide-binding region, it was not expected to be direct correlations between the calculated binding affinity values and any effects on chaperone functions or cellular activity. Consistent with this idea, the preliminary structure-activity relationships (SAR) for this chemical series were complex, especially when comparing in vitro values to potency in cellular assays. For example, the truncated molecule YM-02 had weak affinity ($IC_{50}$>50 μM) for Hsp70 in vitro (see FIG. 2A), yet it has some residual activity in the luciferase binding (FIG. 4B) and cell-based anti-tau assays (FIG. 4D). Also, YM-08 had a superior affinity for Hsc70 (see FIG. 2), but reduced anti-tau activity in cells when compared to the parent molecule MKT-077 (see FIG. 4C). Regardless of the allosteric/mechanistic origins of these differences, the results suggest that removing either the benzothiazole (e.g. YM-07) or the pyridine/pyridinium (e.g. YM-02) reduced potency across all of the assay formats. Also, the results support the conservative conclusions that YM-08 retained binding to Hsp70 and that it modestly reduced tau levels in cultured cells.

YM-08 activity in a more physiological system was tested. Brain slice cultures from transgenic mice that express mutated tau were treated for 6 hours with YM-08 and the levels of total- and pS396/404 tau measured by Western blots. At both 30 and 100 μM concentrations, YM-08 reduced phospho-tau in this model (FIG. 5A), consistent with the cell culture model. Thus, YM-08 also reduced the levels of disease-associated tau in a neuronal model. Recent findings suggest that Hsp70 binds tau immediately after its release from microtubules. To test whether YM-08 might selectively reduce tau after microtubule disruption, brain slices were cultured from wild type mice and treated them with YM-08 plus the microtubule destabilizer, nocodazole. Treatment of these cultures with YM-08 alone did not significantly reduce tau levels (FIG. 5B), consistent with the idea that most tau in non-pathogenic conditions is associated with microtubules and not available for removal through the Hsp70 system. However, acute disruption of the microtubule network with nocodazole dramatically increased the potency of YM-08 and led to decreased levels of both total and phospho-tau (FIG. 5B). Together, these studies add to growing evidence that Hsp70 selectively identifies tau variants that are not associated with the normal microtubule network, likely minimizing their aggregation and proteotoxicity. Further, these results suggest that enhancing the affinity of Hsp70 for tau, using molecules such as YM-08, promotes proper tau triage.

The relative stability and pharmacokinetics of a charged (YM-01) and neutral (YM-08) analog were explored. To test their stability in aqueous media, YM-01 or YM-08 (100 μM) was incubated in water at room temperature and found that both compounds were stable for at least 8 hours (FIG. 6A).

Figure 6C:
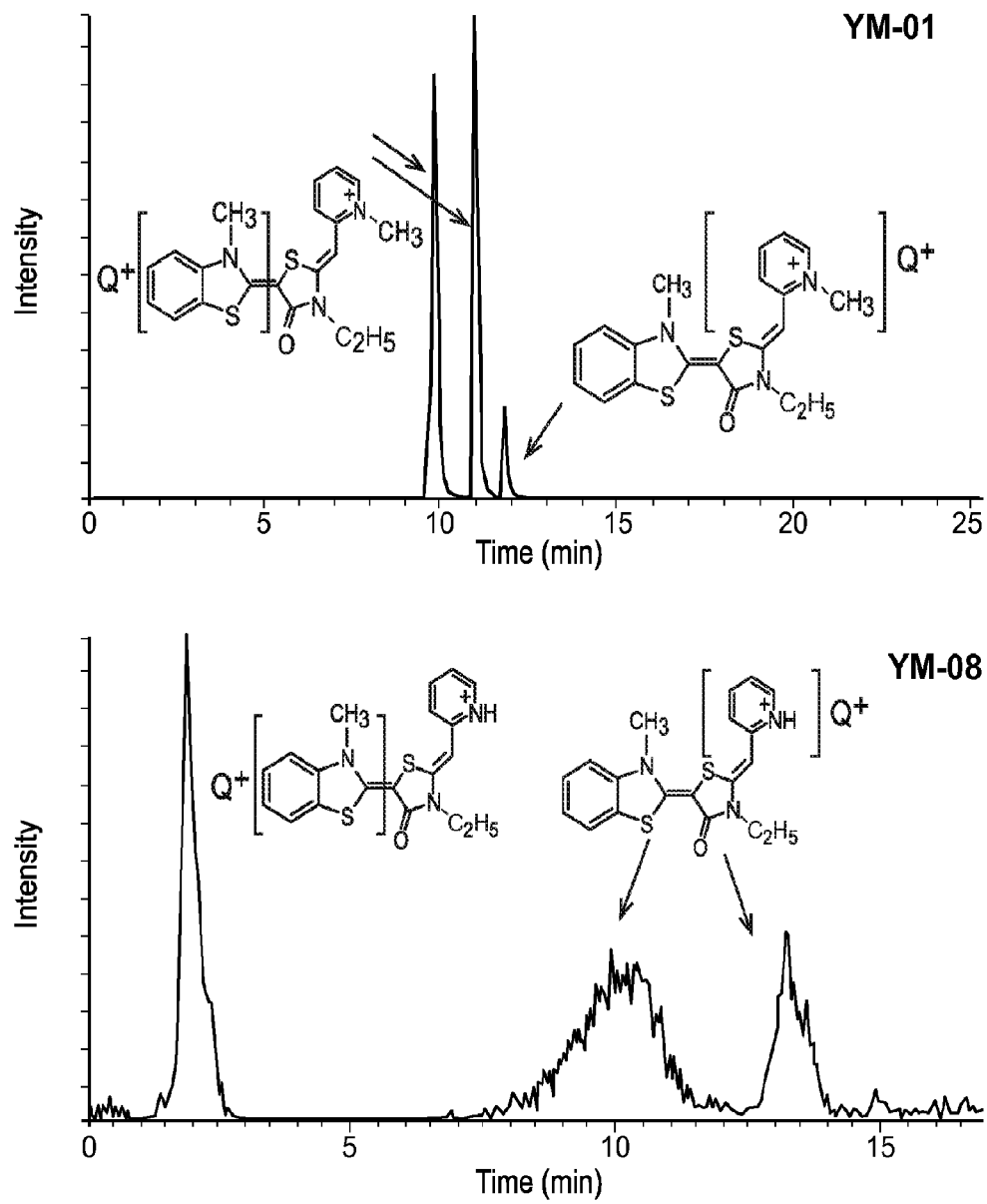
FIG. 6 shows the initial characterization of YM-08 stability and metabolism. (A) Both YM-01 and YM-08 (100

As an initial examination of the metabolism of YM-08, its stability in the presence of human liver microsomes was studied. In this system, both YM-01 and YM-08 were rapidly metabolized ($t_{1/2}$ values of about 2 to 4 min) (FIG. 6B), largely by oxidation on the benzothiazole and pyridine ring systems (FIG. 6C). MKT-077 has a similar reported rate of metabolism. Together, these results indicate that replacement of the charged pyridinium did not significantly impact metabolic or aqueous stability.

The initial pharmacokinetics (PK) of YM-01 and YM-08 were tested in CD1 mice. YM-01 (20 mg/kg; saline) was prevalent in the kidney at both 0.16 and 1 hrs after i.v. injection, but it lacked detectable brain penetration (FIG. 7A). This result is consistent with the known properties of MKT-077. In contrast, YM-08 (10 mg/kg; 10% DMSO/saline (v/v) i.v.) was abundant in the brain at 0.16 hrs, with reduced retention in the kidney and rapid clearance from all compartments (FIG. 7A). These results suggested that YM-08 was BBB permeable, consistent with its design. While these preliminary PK results were promising, YM-08 was only marginally soluble in the DMSO/saline mixture, so it was re-formulated in a Cremophor mixture, and a more definitive analysis of the brain and plasma levels was performed over time in CD1 mice. After a single 6.6 mg/kg dose delivered i.v., the peak brain concentration of YM-08 was 4 µg/g (FIG. 7B) and the ratio in the brain:plasma (B/P) ratio was approximately 0.25 for 18 hrs (FIG. 7C). Typically, B/P values greater than 0.3 are considered promising for CNS leads, suggesting that, with additional optimization, YM-08 could be a promising analog. It is not yet clear how much tau levels need to be reduced to achieve therapeutic effects in disease models, but the area-under-the-curve ($AUC_{inf}$) for YM-08 in the brain was 0.26 µg·hr/g and the $AUC_{inf}$ in plasma was 13.6 µg·hr/mL. The terminal halftime in the brain ($t_{1/2; brain}$) was 6.8 hrs and the $t_{1/2; plasma}$ was 9.8 hrs, consistent with the rapid metabolism observed in the liver microsome studies.

Thus, derivatives of MKT-077 bind Hsp70, inhibit ATP turnover and enhance binding of Hsp70 to its "clients". Although YM-08 was somewhat less effective then MKT-077 in anti-tau and anti-cancer assays, it was BBB permeable and was not retained in the kidney.

Compounds

Disclosed herein are compounds having a structure of formula (I), (II), (III), (IV), or (V), with the substituents as defined above:

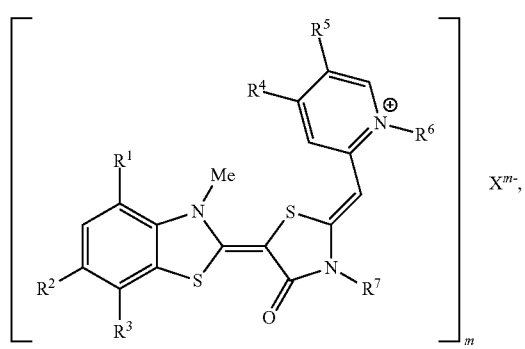

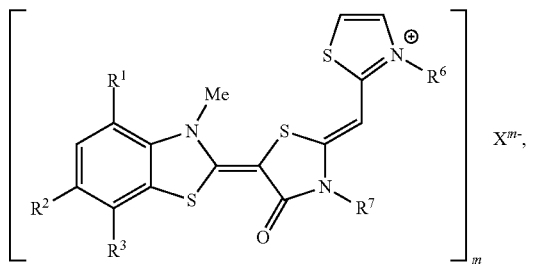

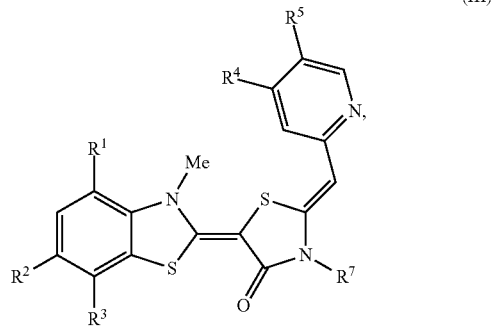

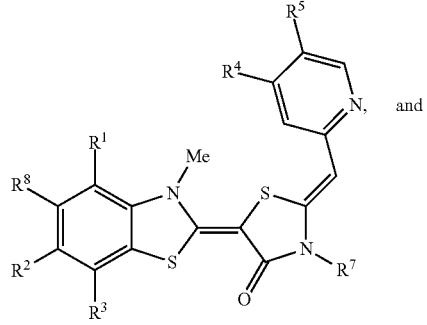

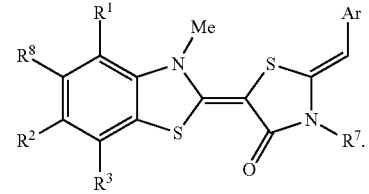

The term "alkyl" used herein refers to a saturated straight or branched chain hydrocarbon group of carbon atoms, including, but not limited to, methyl, ethyl, n-propyl, isopropyl, n-butyl, isobutyl, tert-butyl, and the like. Alkyls of one to four carbon atoms are contemplated.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $CF_3$, $NO_2$, CN, NC, OH, alkoxy, amino, $CO_2H$, $CO_2$alkyl, OC(O)alkyl, aryl, and heteroaryl. Exemplary aryl groups include, but are not limited to, phenyl, naphthyl, tetrahydronaphthyl, fluorophenyl, chlorophenyl, difluorophenyl, dichlorophenyl, chlorofluorophenyl, dicholorfluorophenyl, chlorodifluorophenyl, trifluorophenyl, trichlorophenyl, methylphenyl, methoxyphenyl, trifluoromethylphenyl, nitrophenyl, 2,4-methoxychlorophenyl, and the like.
Specifically contemplated compound of any one of formulae (I)-(V) include
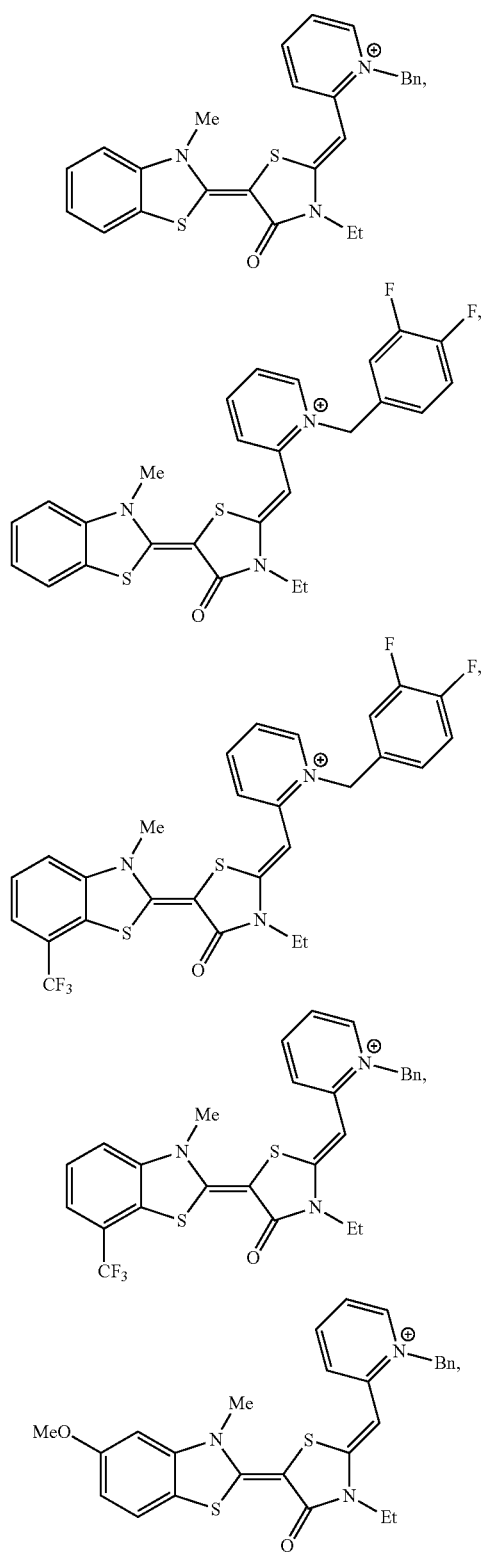
-continued
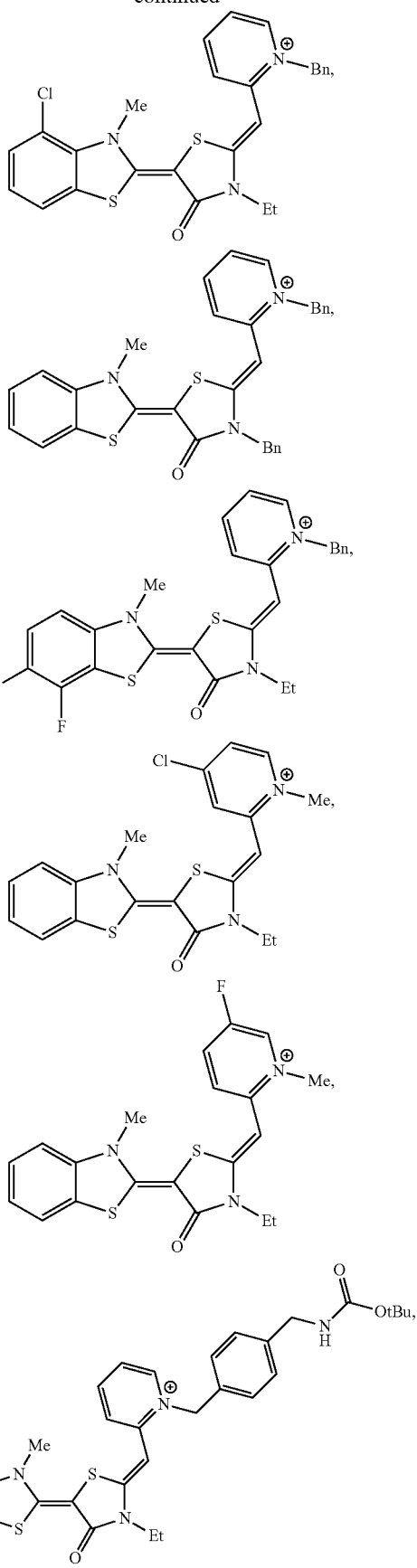

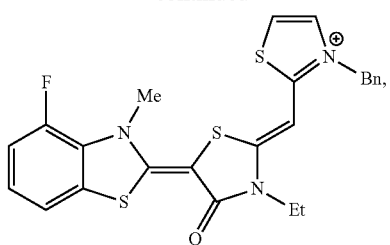
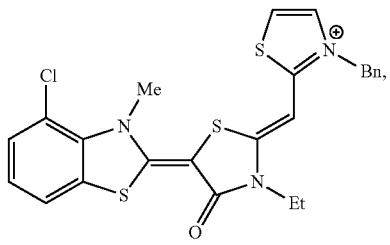
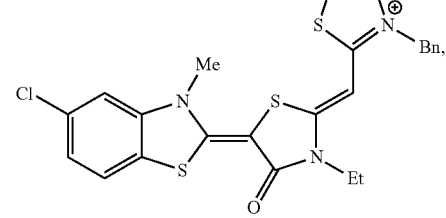
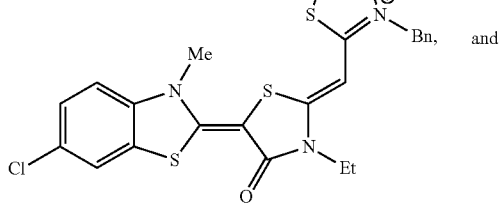
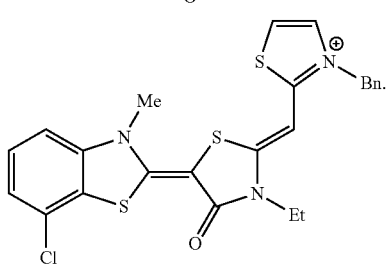
In some cases, the compound is selected form
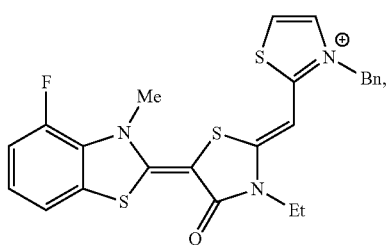
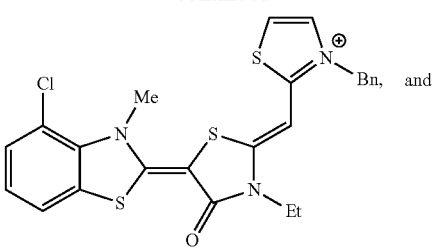
In various cases, the compound is
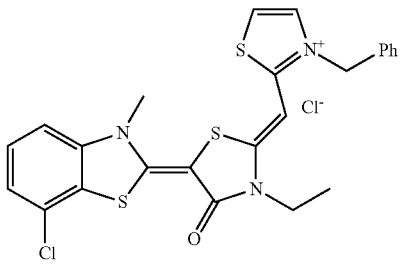
or a salt thereof.
Further contemplated are compounds, or salts thereof, having a structure selected from the group consisting of -continued

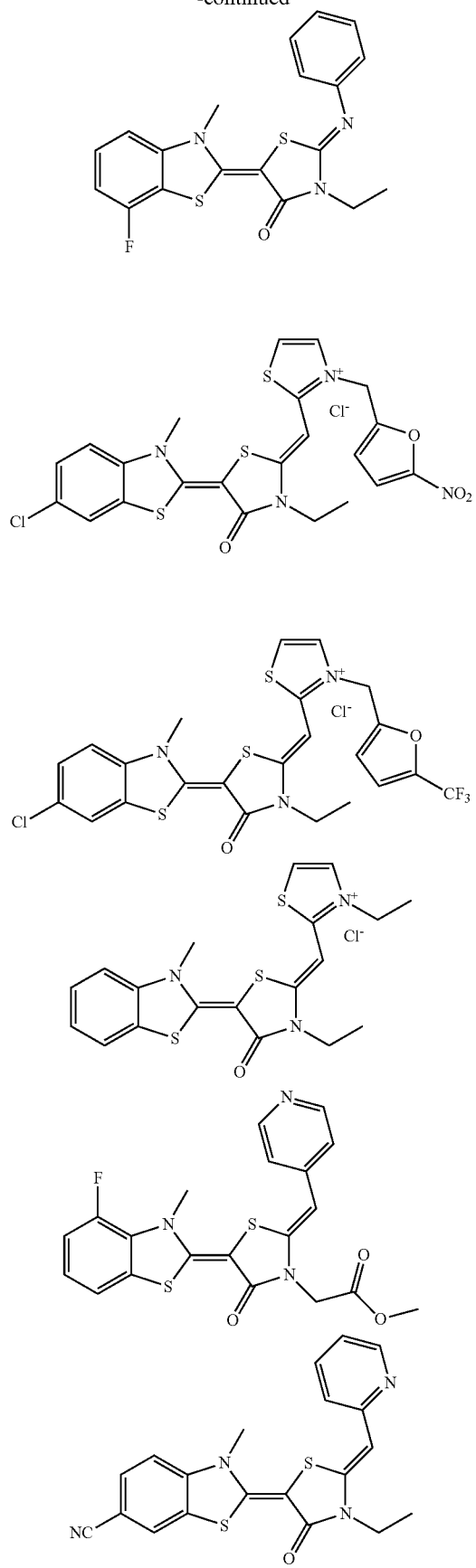

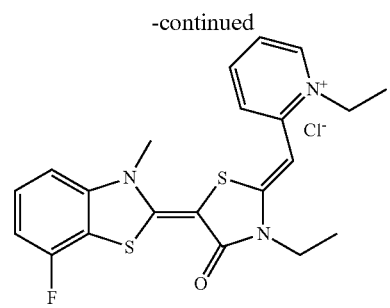
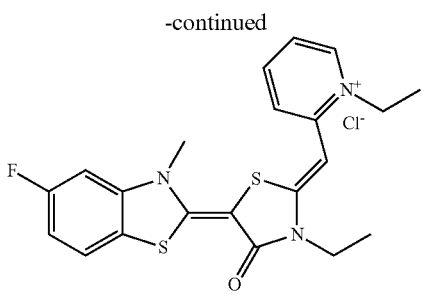

-continued
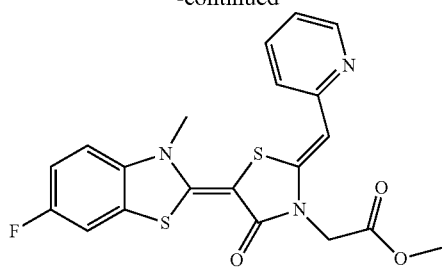
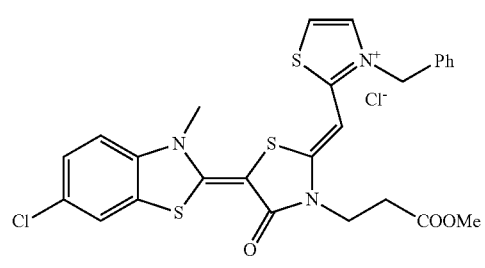
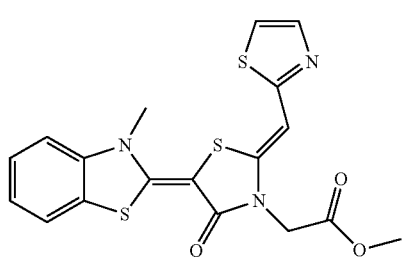
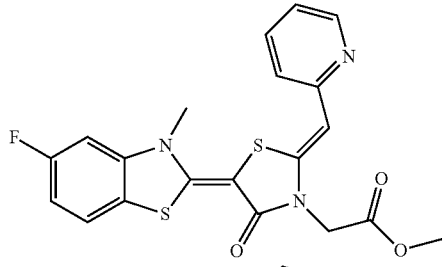
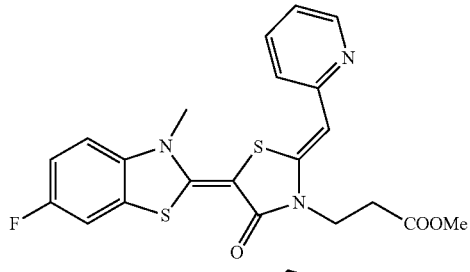
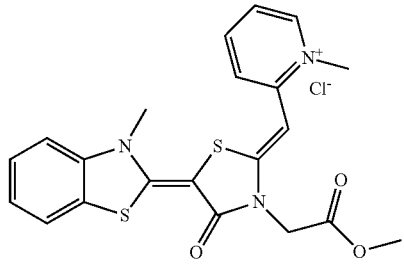
-continued
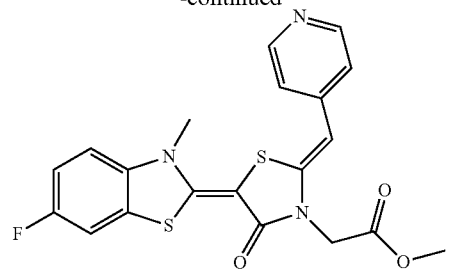
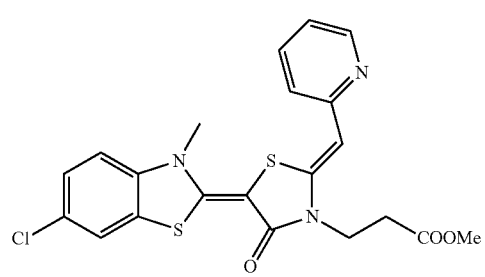
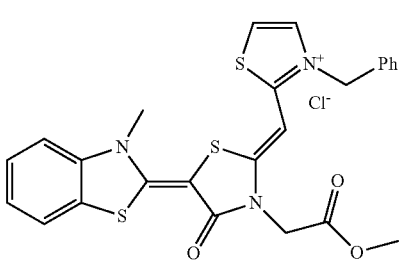
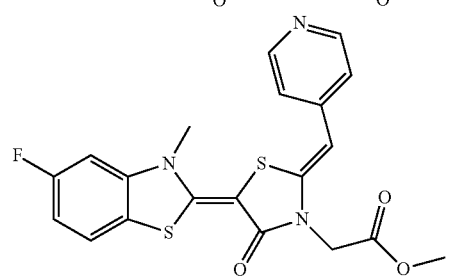
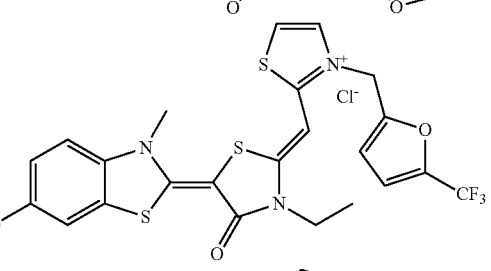
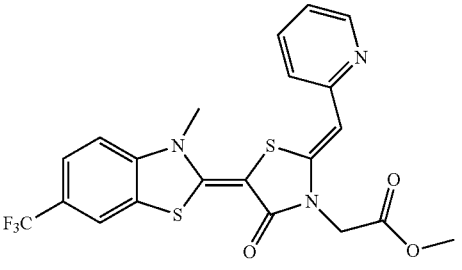

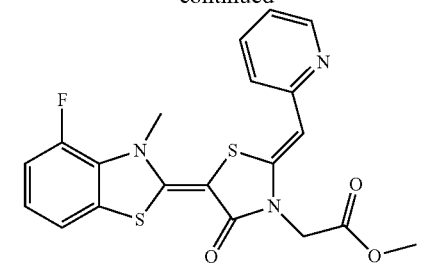
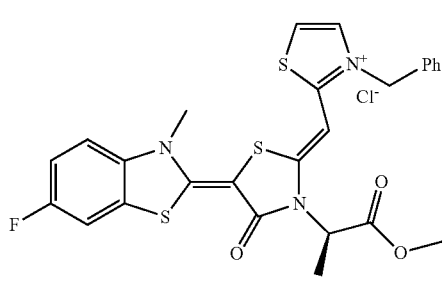
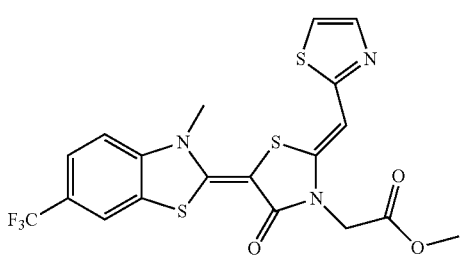
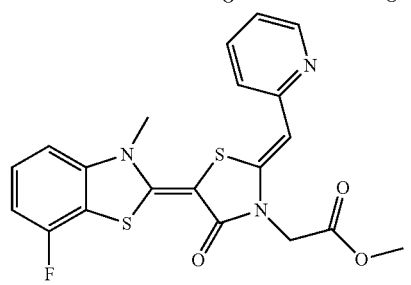
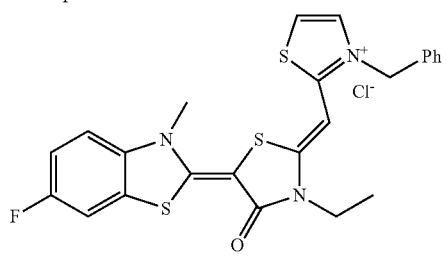
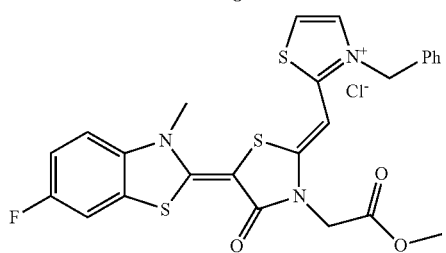
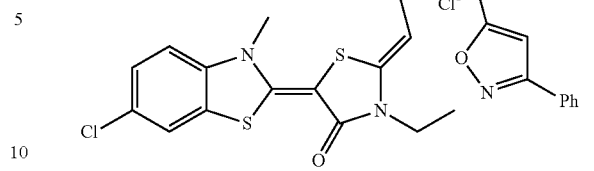
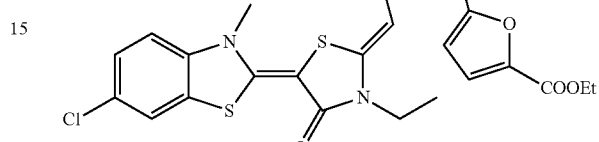
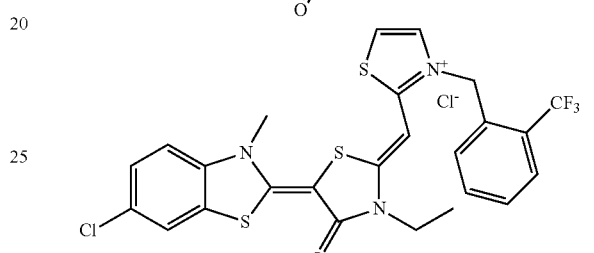
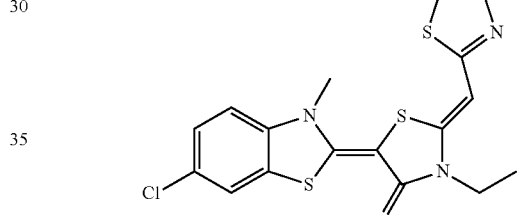
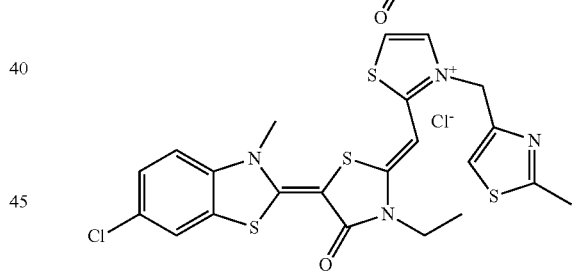
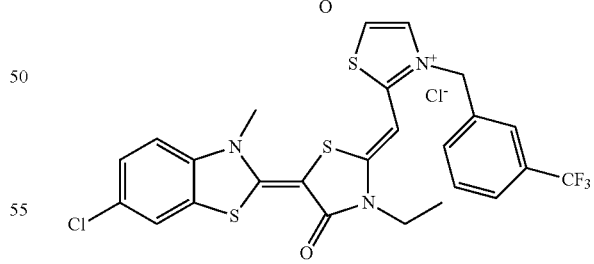
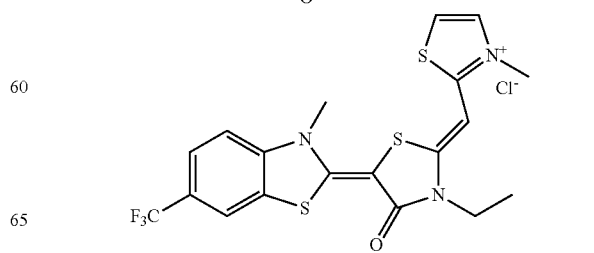

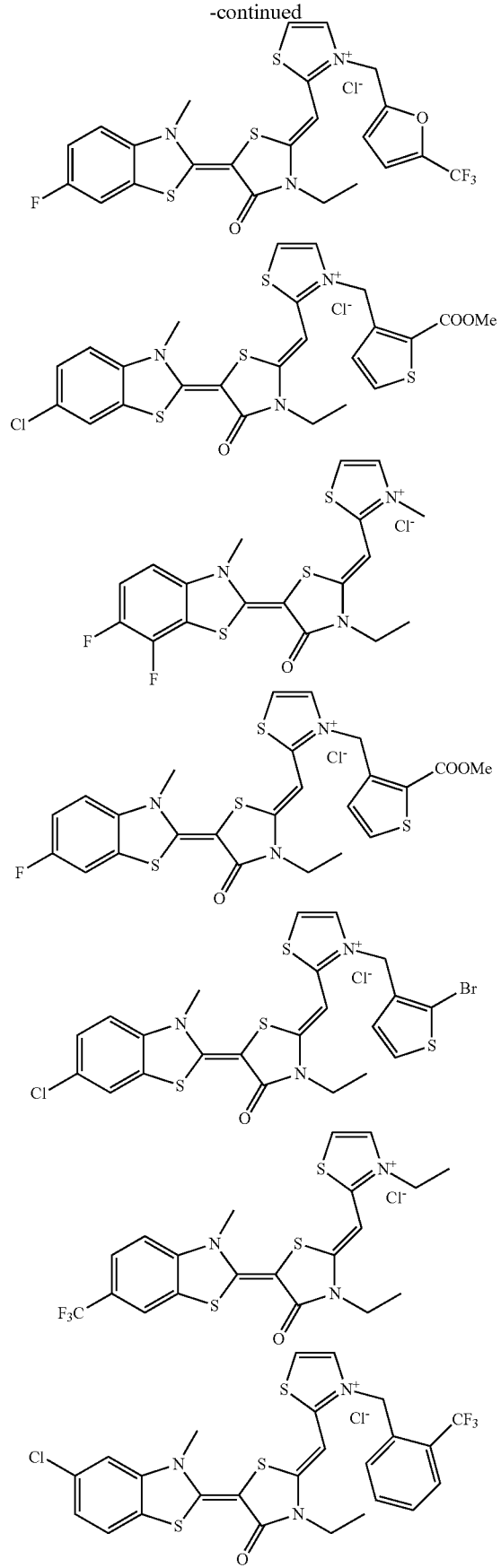
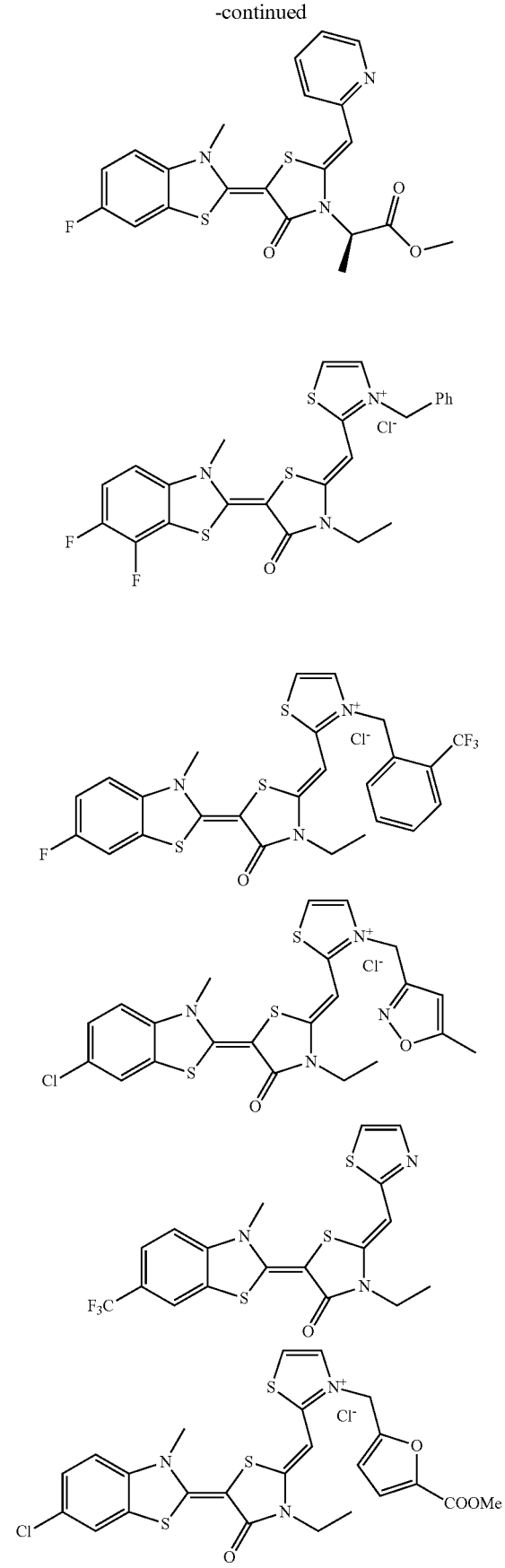

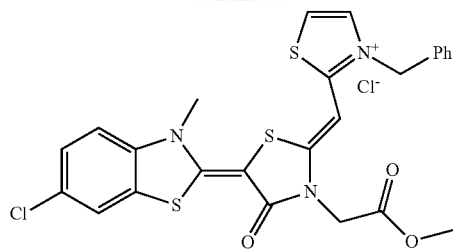
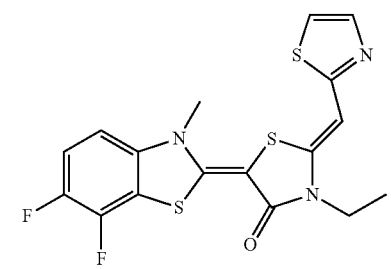
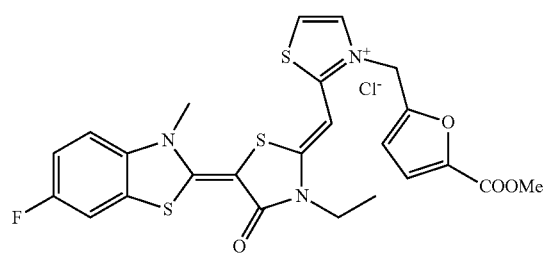
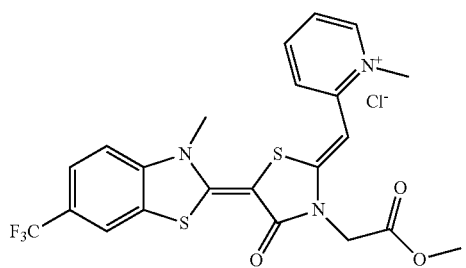
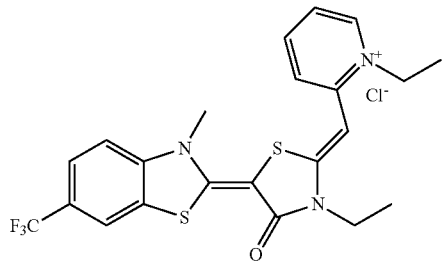
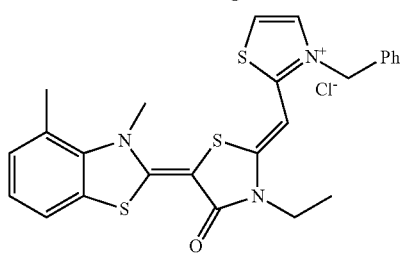
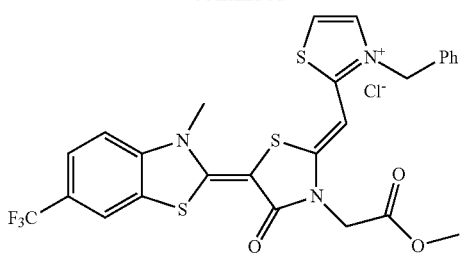
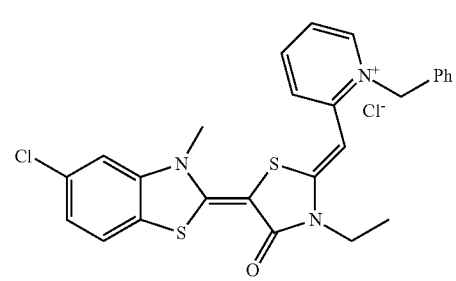
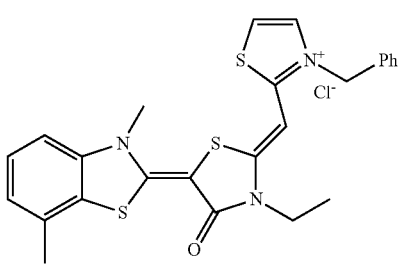
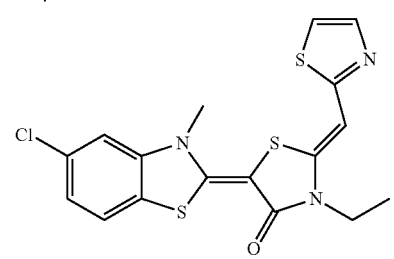
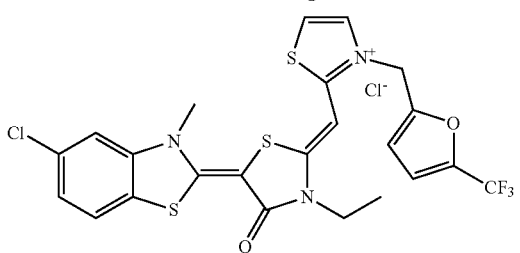
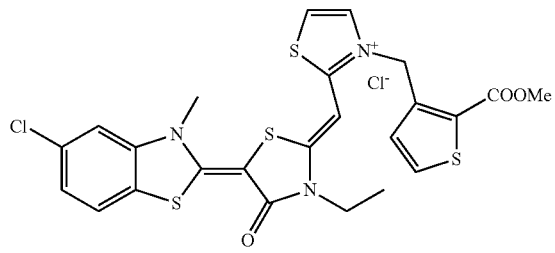

-continued
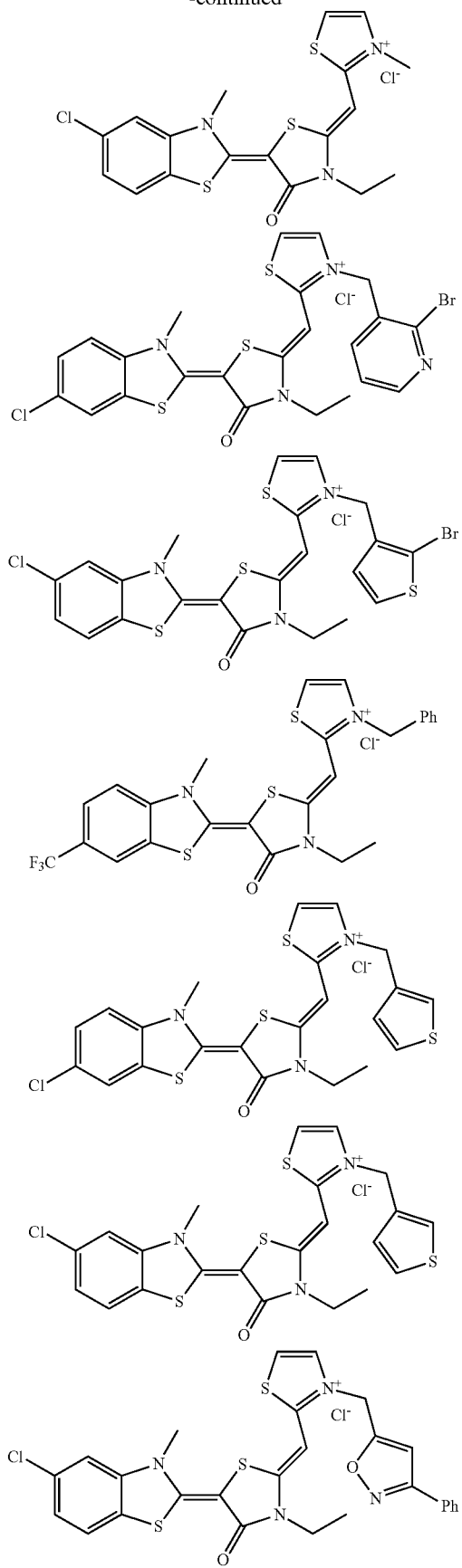
-continued
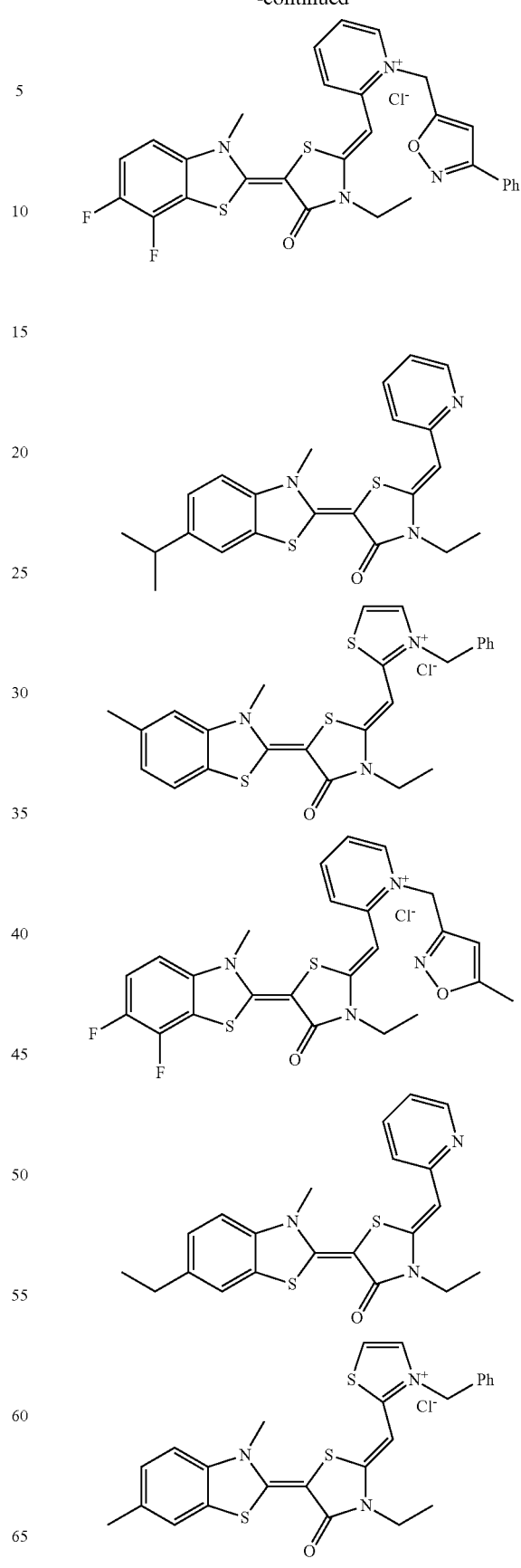

35
-continued
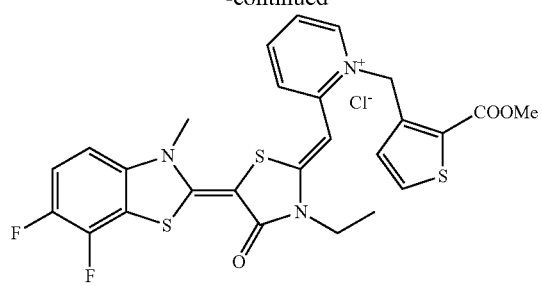
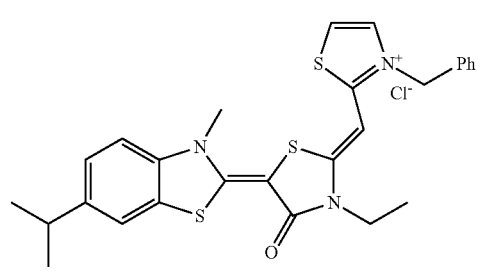
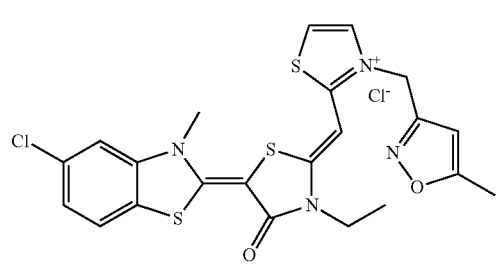
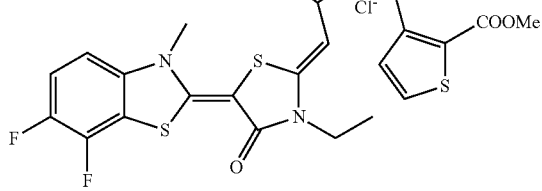
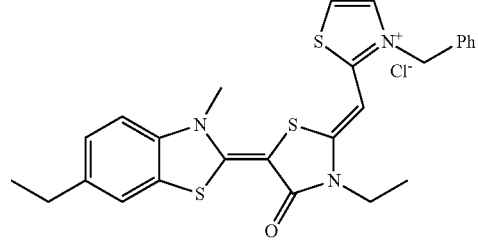
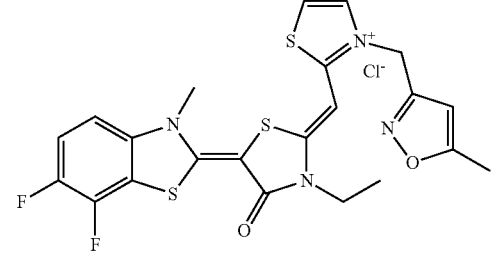
36
-continued
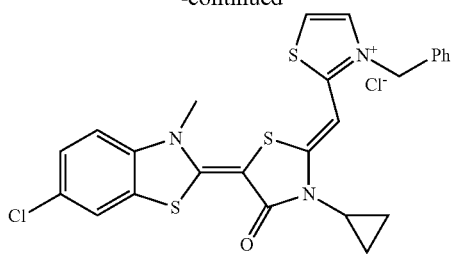
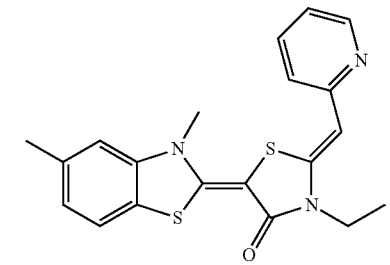
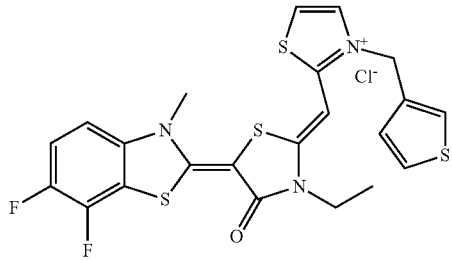
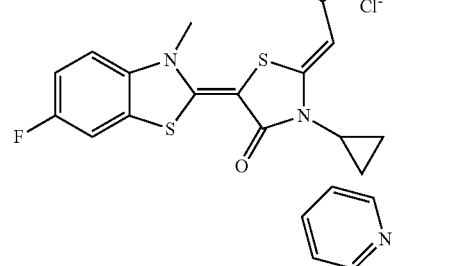
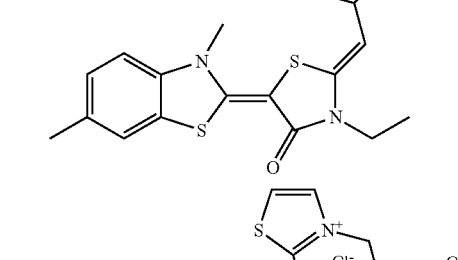
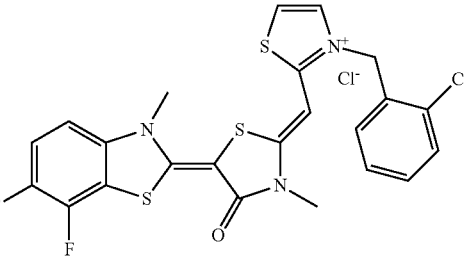

37
-continued
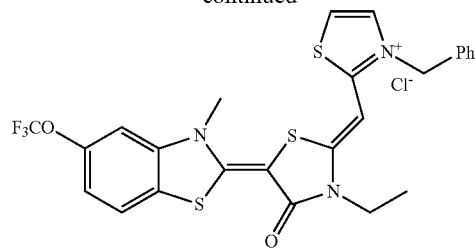
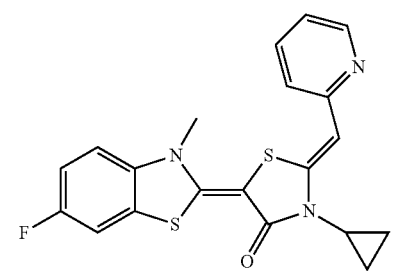
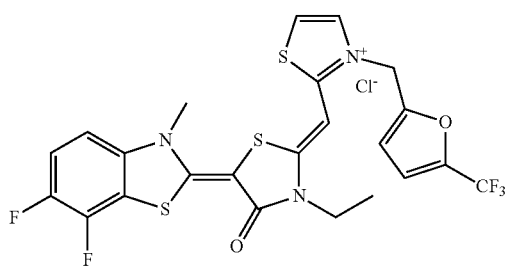
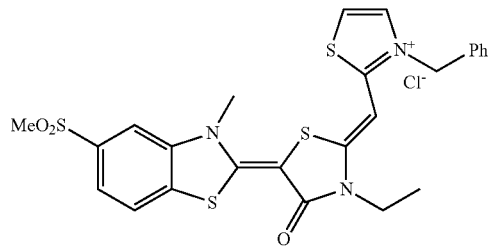
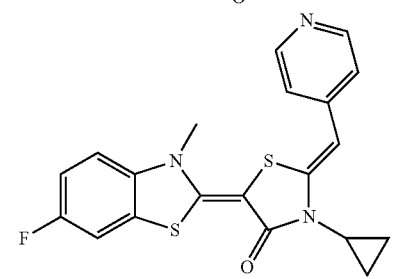
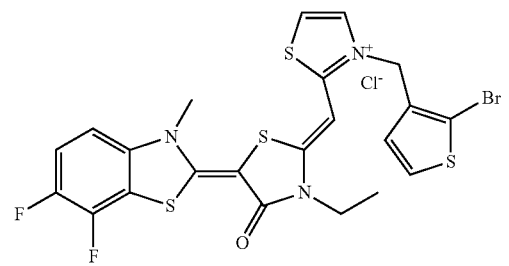
38
-continued
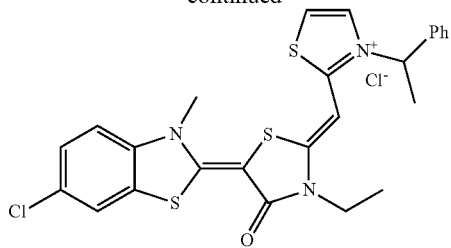
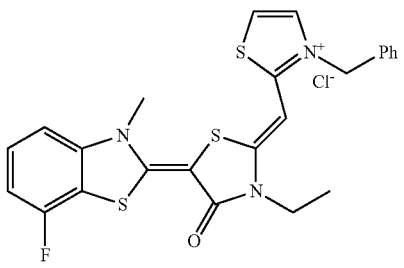
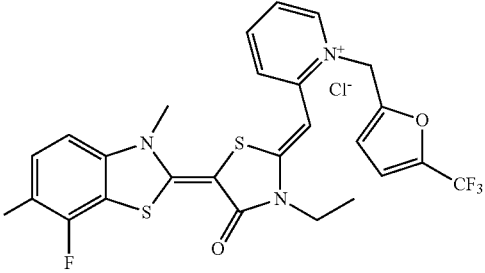
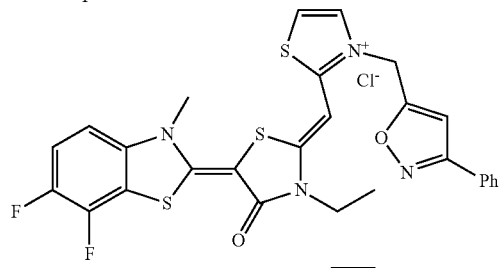
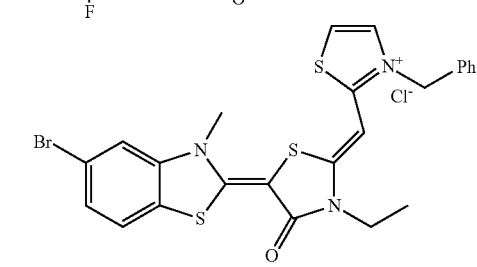
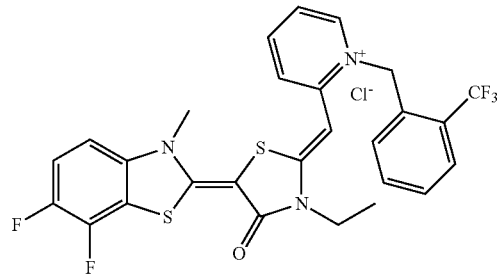

39
-continued
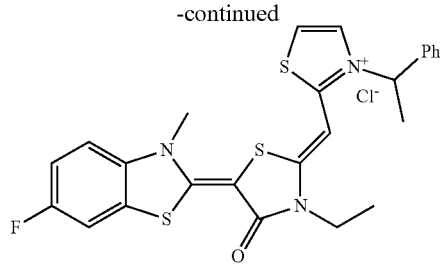
40
-continued
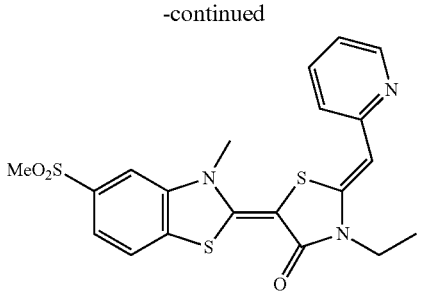
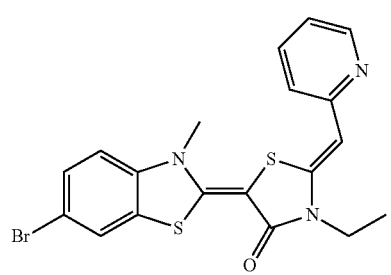
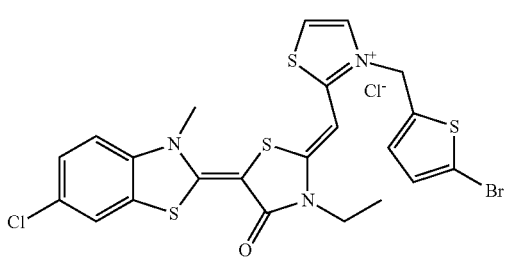
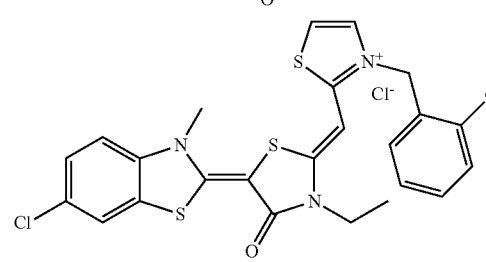
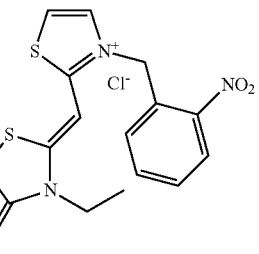
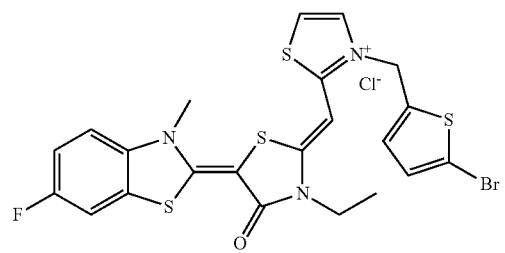

-continued

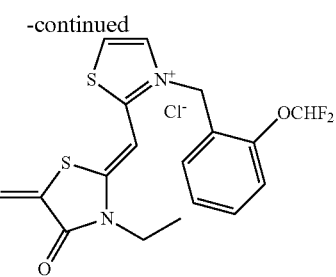

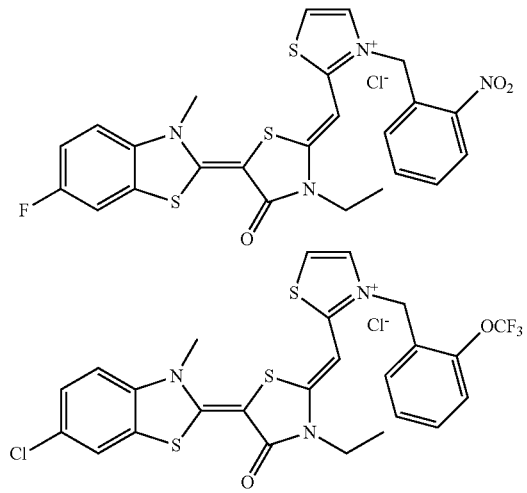

-continued

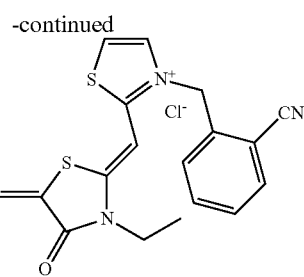

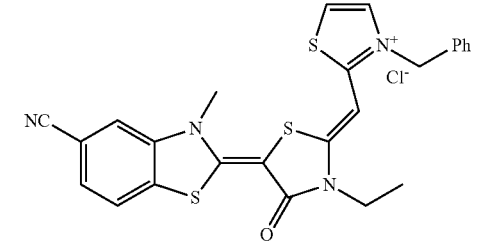

While the compounds shown above may indicate a specific salt (e.g., Cl⁻ or TsO⁻) each of the structures is specifically contemplated as a generic acid addition salt X⁻ as disclosed herein, and discussed directly below.

Pharmaceutically acceptable salts of compounds disclosed herein can be acid addition salts, e.g., a salt of the compound disclosed with a corresponding pharmaceutically acceptable anion. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts (anions) thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Synthesis

The Compounds Disclosed Herein can be Prepared Via any Methodology. As a guide, provided here is a description of one means by which the compounds can be synthesized.

Figure 1:
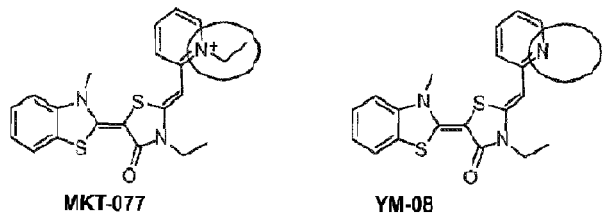
FIG. 1 shows a synthetic scheme for MKT-077 and its derivatives. (A) Chemical structures of MKT-077 and YM-08, highlighting the pyridine ring. (B) Synthetic route used to generate cationic molecules, MKT-077, YM-01 and the intermediates YM-02 and YM-03. Overall yield of MKT-077 and YM-01 was about 25%. (C) Synthetic route to neutral YM-08, starting from common intermediate 5 (YM-03). Overall yield of YM-08 was about 25%. The structures of two control compounds, YM-04 and YM-07 are shown.
Figure 1:
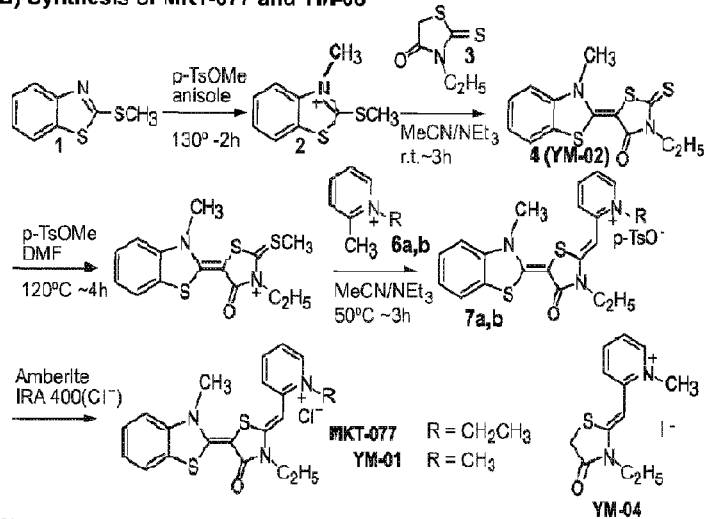
Figure 1:
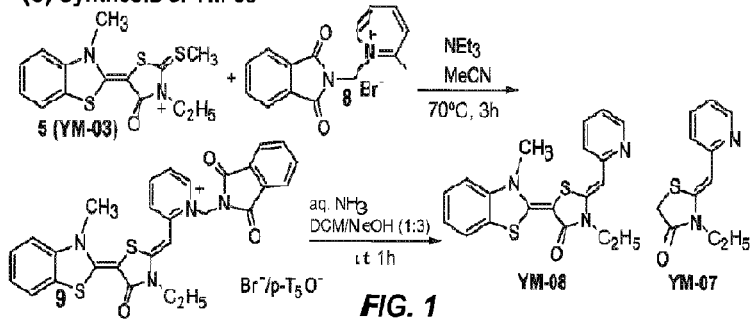

MKT-077 and derivatives were synthesized using a synthetic route as reported in JP 2004359801, see FIG. 1B. Briefly, this synthesis progressed through reaction of 2-(methylthio)benzothiazole (1) with p-TsOMe to afford its methylthioiminium salt, which was subsequently condensed with rhodanine (3) to afford compound 4 (YM-02). Compound 4 was further activated by p-TsOMe to yield intermediate 5 (YM-03), followed by condensation with either 1,2-dimethylpyridin-1-ium (6a) or 1-ethyl-2-methylpyridin-1-ium (6b) to afford 7a and 7b. Final counter-ion exchange yielded MKT-077 and YM-01 in good overall yield (about 25%). Adding to this series intermediates 4 and 6b were condensed to produce a truncated analog, YM-04, which lacks the benzothiazole group. Next, the neutral compound, YM-08, was synthesized via condensation of the common intermediate 4 with 1-((1,3-dioxoisoindolin-2-yl)methyl)-2-methylpyridin-1-ium bromide (8) to yield compound 9 (FIG. 1C). Deprotection of 9 with aqueous ammonium hydroxide yielded YM-08 in about 25% overall yield. As another control, YM-07, a neutral analog of YM-04, was synthesized using a route reported in Pudhom, et al. *Bioorg. Med. Chem.*, 14:8550-8563 (2006).

Pharmaceutical Formulations and Routes of Administration

Compositions of compounds as disclosed herein are provided. In some embodiments, compositions are provided that comprise an effective amount of a compound as disclosed herein and an acceptable excipient. In some cases, the excipient is a pharmaceutically excipient carrier.

The term "effective amount" as used herein, refer to an amount of a compound sufficient to affect the desired outcome, e.g., regulate tau and/or polyQ, treat, ameliorate, or prevent the identified disease or condition (e.g., a tauopathy or a cancer), or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Compositions can comprise an amount of a compound as disclosed herein of 0.01 mg to 5 g. Specific ranges of amounts of a compound as disclosed herein include 0.1 mg to 1000 mg, 1 mg to 500 mg, 1 mg to 400 mg, 1 mg to 300 mg, 1 mg to 200 mg, 1 mg to 150 mg, and 1 mg to 100 mg. Additionally or alternatively, the amount of compound in a composition as disclosed herein is measured in mg/kg. Contemplated mg/kg doses of the disclosed compounds include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

In various embodiments, administration of a composition as disclosed herein is by a single administration of the composition, or can be administered over a period of time, either in divided doses or in a continuous-release composition or administration method (e.g., a pump). However the compounds of the embodiments are administered to the subject, the amounts of compound administered and the route of administration chosen should be selected to permit efficacious treatment of the disease condition. The composition can be administered once per day, twice per day, three times per day, four times per day, once every other day, once every third day, once a week, once a month, once every other month, once every six months, or once a year.

The term "pharmaceutically acceptable excipient" refers to an excipient for administration of a pharmaceutical agent, such as the compounds described herein. The term refers to any pharmaceutical excipient that may be administered without undue toxicity. Excipients include carriers, solvents, stabilizers, adjuvants, diluents, etc.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

In some embodiments, the pharmaceutical composition is formulated to achieve a physiologically compatible pH, and may range from a pH of about 3 to a pH of about 11, about pH 3 to about pH 7, depending on the formulation and route of administration. In alternative embodiments, the pH is adjusted to a range from about pH 5.0 to about pH 8. More particularly, in various cases, the pharmaceutical compositions comprise a therapeutically or prophylactically effective amount of at least one compound as described herein, together with one or more pharmaceutically acceptable excipients.

The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release compositions are be prepared from the agents described herein in order to achieve a controlled release of the active agent in contact with the body fluids in the gastro intestinal tract, and to provide a substantial constant and effective level of the active agent in the blood plasma. In some cases, the crystal form of a compound as disclosed herein is embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Compositions, e.g., for parenteral or oral administration, are most typically solids, liquid solutions, emulsions or suspensions, while inhalable formulations for pulmonary administration are generally liquids or powders. In various cases, a pharmaceutical composition is formulated as a lyophilized solid that is reconstituted with a physiologically compatible solvent prior to administration. Alternative pharmaceutical compositions are formulated as syrups, creams, ointments, tablets, and the like.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay carrier such as glyceryl monostearate or glyceryl distearate alone or with a wax may be employed.

Compositions for oral use may be also presented as hard gelatin capsules wherein the active ingredient is mixed with an inert solid excipient, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions are formulated as suspensions comprising a compound of the embodiments in admixture with at least one pharmaceutically acceptable excipient suitable for the manufacture of a suspension.

In yet another embodiment, pharmaceutical compositions are formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). In some cases, the suspensions also contain one or more preservatives (e.g., acetic acid, methyl or n-propyl p-hydroxy-benzoate); one or more coloring agents; one or more flavoring agents; and one or more sweetening agents such as sucrose or saccharin.

In various embodiments, the pharmaceutical compositions are oil-in water emulsions. The oily phase may be a vegetable oil, such as olive oil or arachis oil, a mineral oil, such as liquid paraffin, or a mixture of these. Suitable excipients for oil-in-water emulsions include emulsifying agents such as naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. In some embodiments, the emulsion also contains sweetening and flavoring agents. In various cases, syrups and elixirs are formulated with sweetening agents, such as glycerol, sorbitol or sucrose. Such compositions, in some cases, also contain a demulcent, a preservative, a flavoring or a coloring agent.

Additionally, in various embodiments, the pharmaceutical compositions are sterile injectable preparation, such as a sterile injectable aqueous emulsion or oleaginous suspension. This emulsion or suspension may be formulated by a person of ordinary skill in the art using those suitable excipients, such as dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

In some cases, the sterile injectable preparation is prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein is dissolved in an aqueous solution of an organic or inorganic acid, such as 0.3 M solution of, e.g., succinic acid or citric acid. If a soluble salt form is not available, the compound is dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

In various embodiments, the pharmaceutical composition is a solution of a salt form of the compound in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein are formulated for oral administration in a lipid-based formulation suitable for low solubility compounds. Lipid-based formulations can generally enhance the oral bioavailability of such compounds. As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins are added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, about 1% to about 15% hydroxypropyl-o-cyclodextrin, and from about 2.5% to about 10% hydroxypropyl-o-cyclodextrin. The amount of solubility enhancer employed will depend on the amount of the compound of the invention in the composition.

Methods of Treatment

Methods disclosed herein include methods of treating cancer or a disorder associated with tau aggregation, or use of a compound as disclosed herein in the preparation of a medicament to treat cancer or a disorder associated with tau aggregation. Specific disorders contemplated are discussed in detail below.

Cancer

Provided herein are methods of different types of cancer in a subject (e.g., a mammal) in need thereof comprising administering to the subject the compound or composition as described herein in an amount effective to treat said cancer. In some cases, the mammalian subject is a human subject. Practice of methods described herein in other mammalian subjects, especially mammals that are conventionally used as models for demonstrating therapeutic efficacy in humans (e.g., primate, porcine, canine, or rabbit animals), is also contemplated. Standard dose-response studies are used to optimize dose and dosing schedule.

The disclosed methods are useful for treating cancer, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "cancer resistance" refers to an improved capacity of a subject to resist cancer growth, in particular growth of a cancer already had. In other words, the term "cancer resistance" refers to a decreased propensity for cancer growth in a subject.

In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Hürthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may be targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plamsa cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestimal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer a deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenstrom's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

Further contemplated are methods further comprising contacting a cancerous cell (or administering to a subject with cancer) a second therapeutic, in addition to the compound disclosed herein. The second therapeutic can be a proteasome inhibitor or a HSP90 inhibitor. The second therapeutic can be a chemotherapeutic, biological response modifying agent, or a immunotherapeutic agent.

Contemplated chemotherapeutics for use in combination therapies as disclosed herein include aspirin, sulindac, curcumin, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; and enzymes such as L-asparaginase Contemplated biological response modifying agents for use in combination therapies as disclosed herein include, but are not limited to, interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors and receptor tyrosin kinase inhibitors such as imatinib mesylate (marketed as Gleevac or Glivac) and erlotinib (an EGF receptor inhibitor) now marketed as Tarveca; anti-virals such as oseltamivir phosphate, Amphotericin B, and palivizumab; HSP90 inhibitors, such as 17-DMAG, radicicol, and NVP-AUY922; and proteasome inhibitors such as bortezomib and carfilzomib.

Contemplated immunotherapeutic agents for use in the combination therapies disclosed herein include, but are not limited to a Her2/neu receptor antibody such as trastuzumab (marketed as Herceptin®), an anti-CD52 antibody such as alemtuzumab (marketed as Campath®. MabCampath® or Campath-1H), an anti-CD33 antibody such as gemtuzumab linked to calicheamicin (marketed as Mylotarg®), an anti-CD20 antibody such as rituximab (marketed as Rituxan® and MabThera®), Ibritumomab tiuxetan (marketed as Zevalin®), anti-TNFα antibodies such as infliximab (marketed as Remicade®) or adalimumab (marketed as Humira®), a soluble TNFR2 molscule such as etanercept (marketed as Enbrel®), an antibody to the CD25 chain of the IL-2 receptor such as basiliximab (marketed as Simulect®), an anti CD40/CD40L antibody such as humanized IgG1 anti-human CD40 antibody (SGN-40), an anti-CTLA-4 blocking antibody such as iplimumab (marketed as MDX-101 or MDX-010) or tremelimumab, an anti-programmed death protein 1 (PD-1) antibody (i.e., an anti-CD279 antibody), an anti-programmed cell death ligand (PDL-1) antibody, an anti-glucocorticoid-induced TNFR-related gene (GITR) antibody, an anti-OX-40 (CD134) antibody, soluble lymphocyte-activation gene 3 (also known asLAG3 or CD223)-based immune modulator such as LAGS-Ig (IMP321), Toll-like receptor agonists such as monophosphoril lipid A (MPL®), CpG, single-stranded RNA, nucleotides, nucleotide analogue, CL087 (a TLR7-specific ligand), loxoribine, polyinosine-polycytidylic acid, flagellin, resiquimod, immiquimod, gardiquimod, NOD ligands such as muramyl dipeptide, murabutide, peptidoglycan and muramyldipeptide.

Tauopathies

Further provided are methods of regulating tau and/or polyQ, comprising contacting tau and/or polyQ with a compound as disclosed herein. The neutral compounds can cross the blood brain barrier to impact tau aggregation and/or polyQ, which can lead to treatment or amelioration of a tauopathy or neurodegenerative disorder. PolyQ refers to any protein having a stretch of consecutive glutamine residues, which are linked to a disease. Examples include huntingtin, androgen receptor, and ataxin-2.

In some cases, methods are provided that reduce tau aggregation and/or reduce polyQ aggregation, comprising contacting aggregates of tau and/or aggregates of polyQ with a compound as disclosed herein in an amount effective to reduce tau aggregation and/or polyQ aggregation. In various cases, methods are provided that reduce tau levels and/or reduce polyQ levels in a cell, comprising contacting the cell with a compound as disclosed herein in an amount effective to reduce tau levels and/or polyQ levels in the cell. In some cases, methods are provided that inhibit tau aggregation and/or inhibit polyQ aggregation in a cell, comprising contacting the cell with a compound as disclosed herein in an amount effective to inhibit tau aggregation and/or polyQ aggregation. In various cases, methods are provided that reverse tau aggregation and/or reverse polyQ aggregation in a cell, comprising contacting the cell with a compound as disclosed herein in an amount effective to reverse tau aggregation and/or polyQ aggregation. In various embodiments, regulation of tau and/or regulation of polyQ in the methods provided herein is in vitro, or in vivo, and, in some cases, is associated with a disease state as discussed herein.

In some cases, provided herein are methods that further include identifying a subject having a disorder affected by tau or polyQ and administering to the subject a compound as disclosed herein. The subject can be a mammal, or more specifically, a human.

In various cases, the methods provided herein are prophylactic methods, and a compound or composition as disclosed herein is administered prior to onset of a disorder. In certain cases, the method further comprises identifying a subject at risk of contracting a disorder associated with tau levels or aggregation and/or polyQ levels or aggregation, and administering an effective amount of a compound as disclosed herein.

In various aspects, the methods disclosed herein are useful for treating or ameliorating one or more symptoms of a neurodegenerative disorder. In some cases, the neurodegenerative disorder is one or more of Alzheimer's disease, Pick's disease, Progressive Supranuclear Palsy (PSP), fronto-temporal dementia (FTD), parkinsonism linked to chromosome 17 (FTDP-17), disinhibition-dementia-parkinsonism-amyotrophy complex (DDPAC), pallido-ponto-nigral degeneration (PPND), Guam-ALS syndrome, pallido-nigro-luysian degeneration (PNLD), Huntington's disease, Kennedy disease, dentatorubropallidoluysian atrophy, Spinocerebellar ataxia, Machado-Joseph disease, cortico-basal degeneration (CBD), and traumatic brain injury.

In some embodiments, regulation of tau and/or polyQ in the presence of a compound as disclosed herein is measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of compounds can be described as a sigmoidal curve expressing a degree of modulation as a function of concentration. The curve also theoretically passes through a point at which the concentration is sufficient to affect tau and/or polyglutamine aggregation and/or levels to an amount that is 50% that of the difference between minimal and maximal activity in the assay. This concentration is defined as the Inhibitory Concentration (50%) or $IC_{50}$ value. Determination of $IC_{50}$ values is made using conventional acellular assay techniques or cell based assay techniques.

Comparisons of the efficacy of compounds often are provided with reference to comparative $IC_{50}$ values, wherein a higher $IC_{50}$ indicates that the test compound is less potent, and a lower $IC_{50}$ indicates that the compound is more potent, than a reference compound. Compounds demonstrating $IC_{50}$ values of less than about 1500 µM, or less than about 1000 µM, or less than about 250 µM, or less than about 100 µM, or less than about 50 µM, or less than about 20 µM, or less than about 1 µM, or less than 750 nM, or less than 700 nM, or less than 650 nM can be employed in compositions or methods according to the invention.

The data obtained in such dose-response assays can be used as a factor in formulating a dosage range for use in subject, such as animals, mammals, and more specifically, humans. In some embodiments, the dosage of such compounds lies within a range of circulating concentrations that include the effective dose that produces a therapeutic response in 50% of the people taking it ($ED_{50}$) with little or no toxicity. The dosage can vary within this range depending upon the dosage form, and the route of administration utilized.

The methods of the embodiments also include the use of a compound or compounds as described herein together with one or more additional anti-tau therapeutic agents for the treatment of a tauopathy. Thus, for example, the combination of active ingredients may be: (1) co-formulated and administered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

The anti-tau therapeutic agent can be administered at the same time as the compound as disclosed herein, or at a different time (e.g., separated by a time period of about 1 hour to about 12 hours). In cases where the agents are administered at the same time, the agents can be co-formulated, or formulated in separate formulations but given at the same time or within about 30 minutes of each other.

In some cases, a compound disclosed herein is administered and/or formulated with an anti-tau therapeutic—e.g., an agent that treats or ameliorates a symptom of a tauopathy disorder. The anti-tau therapeutic can be, for example, one or more of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

More specifically, the anti-tau therapeutic is selected from the group consisting of β-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, preferably inhibitors of dipeptidyl peptidases, most preferably DP IV inhibitors; inhibitors of neutral endopeptidase, inhibitors of phosphodiesterase-4 (PDE-4), TNF-α inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Further examples of useful anti-tau therapeutic agents include specific β-amyloid antibodies (e.g., ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.), carbidopa/levodopa, pergolide, bromocriptine, ropinirole, pramipexole, entacapone, tolcapone, selegiline, amantadine, trihexyphenidyl hydrochloride, β-amyloid synthesis inhibitors Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.); amyloid protein deposition inhibitors SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

General Methods

Reagents were purchased from Sigma-Aldrich, Alfa Aesar, or TCI America, and directly used without further purification. NMR experiments were carried out using 600 MHz Varian NMR apparatus. Mass spectrometry data were collected on Micromass LCT Time-of-Flight mass spectrometer with electrospray ionization. Mammalian Hsp70 proteins were expressed, purified and handled as previously described 44.

Synthesis

MKT-077 analogs were synthesized as previously described (see Examples below for detailed synthesis and characterization of various compounds).

ELISA Competitive Binding Assay

A sample of Hsc70 (50 μL; 0.06 mg/mL) was immobilized in clear flat-bottom 96-well plate in MES buffer (50 mM 2-(N-morpholino)ethanesulfonic acid, pH 5.2) at 37° C. overnight. After discarding the excess protein solution, each well was washed three times with 150 μL TBS-T buffer (25 mM Tris, 140 mM NaCl, 2.7 mM KCl, 0.01% Tween-20, pH 7.4). Then, 1 μL of compound (1% DMSO) was diluted into 24 μL of binding buffer (100 mM Tris, 20 mM KCl, 6 mM $MgCl_2$, 0.01% Triton-X100) and incubated at room temperature for 30 min Biotin labeled MKT-077 (final concentration 1 μM; 25 μL) was subsequently added into each well and the mixture was incubated at room temperature for another 3 hrs. The wells were washed with 150 μL TBS-T buffer three times prior to blocking with 100 μL 3% bovine serum albumin (BSA) in TBS-T buffer for 5 min at room temperature. After the removal of the BSA solution, 50 μL of HRP-streptavidin (Pierce Biotechnology, 1:50000 TBS-T dilution) solution was added and the plates were incubated at room temperature for 1 hr. The HRP-streptavidin solution was removed and wells were washed three times with 150 μL TBS-T. TMS substrate (Cell Signaling Technology 100 μL) was added into each well and incubated at room temperature until a visible blue color was shown in wells (about 20 min) 1 M HCl stop solution was then added into each well to yield a yellow solution and the absorbance at 450 nm was recorded on SpectraMax M5 (Molecular Devices). In control experiments, the biotinylated MKT-077 bound to human Hsp72 (4.9±0.8 μM) and DnaK (16.7±3.1 μM) with similar affinities to human Hsc70 (6.4±0.23 μM), reinforcing the similarity amongst the Hsp70 family members in the reported MKT-077 binding site.

Biolayer Interferometry (Octet Red)

Biotinylated human Hsc70NBD or full length Hsp72 were first immobilized on super streptavidin biosensors (ForteBio, 18-5057) as follows: biosensors were soaked with MG buffer (100 mM Tris base, 20 mM KCl, 6 mM MgCl2, 0.01% Triton X-100, pH 7.4) for 10 min before moving them to wells either containing 200 μL 100 μg/mL biotinylated proteins or 100 μg/mL biocytin for 60 min. The free streptavidin sites were subsequently quenched with 100 μg/mL biocytin for 10 min. The biosensors were washed with MG buffer for 5 min prior to beginning the binding experiments. The association and disassociation steps were carried out in MG buffer with a constant 10% DMSO concentration. All steps were performed at room temperature and with 1000 rpm rotary shaking. Compounds were allowed to associate with the biosensor surface for 5 min and then to disassociate with the biosensor for 5 min Compounds were tested from low to high concentration in duplicates. Biocytin-loaded biosensors were used to correct the baseline drifts. The apparent affinities of YM-08 for $Hsc70_{NBD}$ and Hsp72 were calculated from both equilibrium measurements and global fits of the $k_{on}$ and $k_{off}$ values, yielding similar values.

Molecular Docking

AUTODOCK-4.2 was used for the docking of YM-08 to $Hsc70_{NBD}$ in complex with yeast Hsp110 (PDB code 3C7N). This target was chosen because it is the only Hsp70-like protein structure available that is in complex with ADP and $Mg^{2+}$. Prior to docking, the Hsp110 sequence was removed and the remaining $Hsc70_{NBD}$, ADP, and $Mg^{2+}$ were minimized using DOCK6 and Amber force field parameters as previously described 23. Then, using a 0.2-Å resolution AUTODOCK grid box that was centered around the known MKT-077 binding site, a Lamarkian genetic algorithm was performed with the following parameters: GA runs=100, initial population size=1500, max number of evaluations=long, max number of surviving top individuals=1, gene mutation rate=0.02, rate of crossover=0.8, GA crossover mode: two points, Caushy distribution mean for gene mutation=0, Cauchy distribution variance for gene mutation=1, number of generations for picking worst individuals=10. The docked structures were clustered and then evaluated using PyMOL. All calculations were completed on a Apple MacBookPro computer equipped with a 64-bit 2.4 GHz Intel Core 2 Duo processor running MacOSX 10.6.8.

ATPase Assay

Single turnover ATPase assays were performed as previously described in, e.g., Fewell, et al., *J. Biol. Chem.*, 279:51131-51140 (2004), and Chiang, et al., *Bioorg. Med. Chem.*, 17:1527-1533 (2009). Briefly, the yeast Hsp70, Ssa1p (about 0.2 µM), was prebound to α-[32P]ATP. The hydrolysis of ATP in the presence or absence of an equimolar amount of Hlj1 was measured by monitoring the generation of a-[32P]ADP by thin layer chromatography (TLC).

Luciferase Binding

Binding of prokaryotic Hsp70 (DnaK) to denatured luciferase was measured as previously described, in e.g., Miyata, et al., *J. Biomol. Screen*, 15:1211-1219 (2010). Briefly, firefly luciferase (0.2 mg/mL) was proteolyzed with trypsin and immobilized in 96-well microtiter plates. After washing, the binding of luciferase to DnaK (500 nM) was measured using an anti-DnaK antibody and HRP secondary antibody. A similar strategy was used to monitor binding of human Hsc70 to tau, as previously described in Thompson, et al., *ACS Chem. Biol.*, 7:1677-1686 (2012).

Cell and Brain Slice Culture

MCF7 cells were cultured in DMEM with 10% fetal bovine serum (Invitrogen) and 1% penicillin-streptomycin (Invitrogen). MCF10A cells were cultured in DMEM/F-12 with 10% FBS, 1% pen-strep, 5% horse serum (Invitrogen), 500 ng/ml hydrocortisone (Sigma), and 25 ng/ml epidermal growth factor (R&D Systems), 10 µg/mL bovine insulin (Sigma) and 100 ng/mL cholera toxin (Sigma). HeLaC3 cells were cultured in OptiMem (Invitrogen) with 10% FBS and 1% pen-strep. MDA-MB-231 cells were cultured in DMEM with 10% FBS, 1% pen-strep, and 1% non-essential amino acids (Invitrogen). All cells were maintained at 37° C. with 5% $CO_2$ in a humidified atmosphere. Brain slice cultures were created as previously described in Jinwal, et al., *J. Neurosci.*, 29:12079-12088 (2009), and treated for 6 hours with YM-08 at the indicated concentration.

Cell Survival Assay

Cell viability was determined using a methyl thiazoyl tetrazolium (MTT) colorimetric assay (ATCC, catalog number 30-1010K) with the following modifications. Briefly, cells (5×103) were plated into 96-well assay plates in 0.1 ml media and allowed to attach overnight. The cells were then treated with compound at various concentrations in 0.2 mL fresh media. After the 72-hour incubation period, cells were washed in PBS (3×100 µL), and 10 µL MTT reagent was added with 100 µL fresh media. The cells were then incubated for 4 hrs in a humidified chamber at 37° C. with 5% $CO_2$. Insoluble formazan crystals were solubilized by addition of 0.1 mL detergent solution (4 hrs at room temperature in the dark). Resulting colored solutions were then quantified at an absorbance of 570 nm.

Pharmacokinetics General Methods

Mouse liver microsomes (20 mg/ml) containing cytochrome P450, cytochrome b5, and NADPH-cytochrome c reductase were purchased from XenoTech, LLC (Lenexa, Kans.). β-NADPH, $MgCl_2$, and 0.1 M phosphate buffer were obtained from Sigma-Aldrich (St. Louis, Mo.). High-performance liquid chromatography (HPLC)-grade acetonitrile was purchased from Thermo Fisher Scientific (Waltham, Mass.). HPLC water was purified using a MilliQ water system (Millipore Corporation, Billerica, Mass.).

Characterization of Metabolites

To identify metabolites of YM-01 and YM-08, metabolized samples and two negative-controls were prepared. In the metabolized samples, 10 µM YM-01 or YM-08 was incubated with mouse liver microsomes (1 mg/mL) in 0.1 M phosphate buffer containing 3.3 mM $MgCl_2$ and 1 mM β-NADPH at 37° C. for 2 hrs. In the first control, 10 µM YM-08 was incubated with 1 mg/mL of boiled microsomes (100° C. for 5 min) in the same buffer. In the second control, neither YM-08 nor microsomes were added to the buffer. After 2 hrs incubation, reactions were terminated by adding one-volume of ice-cold acetonitrile. The supernatants were collected after precipitating protein via centrifugation at 14,000 rpm for 10 min and then subjected to LC-MS/MS analysis. In the second control, YM-01 or YM-08 (5 µM) was added prior to LC-MS/MS analysis. In the analysis, multiple-reaction monitoring (MRM) mode was employed to identify the potential metabolites. Based on the precursor and fragment ions, the MRM ion transition list of possible metabolites were generated by Metabolite ID software (Applied Biosystems), which accounts for 40 common biotransformation processes. Only the peaks that were detected in the sample but absent in both negative controls were determined to be the metabolites of YM-08. To characterize the metabolites of YM-08, the peaks were selected individually and subjected to MS2 scan to obtain fragments.

Pharmacokinetic Sampling

Female CD-1 mice (25-30 g in body weight) were purchased from Charles River Laboratories (Wilmington, Mass.). Mice were treated with 6 mg/kg YM-08 through the tail-vein injection. The plasma and brain were collected at 0.016, 0.08, 0.16, 0.25, 0.5, 1, 2, 4, 6, 13, 18, 24 and 48 h after drug administration. Whole blood samples were drawn through the cardiac puncture using a heparinized syringe with a 22 gauge needle, followed by centrifugation at 3,000 g for 10 min at 4° C. to obtain plasma. Collected tissues were washed with PBS, immediately frozen using liquid nitrogen, and stored at −80° C. until further analysis. Tissue homogenates were prepared by adding PBS (1:5 w/v, homogenate/PBS) and homogenization for 3 min Compound was extracted from 100 µL of sample by adding 300 µL of acetonitrile containing 50 ng/mL IS, followed by vortexing for 3 min. The supernatant was collected and subjected to LC-MS/MS analysis.

LC/MS/MS Analysis

The separation of YM-08 and internal standard was performed using Agilent 1200 HPLC system (Agilent Technologies, Santa Clara, Calif.) and Zobarx SB-C18 column (2.1×50 mm, 3.5 µm) (Agilent Technologies). YM-08 was dissolved from solid in 30% water, 5% Cremophor, 5% ethanol and 60% phosphate buffered saline. The compounds were eluted with an fixed gradient of 20% solvent A and 80% of solvent B. Solvent A consisted of 0.1% (v/v) glacial acetic acid in water and solvent B consisted of 0.1% (v/v) glacial acetic acid in acetonitrile. After injecting 10 μl of samples into HPLC system, the elution was performed over 2 min at a flow rate of 0.4 ml/min. The YM-08 and MKT-077 eluents were detected using QTRAP 3200 mass spectrometer (Applied Biosystems/MDS Sciex, Foster City, Calif.) equipped with an electrospray ionization source (ESI). The temperature of ESI was set at 650° C. and curtain gas, gas 1, and gas 2 were set to 30, 50, and 50 units, respectively.

A positive voltage at 5500 V was applied through ESI to convert the eluents to ions in the form of MH+. The ions were detected using a MRM mode. The ion transitions from the precursor ion (m/z 368) to the fragment ion (m/z=222) and from the precursor ion (m/z 396) to the fragment ion (m/z=175) were used to detect YM-08 and IS, respectively.

Data for Cancer Activity Screens

| Structure | $IC_{50}/\mu M$ MCF-10A | $IC_{50}/\mu M$ MCF-7 | $IC_{50}/\mu M$ HeLa | $IC_{50}/\mu M$ MDA-MB-231 | $IC_{50}/\mu M$ MEF (C57BL/6) |
|---|---|---|---|---|---|
| [structure 1] | 1.46 ± 0.15 | 1.49 ± 0.22 | 3.29 ± 0.36 | 1.02 ± 0.20 | 14.58 ± 1.17 |
| [structure 2] | 3.06 ± 0.38 | 9.60 ± 2.98 | 12.33 ± 1.21 | 4.40 ± 0.39 | NT |
| [structure 3] | 4.77 ± 0.48 | 5.35 ± 1.54 | 8.47 ± 0.89 | 6.16 ± 1.33 | NT |
| [structure 4] | 2.45 ± 0.26 | 2.31 ± 0.43 | 21.08 ± 3.96 | 3.46 ± 0.39 | NT |

-continued

| Structure | IC$_{50}$/μM MCF-10A | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|---|
| (MeO-benzothiazole, N-Me; thiazolidinone N-Et; pyridinium-CH$_2$Ph Cl$^-$) | 1.74 ± 0.19 | 1.60 ± 0.36 | 3.63 ± 0.32 | 1.43 ± 0.19 | NT |
| (Cl-benzothiazole, N-Me; thiazolidinone N-Et; pyridinium-CH$_2$Ph Cl$^-$) | 0.61 ± 0.09 | 1.37 ± 0.27 | 3.70 ± 0.35 | 0.72 ± 0.18 | 6.46 ± 0.70 |
| (benzothiazole, N-Me; thiazolidinone N-CH$_2$Ph; pyridinium-CH$_2$Ph Cl$^-$) | 1.34 ± 0.16 | 2.15 ± 0.68 | 5.89 ± 0.87 | 1.80 ± 0.34 | NT |
| (6,7-diF-benzothiazole, N-Me; thiazolidinone N-Et; pyridinium-CH$_2$Ph Cl$^-$) | 1.36 ± 0.16 | 2.10 ± 0.43 | 6.00 ± 0.64 | 2.64 ± 0.35 | NT |
| (4-F-benzothiazole, N-Me; thiazolidinone N-Et; thiazolium-CH$_2$Ph Cl$^-$) | 1.07 ± 0.05 | 0.96 ± 0.20 | 2.23 ± 0.28 | 0.40 ± 0.03 | 8.29 ± 0.66 |

| Structure | IC$_{50}$/μM MCF-10A | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|---|
| 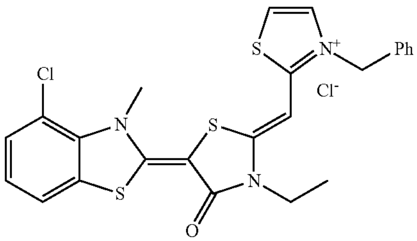 [SMILES: CCn1c(=O)/c(=C2\Sc3cccc(Cl)c3N2C)s/c1=C\c1scc[n+]1Cc1ccccc1 ; [Cl-]] | 1.14 ± 0.15 | 0.83 ± 0.19 | 1.87 ± 0.23 | 0.41 ± 0.02 | 6.96 ± 0.63 |
| 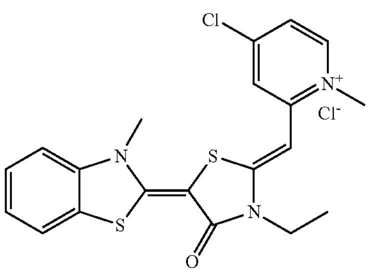 [SMILES: CCn1c(=O)/c(=C2\Sc3ccccc3N2C)s/c1=C\c1cc(Cl)cc[n+]1C ; [Cl-]] | 1.12 ± 0.04 | 2.81 ± 1.01 | N/A | 2.83 ± 0.26 | NT |
| 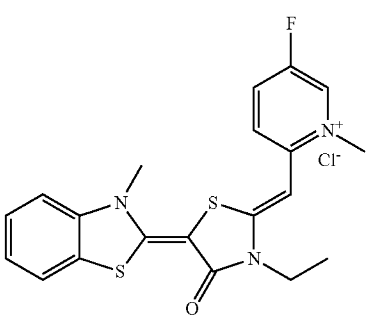 [SMILES: CCn1c(=O)/c(=C2\Sc3ccccc3N2C)s/c1=C\c1ccc(F)c[n+]1C ; [Cl-]] | 5.34 ± 0.26 | >30 | 14.96 ± 0.98 | 7.82 ± 0.78 | NT |
| | NT | 1.39 ± 0.24 | 7.60 ± 0.99 | 1.99 ± 0.33 | NT |
| | NT | 0.83 ± 0.23 | 4.32 ± 0.43 | 0.62 ± 0.10 | NT |

-continued

| Structure | IC$_{50}$/μM MCF-10A | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|---|
| (structure) | NT | 0.71 ± 0.22 | 0.83 ± 0.20 | 0.39 ± 0.03 | 23.89 ± 1.28 |
| (structure) | NT | 1.05 ± 0.79 | 3.93 ± 0.51 | 0.55 ± 0.05 | >30 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| (structure) | | | >30 | >50 |
| (structure) | | | 0.38 ± 0.03 | |
| (structure) | | | 3.07 ± 0.73 | >50 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | >50 |
| | | | 16.21 ± 1.12 | >50 |
| | | | | >50 |
| | | | >30 | >50 |
| | | | 9.18 ± 1.04 | |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 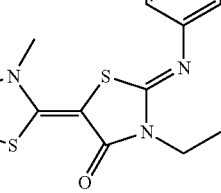 | | | 17.72 ± 2.85 | >50 |
| 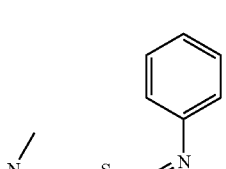 | | | >30 | >50 |
| 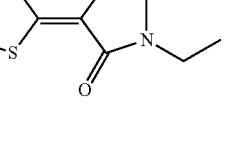 | | | 0.71 ± 0.12 | |
| 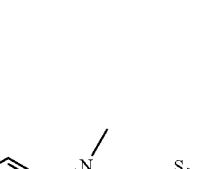 | | | 1.4 ± 0.1 | |
| 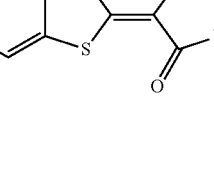 | | | 4.4 ± 0.5 | >50 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 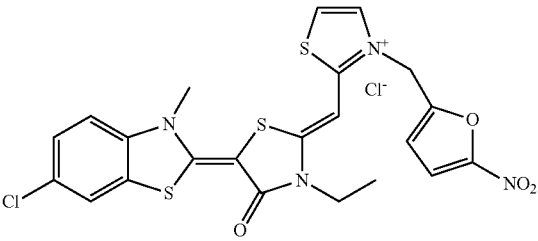 [SMILES: CCn1c(=O)/c(=C2\Sc3cc(Cl)ccc3N2C)s/c1=C\c1scc[n+]1Cc1ccc([N+](=O)[O-])o1 ; [Cl-]] | | | | >30 |
| 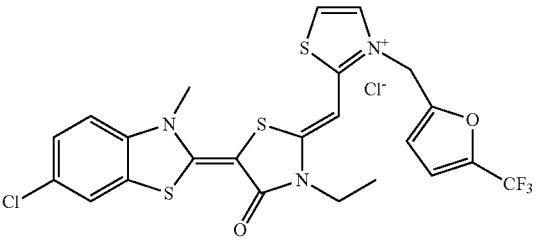 [SMILES: CCn1c(=O)/c(=C2\Sc3cc(Cl)ccc3N2C)s/c1=C\c1scc[n+]1Cc1ccc(C(F)(F)F)o1 ; [Cl-]] | | | | 0.12 ± 0.02 |
| 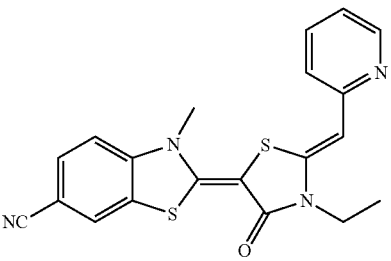 [SMILES: CCn1c(=O)/c(=C2\Sc3cc(C#N)ccc3N2C)s/c1=C\c1ccccn1] | | | | 22.31 ± 4.61 |
| 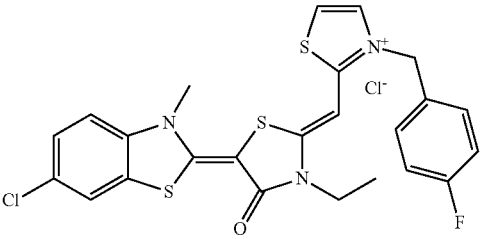 [SMILES: CCn1c(=O)/c(=C2\Sc3cc(Cl)ccc3N2C)s/c1=C\c1scc[n+]1Cc1ccc(F)cc1 ; [Cl-]] | | | | 1.07 ± 0.19 |
| 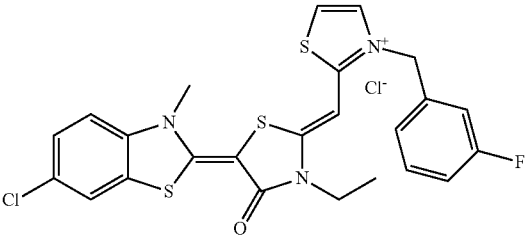 [SMILES: CCn1c(=O)/c(=C2\Sc3cc(Cl)ccc3N2C)s/c1=C\c1scc[n+]1Cc1cccc(F)c1 ; [Cl-]] | | | | 1.01 ± 0.16 |
| 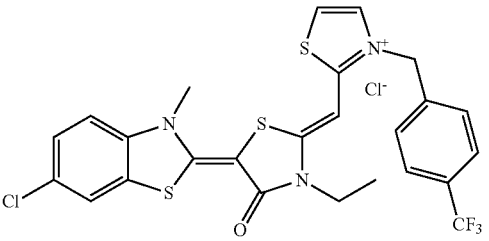 [SMILES: CCn1c(=O)/c(=C2\Sc3cc(Cl)ccc3N2C)s/c1=C\c1scc[n+]1Cc1ccc(C(F)(F)F)cc1 ; [Cl-]] | | | | 1.20 ± 0.15 |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 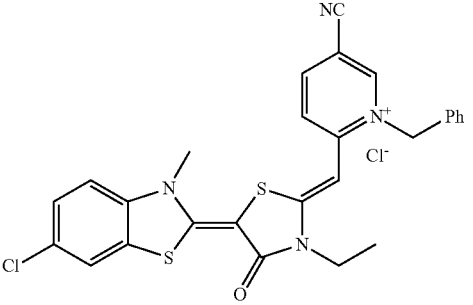 [SMILES: CCn1c(=O)/c(=C2\Sc3cc(Cl)ccc3N2C)s/c1=C\c1ccc(C#N)c[n+]1Cc1ccccc1 ; [Cl-]] | | | 1.92 ± 0.16 | >50 |
| 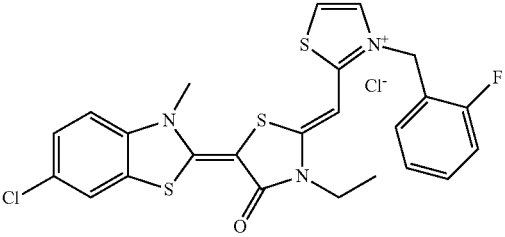 [SMILES: CCn1c(=O)/c(=C2\Sc3cc(Cl)ccc3N2C)s/c1=C\c1scc[n+]1Cc1ccccc1F ; [Cl-]] | | | 0.29 ± 0.04 | |
| 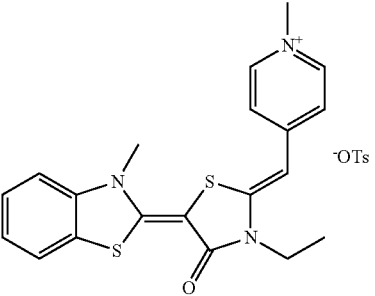 [SMILES: CCn1c(=O)/c(=C2\Sc3ccccc3N2C)s/c1=C\c1cc[n+](C)cc1 ; "-OTs"] | | | 3.01 ± 0.26 | >50 |
| 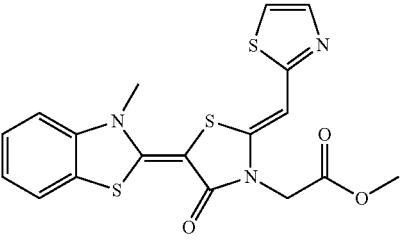 [SMILES: COC(=O)Cn1c(=O)/c(=C2\Sc3ccccc3N2C)s/c1=C\c1nccs1] | | | >30 | >50 |
| 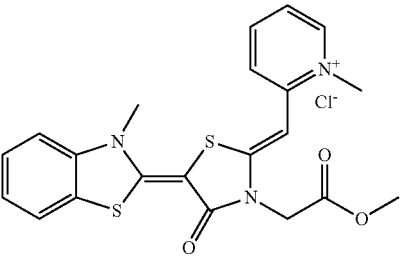 [SMILES: COC(=O)Cn1c(=O)/c(=C2\Sc3ccccc3N2C)s/c1=C\c1cccc[n+]1C ; [Cl-]] | | | 16.51 ± 1.05 | >50 |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 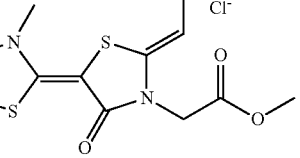 | | | 0.87 ± 0.14 | >50 |
| 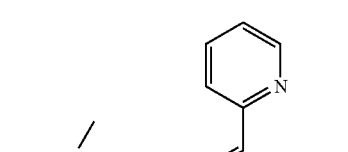 | | | >30 | >50 |
| 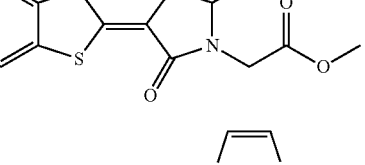 | | | >30 | >50 |
| 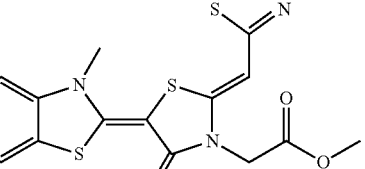 | 0.8 ± 0.1 | | 2.2 ± 0.2 | >30 |
| 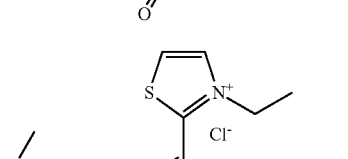 | 0.6 ± 0.04 | | 0.5 ± 0.1 | 6.8 ± 0.4 |
| 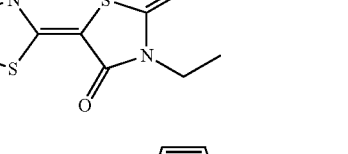 | 0.9 ± 0.3 | | 8.3 ± 1.1 | >30 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 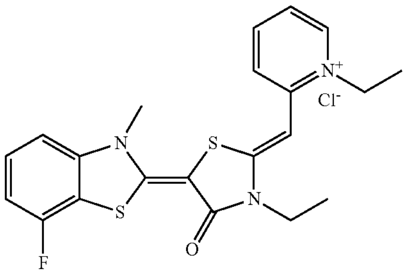 [SMILES: CCn1c(=O)/c(=C2\Sc3c(F)cccc3N2C)s/c1=C\c1cccc[n+]1CC ; [Cl-]] | 0.8 ± 0.1 | | 2.8 ± 0.2 | 27.1 ± 3.0 |
| 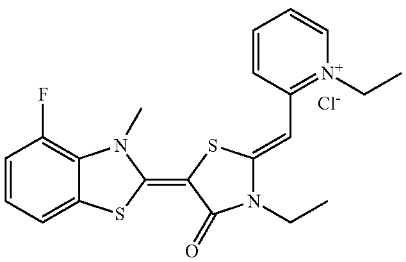 [SMILES: CCn1c(=O)/c(=C2\Sc3cccc(F)c3N2C)s/c1=C\c1cccc[n+]1CC ; [Cl-]] | 1.0 ± 0.3 | | 3.8 ± 0.2 | >30 |
| 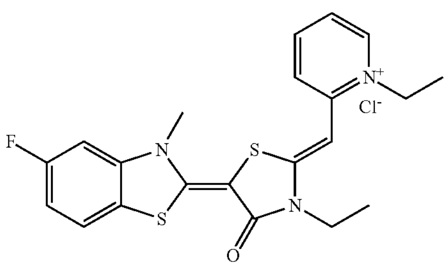 [SMILES: CCn1c(=O)/c(=C2\Sc3ccc(F)cc3N2C)s/c1=C\c1cccc[n+]1CC ; [Cl-]] | 2.4 ± 0.6 | | 13.3 ± 0.7 | >30 |
| 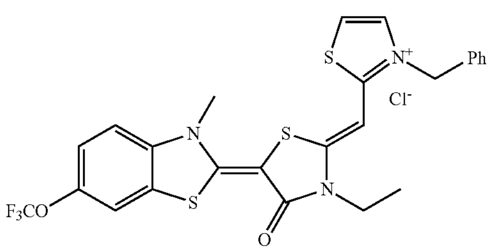 [SMILES: CCn1c(=O)/c(=C2\Sc3cc(OC(F)(F)F)ccc3N2C)s/c1=C\c1scc[n+]1Cc1ccccc1 ; [Cl-]] | 0.4 ± 0.04 | | 0.8 ± 0.1 | 1.2 ± 0.1 |
| | | | >20 | |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | >20 |
| | | | | 2.0 ± 0.2 |
| | | | | >20 |
| | | | | >20 |
| | | | | >20 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | >20 |
| | | | | >20 |
| | | | | >20 |
| | | | | 0.34 ± 0.03 |
| | | | | >20 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | >20 | |
| | | | 0.96 ± 0.07 | |
| | | | 0.24 ± 0.03 | |
| | | | 9.0 ± 1.7 | |
| | | | >20 | |
| | | | 0.51 ± 0.03 | |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | 1.2 ± 0.14 | |
| | | | 0.15 ± 0.01 | |
| | | | 2.9 ± 0.3 | |
| | | | 0.13 ± 0.01 | |
| | | | 0.40 ± 0.04 | |
| | | | 0.076 ± 0.01 | |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | 0.20 ± 0.02 | |
| | | | >20 | |
| | | | 0.22 ± 0.02 | |
| | | | >20 | |
| | | | >20 | |
| | | | 2.1 ± 0.4 | |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 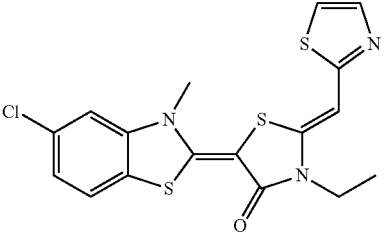 [SMILES: CCn1c(=O)/c(=C2\Sc3ccc(Cl)cc3N2C)s/c1=C\c1nccs1] | | | | 1.5 ± 0.3 |
| 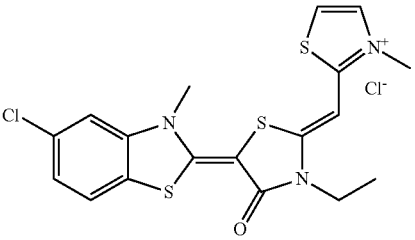 [SMILES: CCn1c(=O)/c(=C2\Sc3ccc(Cl)cc3N2C)s/c1=C\c1scc[n+]1C ; [Cl-]] | | | | 3.1 ± 0.4 |
| 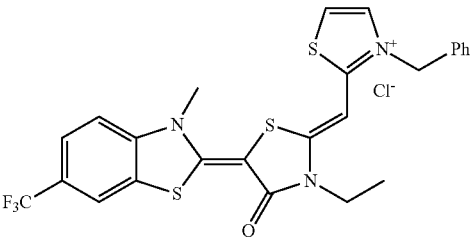 [SMILES: CCn1c(=O)/c(=C2\Sc3cc(C(F)(F)F)ccc3N2C)s/c1=C\c1scc[n+]1Cc1ccccc1 ; [Cl-]] | | | | 0.36 ± 0.03 |
| 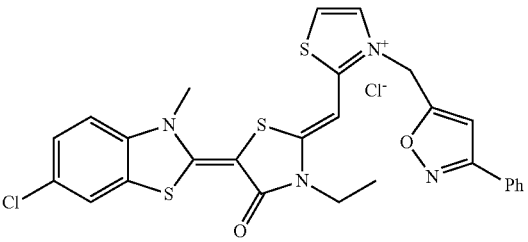 [SMILES: CCn1c(=O)/c(=C2\Sc3cc(Cl)ccc3N2C)s/c1=C\c1scc[n+]1Cc1cc(-c2ccccc2)no1 ; [Cl-]] | | | | 0.17 ± 0.01 |
| 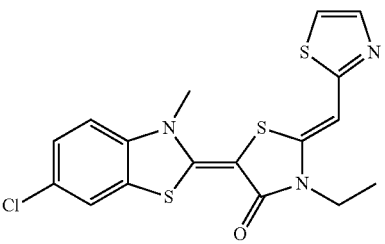 [SMILES: CCn1c(=O)/c(=C2\Sc3cc(Cl)ccc3N2C)s/c1=C\c1nccs1] | | | | 2.3 ± 0.6 |
| 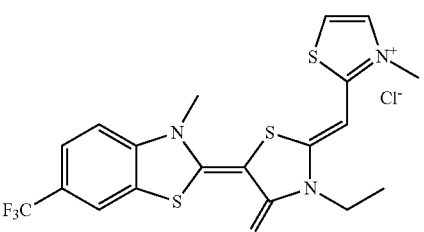 | | | | 8.5 ± 1.0 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | 5.6 ± 0.6 |
| | | | | 4.2 ± 0.6 |
| | | | | 0.24 ± 0.01 |
| | | | | 2.6 ± 0.5 |
| | | | | 11.71 ± 2.3 |
| | | | | 2.7 ± 0.6 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | 0.34 ± 0.03 |
| | | | | 0.30 ± 0.02 |
| | | | | 1.6 ± 0.2 |
| | | | | 0.11 ± 0.01 |
| | | | | 0.72 ± 0.08 |
| | | | | 0.74 ± 0.07 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | 0.16 ± 0.03 |
| | | | | 0.14 ± 0.02 |
| | | | | 0.25 ± 0.03 |
| | | | | 0.21 ± 0.03 |
| | | | | 0.97 ± 0.10 |
| | | | | 3.05 ± 0.42 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 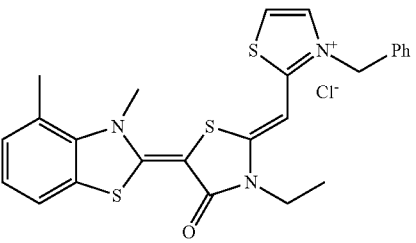 | | | | 0.21 ± 0.04 |
| 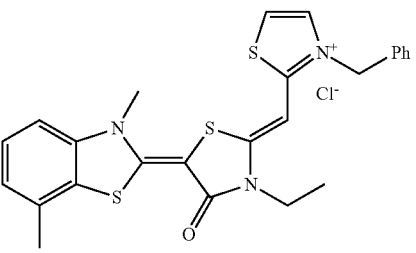 [SMILES: CCn1c(=O)/c(=C2\Sc3c(C)cccc3N2C)s/c1=C\c1scc[n+]1Cc1ccccc1 ; [Cl-]] | | | | 0.25 ± 0.03 |
| 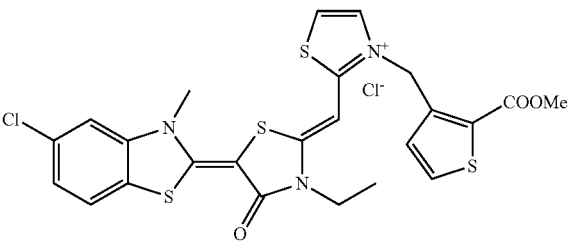 [SMILES: CCn1c(=O)/c(=C2\Sc3ccc(Cl)cc3N2C)s/c1=C\c1scc[n+]1Cc1ccsc1C(=O)OC ; [Cl-]] | | | | 0.16 ± 0.02 |
| 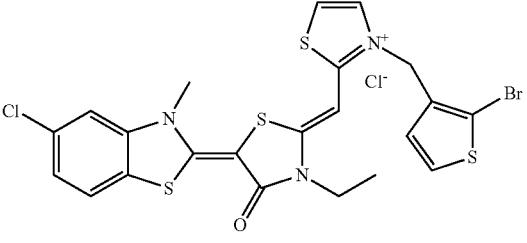 [SMILES: CCn1c(=O)/c(=C2\Sc3ccc(Cl)cc3N2C)s/c1=C\c1scc[n+]1Cc1ccsc1Br ; [Cl-]] | | | | 0.24 ± 0.03 |
| 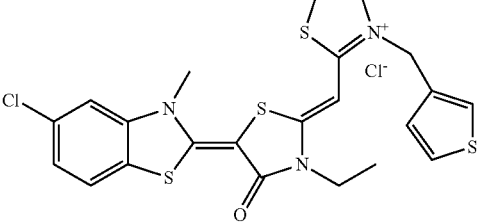 | | | | 0.44 ± 0.05 |
| 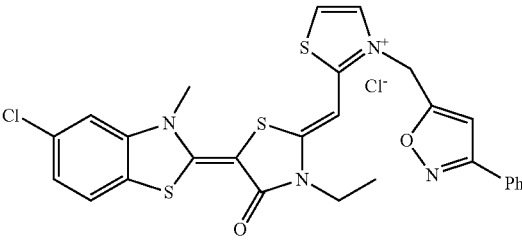 [SMILES: CCn1c(=O)/c(=C2\Sc3ccc(Cl)cc3N2C)s/c1=C\c1scc[n+]1Cc1cc(-c2ccccc2)no1 ; [Cl-]] | | | | 0.50 ± 0.04 |

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| | | | | 0.078 ± 0.01 |
| | | | | 0.041 ± 0.006 |
| | | | | 1.05 ± 0.09 |
| | | | | 1.33 ± 0.11 |
| | | | | 0.81 ± 0.06 |
| | | | | 0.12 ± 0.009 |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 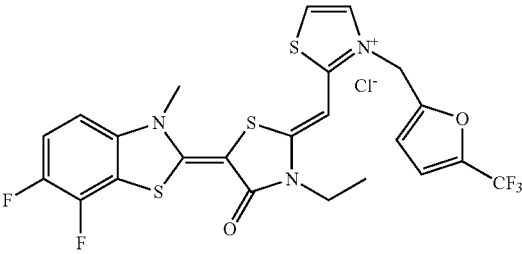 [SMILES: CCn1c(=O)/c(=C2\Sc3c(ccc(F)c3F)N2C)s/c1=C\c1scc[n+]1Cc1ccc(C(F)(F)F)o1 ; [Cl-]] | | | | 0.51 ± 0.05 |
| 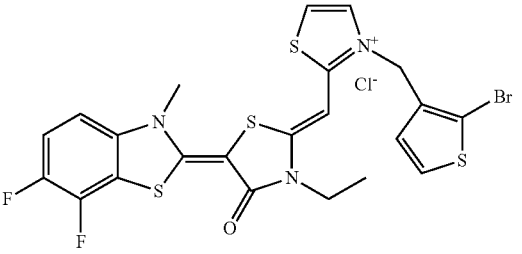 [SMILES: CCn1c(=O)/c(=C2\Sc3c(ccc(F)c3F)N2C)s/c1=C\c1scc[n+]1Cc1ccsc1Br ; [Cl-]] | | | | 0.48 ± 0.06 |
| 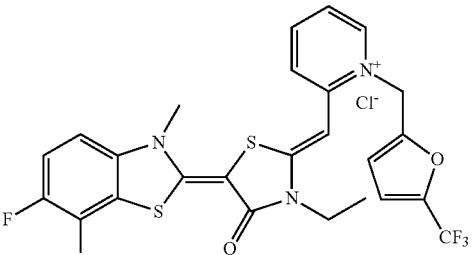 | | | | 0.92 ± 0.10 |
| 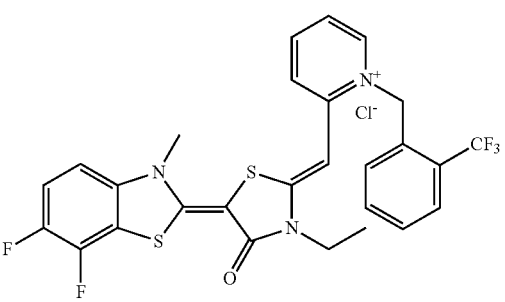 [SMILES: CCn1c(=O)/c(=C2\Sc3c(ccc(F)c3F)N2C)s/c1=C\c1cccc[n+]1Cc1ccccc1C(F)(F)F ; [Cl-]] | | | | 0.38 ± 0.07 |
| 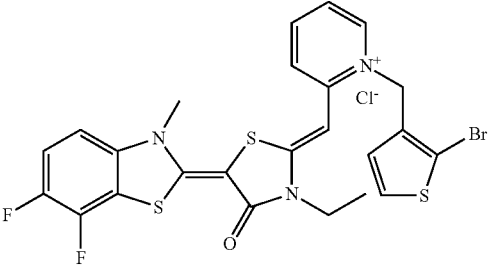 [SMILES: CCn1c(=O)/c(=C2\Sc3c(ccc(F)c3F)N2C)s/c1=C\c1cccc[n+]1Cc1ccsc1Br ; [Cl-]] | | | | 0.92 ± 0.17 |

-continued
| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| 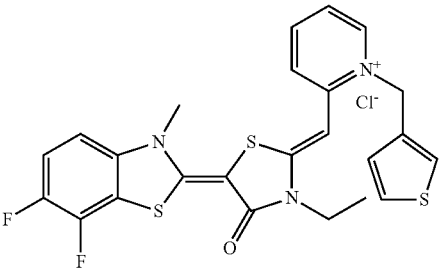 [SMILES: CCn1c(=O)/c(=C2\Sc3c(ccc(F)c3F)N2C)s/c1=C\c1cccc[n+]1Cc1ccsc1 ; [Cl-]] | | | | 2.09 ± 0.31 |
| 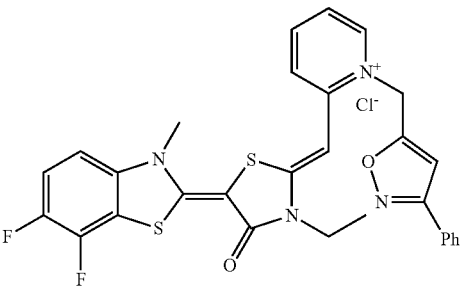 [SMILES: CCn1c(=O)/c(=C2\Sc3c(ccc(F)c3F)N2C)s/c1=C\c1cccc[n+]1Cc1cc(-c2ccccc2)no1 ; [Cl-]] | | | | 1.33 ± 0.20 |
| 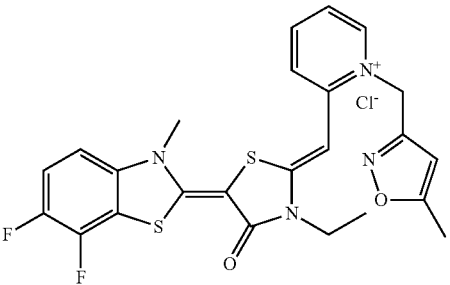 [SMILES: CCn1c(=O)/c(=C2\Sc3c(ccc(F)c3F)N2C)s/c1=C\c1cccc[n+]1Cc1cc(C)on1 ; [Cl-]] | | | | 3.72 ± 0.41 |
| 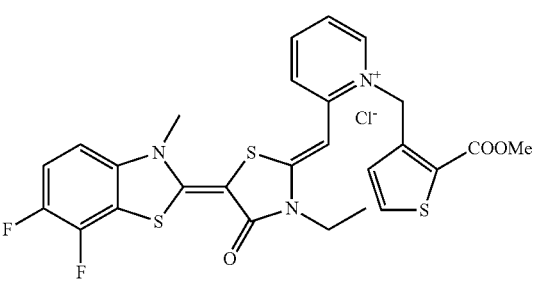 [SMILES: CCn1c(=O)/c(=C2\Sc3c(ccc(F)c3F)N2C)s/c1=C\c1cccc[n+]1Cc1ccsc1C(=O)OC ; [Cl-]] | | | | 1.95 ± 0.27 |
| 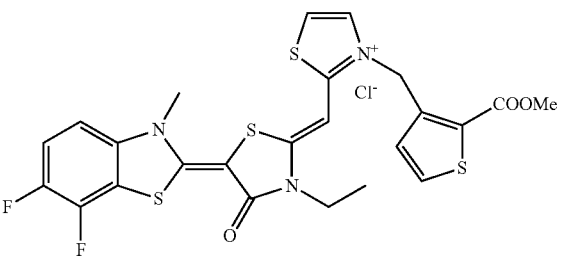 [SMILES: CCn1c(=O)/c(=C2\Sc3c(ccc(F)c3F)N2C)s/c1=C\c1scc[n+]1Cc1ccsc1C(=O)OC ; [Cl-]] | | | | 0.21 ± 0.03 |

-continued

| Structure | IC$_{50}$/μM MCF-7 | IC$_{50}$/μM HeLa | IC$_{50}$/μM MDA-MB-231 | IC$_{50}$/μM MEF (C57BL/6) |
|---|---|---|---|---|
| (structure with 6-Cl benzothiazole, cyclopropyl, benzyl thiazolium) | | | | 0.56 ± 0.08 |
| (structure with 6-F benzothiazole, cyclopropyl, benzyl thiazolium) | | | | 0.76 ± 0.08 |
| (structure with F$_3$CO-benzothiazole, ethyl, benzyl thiazolium) | | | | 1.25 ± 0.13 |
| (structure with MeO$_2$S-benzothiazole, ethyl, benzyl thiazolium) | | | | >20 |

Data for Tau Activity Screens

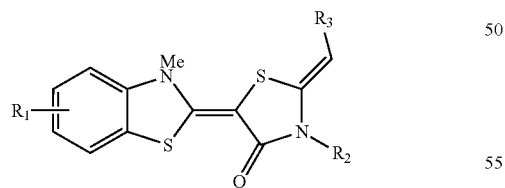

| | | R$_1$ | R$_2$ | R$_3$ | HeLa Tau Degradation at 10 μM | MEF IC$_{50}$ μM | t$_{1/2}$ min |
|---|---|---|---|---|---|---|---|
| 1 | (YM-08) | H | ethyl | 2-pyridinyl | − | 4.20 ± 0.24 | <3 |
| 2 | (JG-27) | 3-F | ethyl | 2-pyridinyl | − | 14.60 ± 1.04 | 24.74 |
| 3 | (JG-19) | 4-F | ethyl | 2-pyridinyl | − | 2.95 ± 0.19 | 30.76 |
| 4 | (JG-10) | 5-F | ethyl | 2-pyridinyl | ++ | 7.61 ± 0.63 | 4.26 |

|  | R₁ | R₂ | R₃ | HeLa Tau Degradation at 10 μM | MEF IC$_{50}$ μM | t$_{1/2}$ min |
|---|---|---|---|---|---|---|
| 5 (JG-28) | 6-F | ethyl | 2-pyridinyl | − | 8.62 ± 0.48 | 8.25 |
| 6 | 3-Cl | ethyl | 2-pyridinyl | + | NT | NT |
| 7 | 4-Cl | ethyl | 2-pyridinyl | + | NT | NT |
| 8 (JG-47) | 5-Cl | ethyl | 2-pyridinyl | ++ | 12.20 ± 1.44 | 19.07 |
| 9 | 6-Cl | ethyl | 2-pyridinyl | + | NT | NT |
| 10 | 5-OMe | ethyl | 2-pyridinyl | − | NT | 7.78 |
| 11 (JG-48) | 5-CF₃ | ethyl | 2-pyridinyl | ++ | 6.21 ± 0.60 | 17.22 |
| 12 | 5-SO₂Me | ethyl | 2-pyridinyl | + | NT | 17.05 |
| 13 | 4,5-diF | ethyl | 2-pyridinyl | − | NT | 3.44 |
| 14 | H | allyl | 2-pyridinyl | − | NT | NT |
| 15 | H | benzyl | 2-pyridinyl | − | NT | NT |
| 16 | H | ethyl | 4-pyridinyl | ++ | NT | NT |
| 17 (JG-13) | 5-F | ethyl | 4-pyridinyl | ++ | 3.63 ± 0.15 | NT |
| 18 | H | ethyl | 2-thiazolyl | − | NT | NT |

Detailed Synthesis Information

Compounds MKT-077 (1-ethyl-2-((Z)-((E)-3-ethyl-5-(3-methylbenzo[d]thiazol-2(3H)-ylidene)-4-oxothiazolidin-2-ylidene)methyl)pyridin-1-ium), YM-02 ((E)-3-ethyl-5-(3-methylbenzo[d]thiazol-2(3H)-ylidene)-2-thioxothiazolidin-4-one), YM-03 ((E)-3-ethyl-5-(3-methylbenzo[d]thiazol-2 (3H)-ylidene)-2-(methylthio)-4-oxo-4,5-dihydrothiazol-3-ium), YM-04 ((Z)-2-((3-ethyl-4-oxothiazolidin-2-ylidene)methyl)-1-methylpyridin-1-ium) and YM-07 ((Z)-3-ethyl-2-(pyridin-2-ylmethylene)thiazolidin-4-one) were synthesized as previously reported in Nishigaki et al., JP 2004359801. Characterization by ¹H NMR and mass spectrometry confirmed the reported values.

2-((Z)-((E)-3-ethyl-5-(3-methylbenzo[d]thiazol-2(3H)-ylidene)-4-oxothiazolidin-2-ylidene)methyl)-1-methylpyridin-1-ium (YM-01). ¹H d$_6$-DMSO 8.67 (1H, d, J=6.3 Hz), 8.26 (1H, t, J=8.2 Hz), 8.04 (1H, d, J=8.6 Hz), 7.87 (1H, d, J=7.8 Hz), 7.61 (1H, d, J=8.2 Hz), 7.49 (1H, t, J=7.4 Hz), 7.42 (1H, t, J=7.4 Hz), 7.30 (1H, t, J=7.4 Hz), 5.96 (1H, t), 4.14 (3H, s), 4.10, (2H, q, J=7.4, 6.7 Hz), 4.04 (3H, s), 1.26 (3H, t, J=6.7 Hz). ¹³C d$_6$-DMSO 163.80, 154.42, 150.60, 150.51, 145.33, 142.67, 140.33, 127.01, 125.61, 123.53, 122.80, 122.06, 118.69, 111.72, 84.19, 78.26, 45.18, 38.23, 34.48, 11.87. MS (ESI): calculated for $C_{20}H_{20}N_3OS_2^+$[M-Cl-]+m/z 382.1. found 382.1. Purity: >95% (determined by ¹H NMR).

(2Z,5E)-3-ethyl-5-(3-methylbenzo[d]thiazol-2(3H)-ylidene)-2-(pyridin-2-ylmethylene)thiazolidin-4-one (YM-08). ¹H NMR (600 MHz, DMSO-d$_6$): δ 8.53 (1H, d, J=4.2 Hz), 7.65 (1H, d, J=7.8 Hz), 7.61 (1H, t, J=7.8 Hz), 7.35 (1H, t, J=7.8 Hz), 7.31 (1H, d, J=7.8 Hz), 7.22 (1H, d, J=7.8 Hz), 7.14 (1H, t, J=7.8 Hz), 6.93 (1H, t, J=6.0 Hz), 6.16 (1H, s), 3.94 (3H, s), 3.89 (2H, q, J=7.2 Hz), 1.20 (3H, t, 7.2 Hz); ¹³C NMR (150 MHz, DMSO-d$_6$): δ 165.08, 155.92, 149.81, 147.41, 140.90, 140.18, 135.78, 126.40, 125.87, 122.38, 121.94, 121.44, 117.32, 110.41, 93.44, 84.10, 37.14, 34.24, 12.09.; ESI-MS: m/z calculated for $[C_{19}H_{18}N_3OS_2]^+$368.09. found 368.1 [M+H]+. Purity: >95% (determined by ¹H NMR).

Combination Therapy—Targeting Hsp70 and Hsp90

MCF7 cells were cultured in DMEM with 10% fetal bovine serum (Invitrogen) and 1% penicillin-streptomycin (Invitrogen). The cells were then treated with the Hsp70 inhibitor JG-83 or JG-84 alone or in combination with the Hsp90 inhibitor 1 nM rapamycin or 1 nM 17-AAG. The inhibitory growth information is shown in FIGS. 8 and 9, indicating that the combination of a Hsp70 and Hsp90 inhibitor resulted in decreased IC50 concentrations, compared to the Hsp70 inhibitor alone.

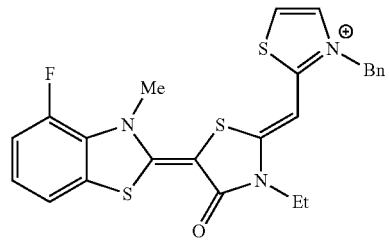

JG-83 and

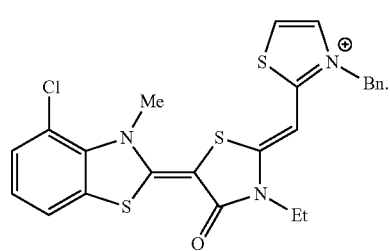

JG-84

To further test if an Hsp70 inhibitor would have synergistic activity with inhibitors of Hsp90 and the proteasome, MDA-MB-231 cells were treated for 24 hrs with combinations of an HSP70 inhibitor and an HSP90 inhibitor and measured cell viability by MTT assays. JG-98 had cytotoxic activity that is synergistic with 17-DMAG and bortezomib. Specifically, the combination index (CI) scores at JG98: 17DMAG (10:1) were CI50=1.09, CI75=0.35, CI90=0.27, CI95=0.2. For the JG98:bortezomib combination (1:1), we observed CI50=0.05, CI75=0.05, CI90<0.02, CI95<0.02. JG98 was also synergistic at ratios of JG98:17DMAG of 1:1 and at ratios of JG98:bortezomib at 100:1. These results show that combinations of an Hsp70 inhibitor and inhibitors of the proteasome and Hsp90 are highly synergistic.

What is claimed:

1. A compound having a structure of formula (I):

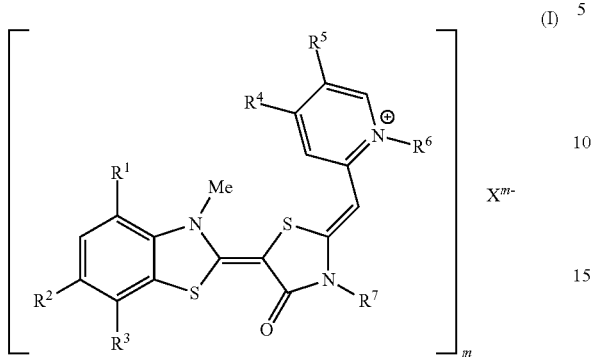

wherein $R^1$, $R^2$, and $R^3$ are each selected from the group consisting of hydrogen, fluoro, chloro, methoxy, methyl, or trifluoromethyl, $R^4$ and $R^5$ are each selected from hydrogen, fluoro, and chloro, $R^6$ is $C_1$-$C_4$ alkyl or $CH_2Ar$;

Ar is aryl;

$R^7$ is ethyl, allyl, or benzyl;

X is a pharmaceutically acceptable anion, and m is 1, 2, or 3;

with the proviso that
(1) if $R^6$ is alkyl, $R^7$ is ethyl, and each of $R^4$ and $R^5$ is hydrogen, then at least one of $R^1$, $R^2$, and $R^3$ is other than hydrogen; and
(2) when each of $R^1$, $R^2$, $R^3$, $R^4$, and $R^5$ is hydrogen, $R^6$ is $CH_2Ar$.

2. A compound having a structure of formula (II):

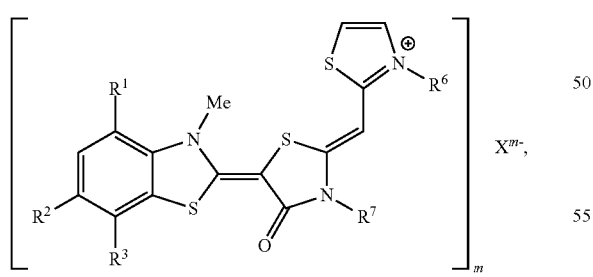

wherein $R^1$, $R^2$, and $R^3$ are each independently selected from the group consisting of hydrogen, chloro, fluoro, methoxy, and trifluoromethyl;

$R^6$ is $CH_2Ar$ or allyl;

Ar is aryl;

$R^7$ is ethyl, allyl, or benzyl; and

X is a pharmaceutically acceptable anion, and m is 1, 2, or 3.

3. A compound having a structure of formula (III):

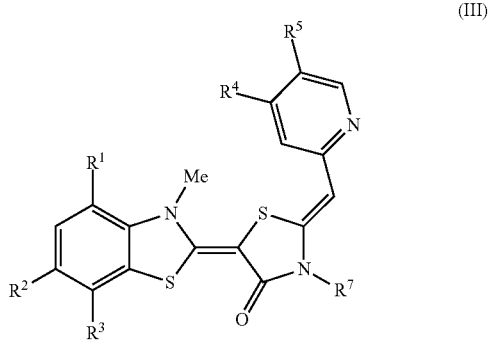

wherein $R^1$, $R^2$, and $R^3$ are each independently selected from the group consisting of hydrogen, chloro, fluoro, methoxy, and trifluoromethyl;

$R^4$ and $R^5$ are each selected from the group consisting of hydrogen, fluoro, and chloro;

$R^7$ is ethyl, allyl, or benzyl;

with the proviso that when $R^7$ is ethyl, at least one of $R^4$ and $R^5$ is other than hydrogen, or a salt thereof.

4. A compound having a structure selected from the group consisting of

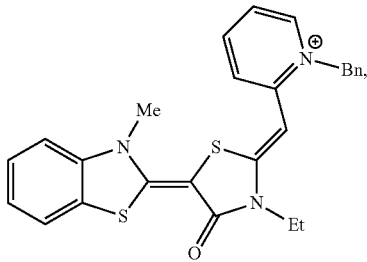

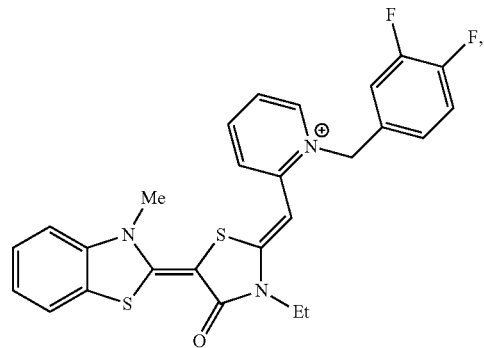

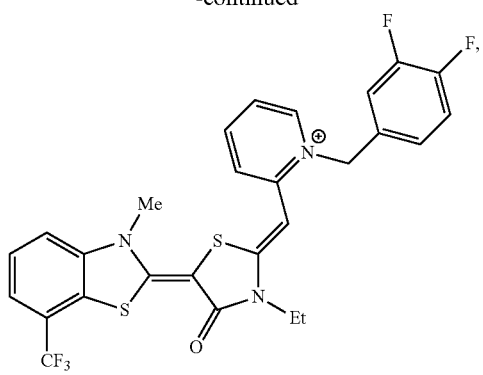
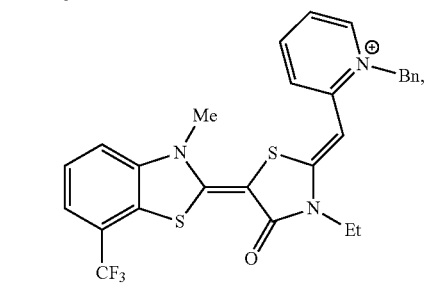
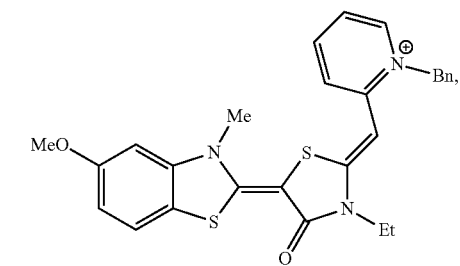
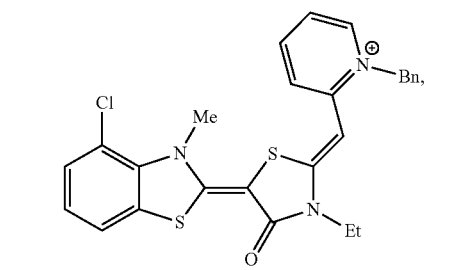
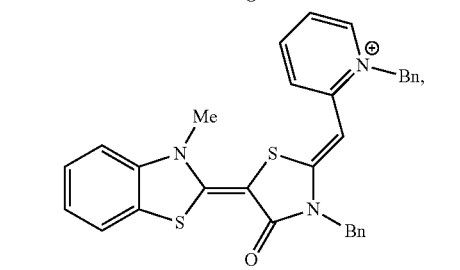
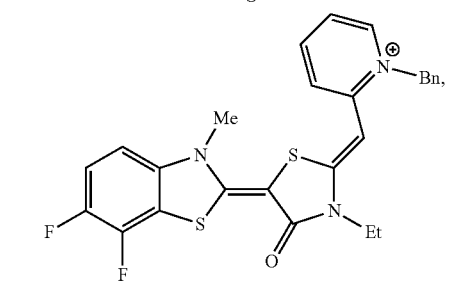
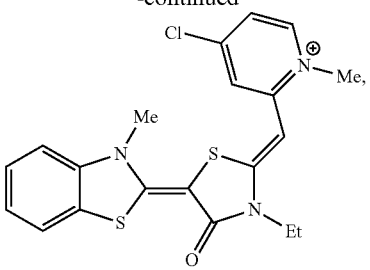
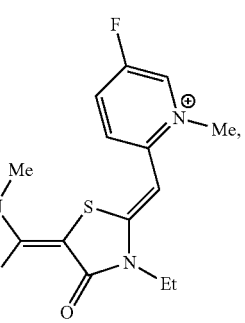
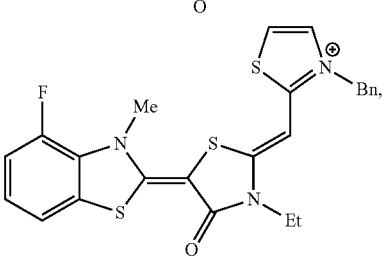
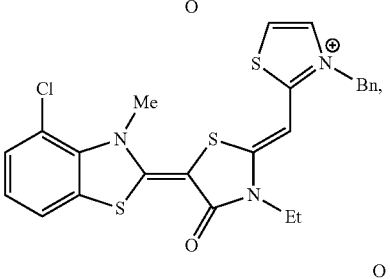
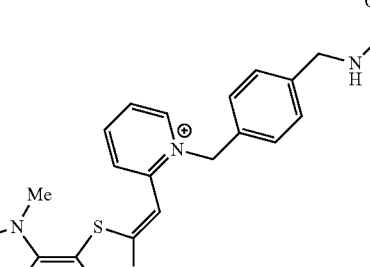
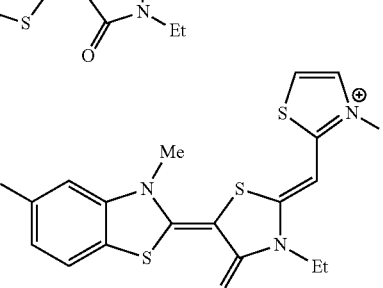

113
-continued

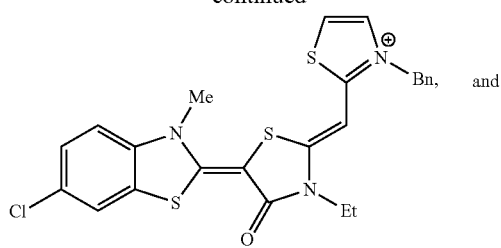
and

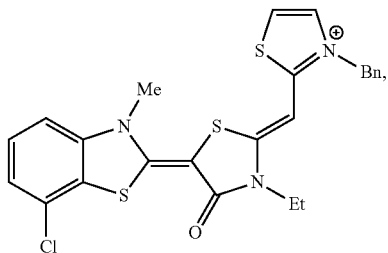

or a compound having a structure

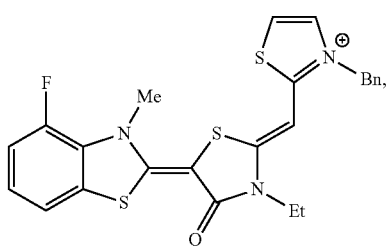

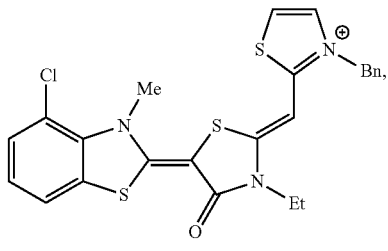

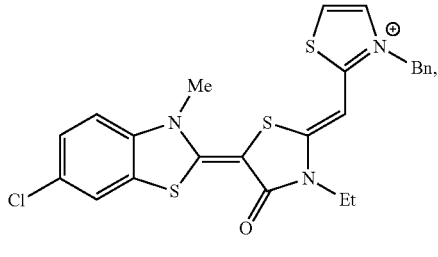

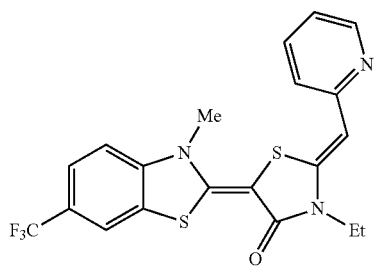
or

114
-continued

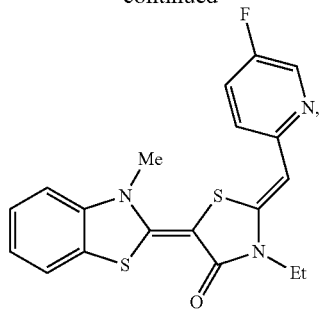

or a salt thereof.

5. A compound having a structure of formula (V):

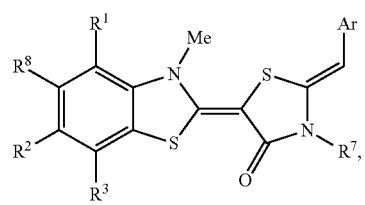

(V)

wherein

Ar is pyridinyl, thiazolyl, pyrazinyl, or pyridinonyl;

$R^1$, $R^2$, $R^3$, and $R^8$ are each selected from the group consisting of hydrogen, fluoro, chloro, methoxy, ethoxy, methyl, ethyl, propyl, isopropyl, trifluromethyl, $SO_2Me$, $NO_2$, trifluromethoxy, CN, ethoxy, propoxy, and isopropoxy, with the proviso that at least one of $R^1$, $R^2$, $R^3$, and $R^8$ is not hydrogen;

$R^7$ is selected from ethyl, allyl, benzyl, methoxy, ethoxy, $C_{3-6}$cycloalkyl, and $(CH_2)_{1-3}CO_2R$, and R is a $C_{1-3}$alkyl;

or a salt thereof.

6. A compound having the structure selected from the group consisting of

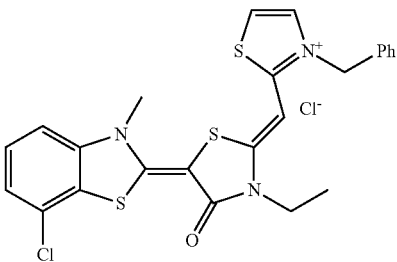

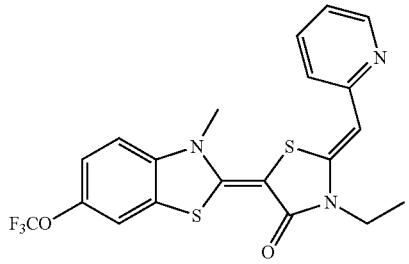

115
-continued
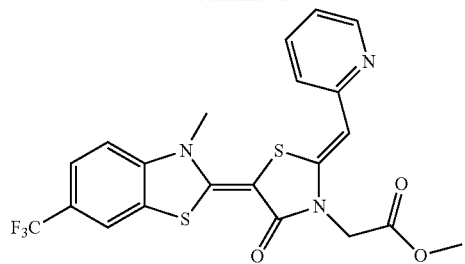
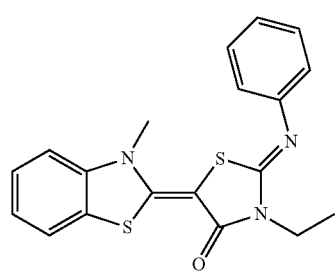
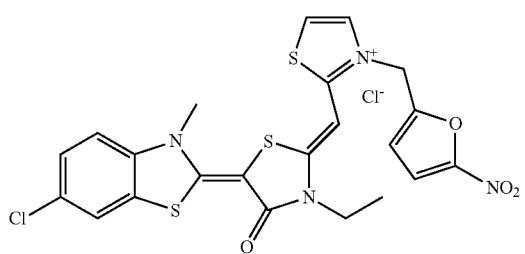
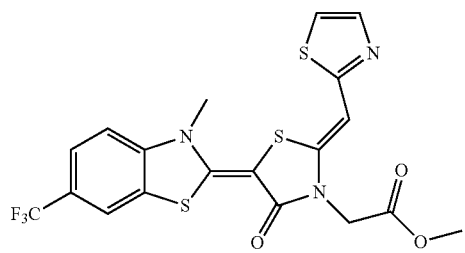
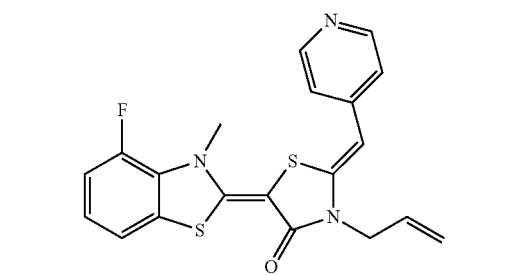
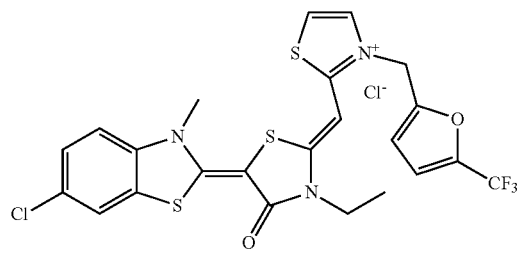
116
-continued
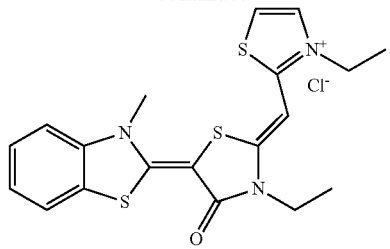
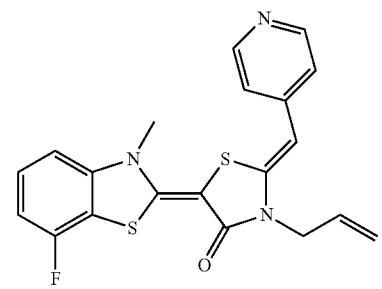
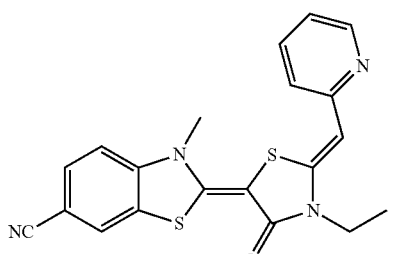
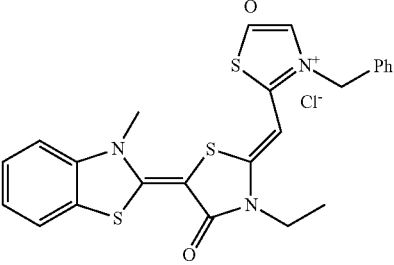
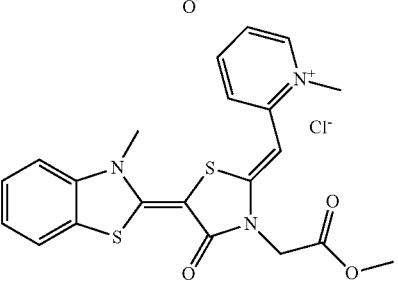
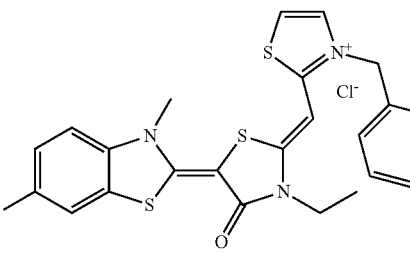

117
-continued
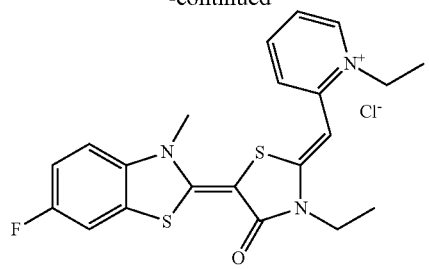
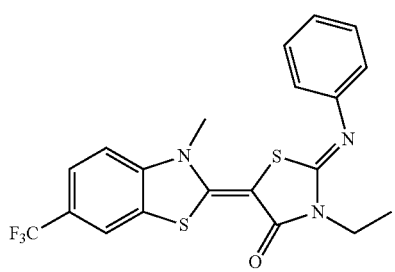
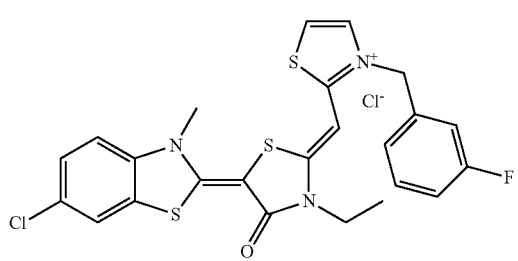
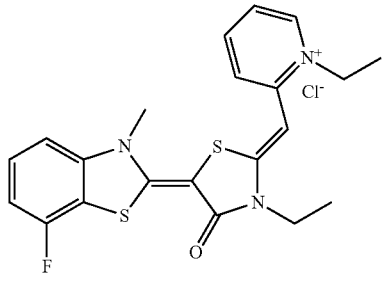
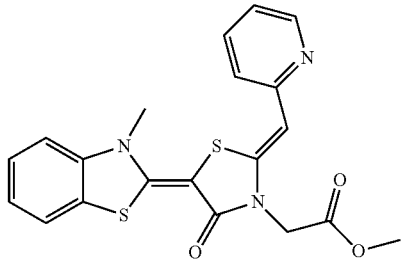
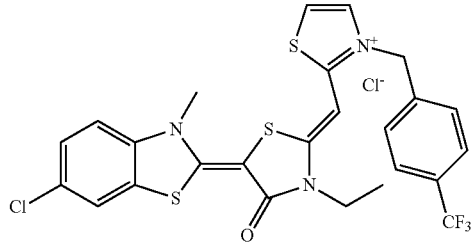
118
-continued
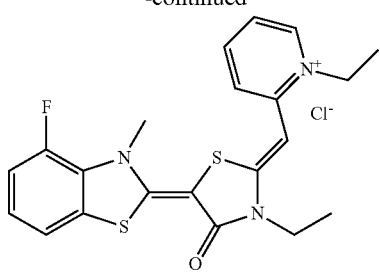
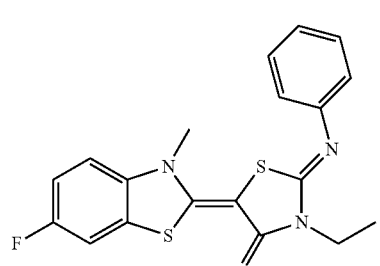
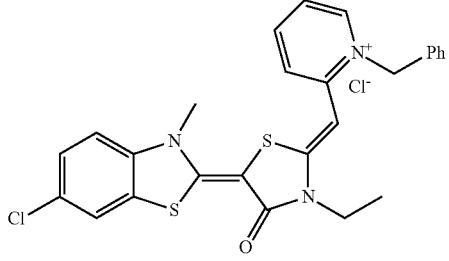
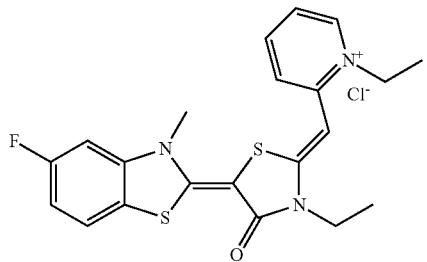
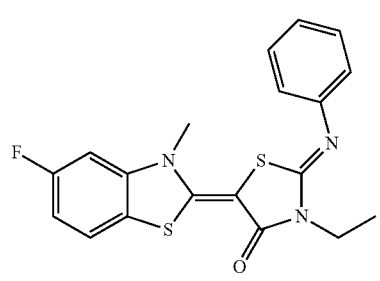
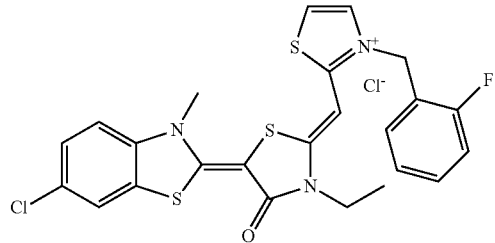

119
-continued
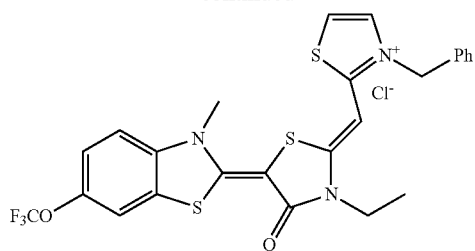
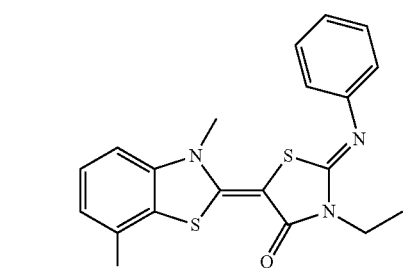
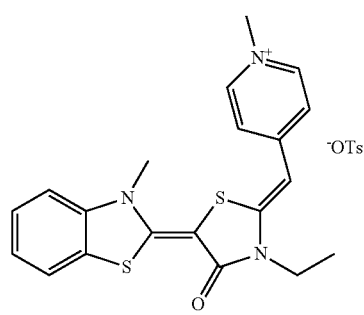
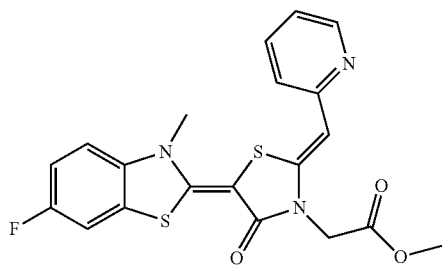
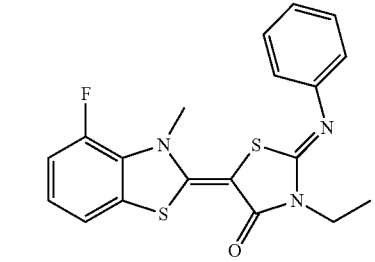
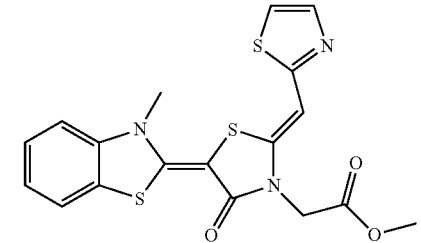
120
-continued
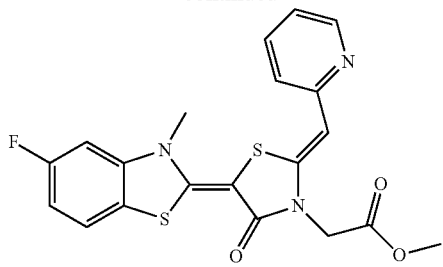
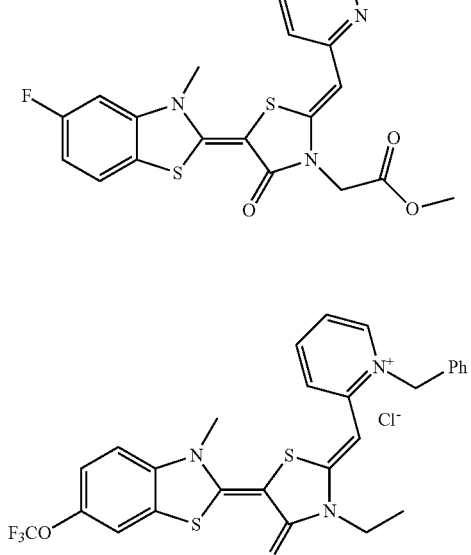
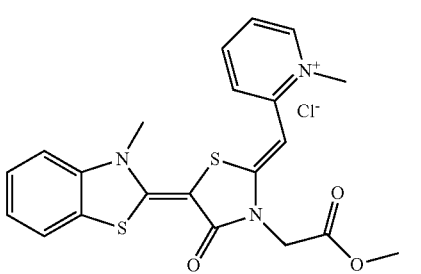
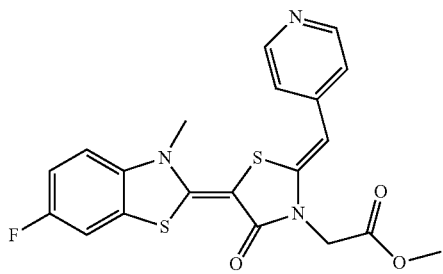
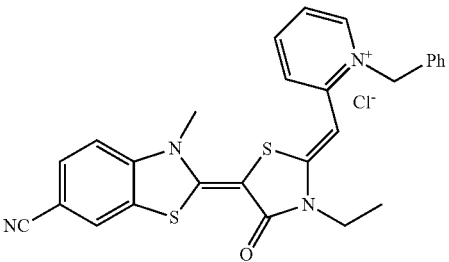
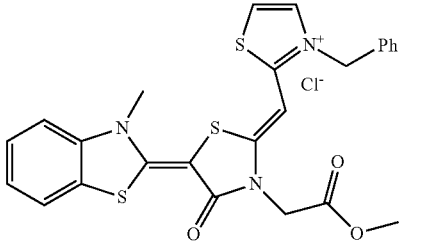

121
-continued
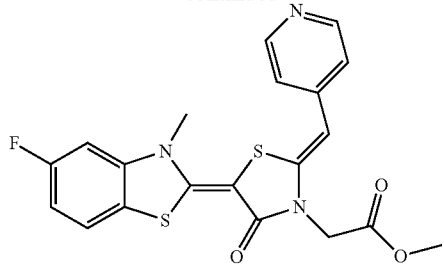
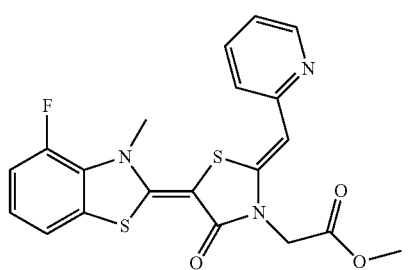
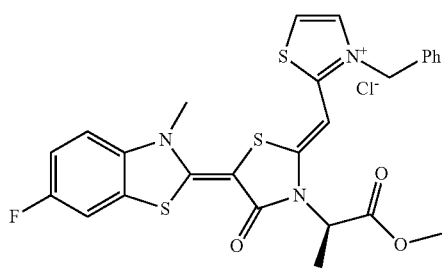
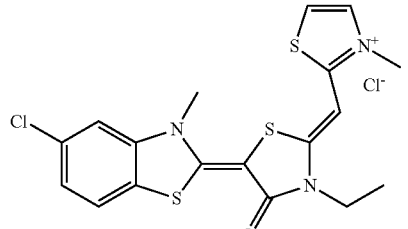
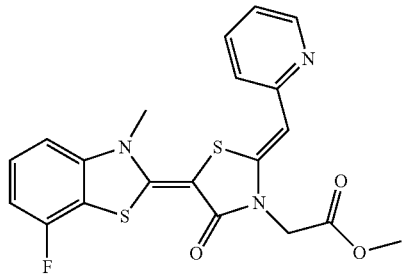
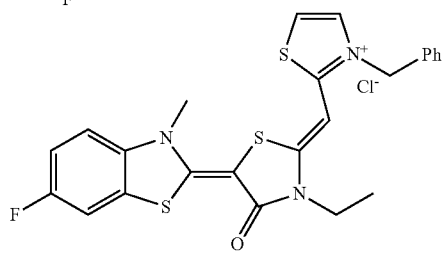
122
-continued
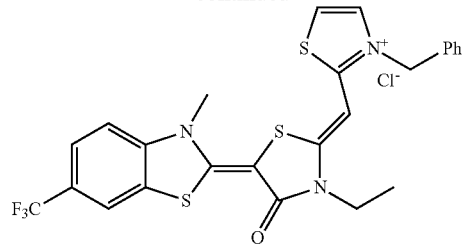
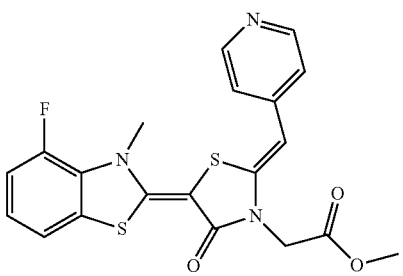
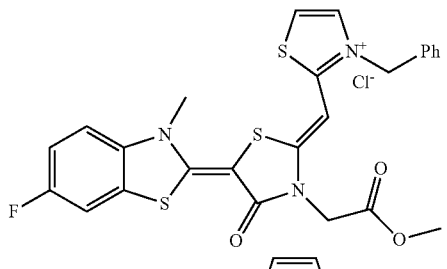
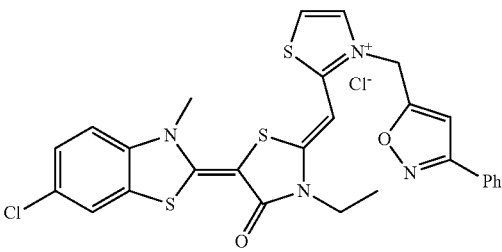
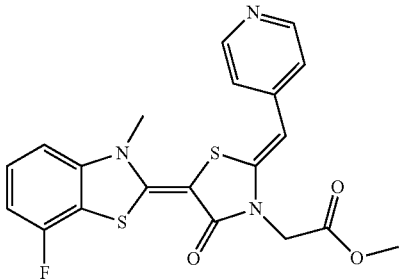
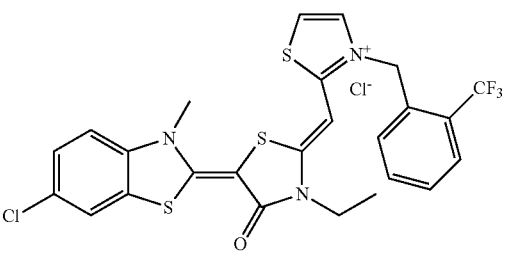

123
-continued
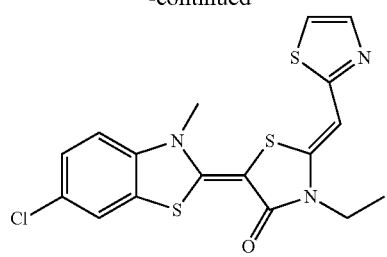
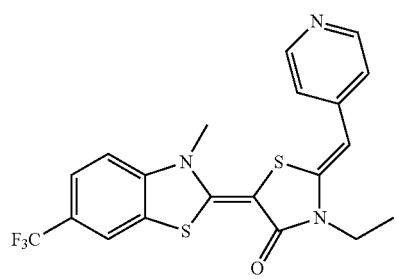
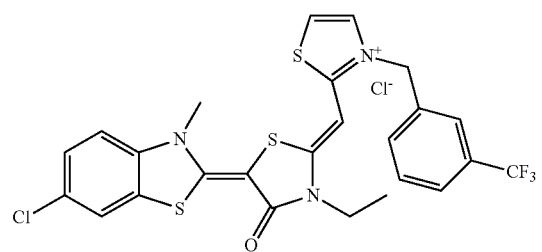
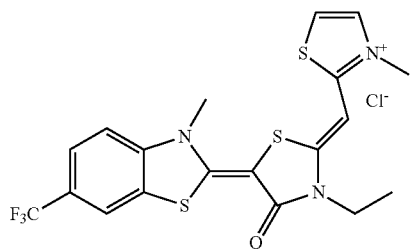
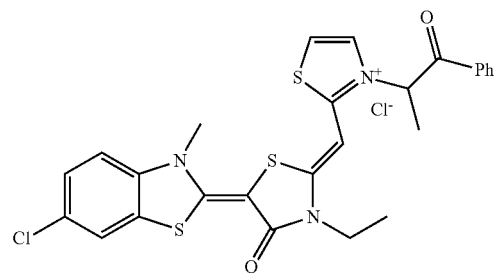
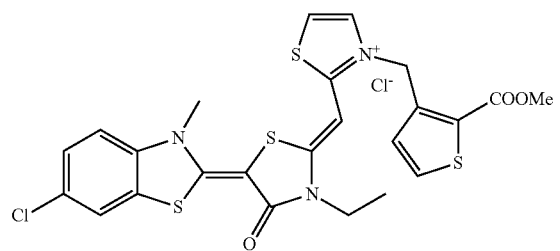
124
-continued
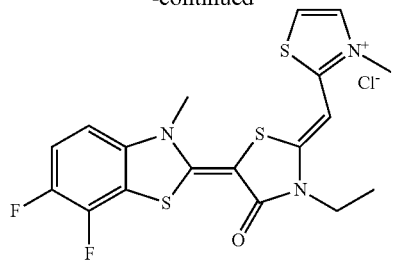
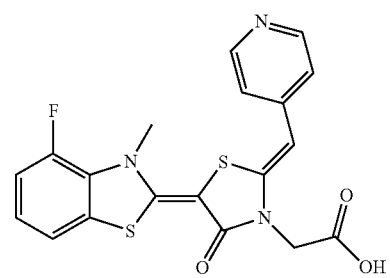
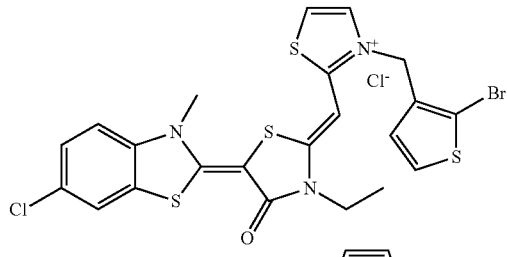
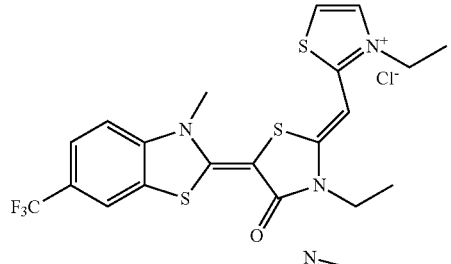
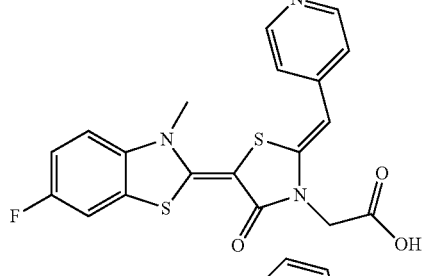
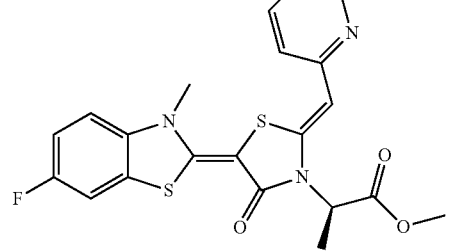

125
-continued
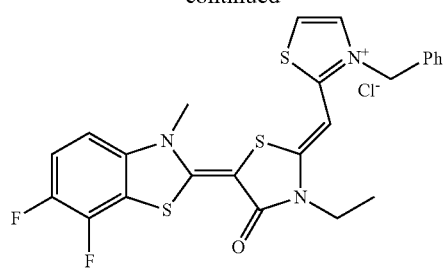
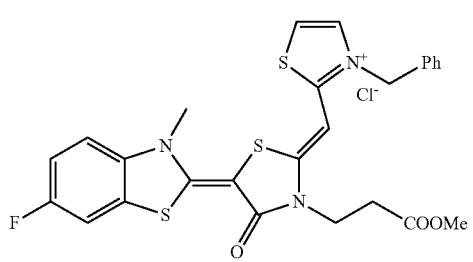
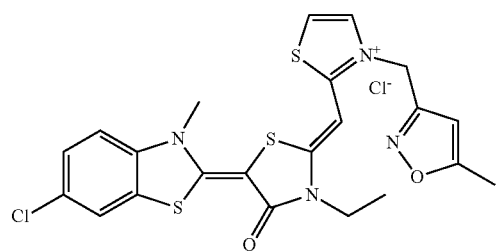
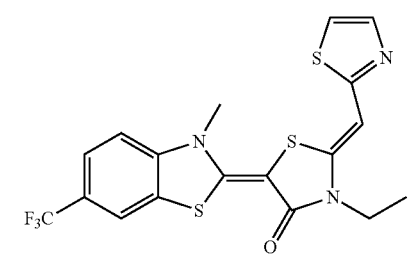
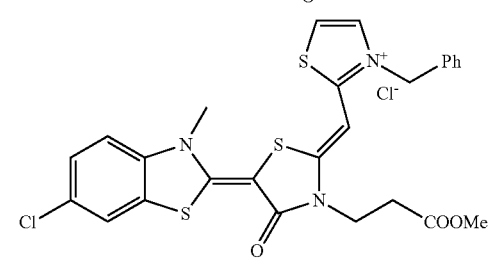
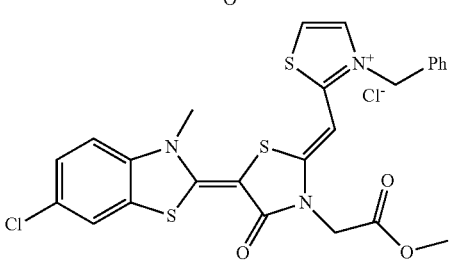
126
-continued
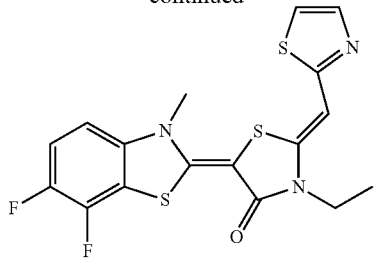
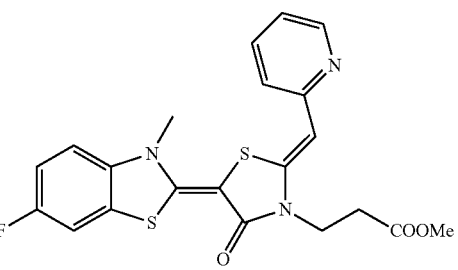
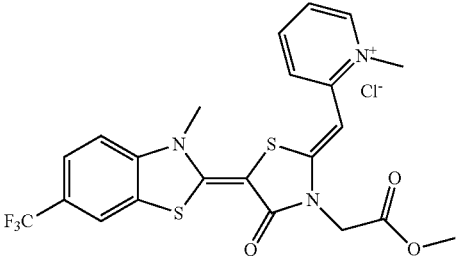
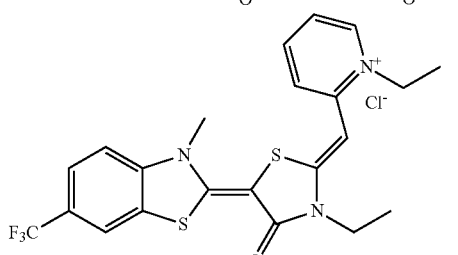
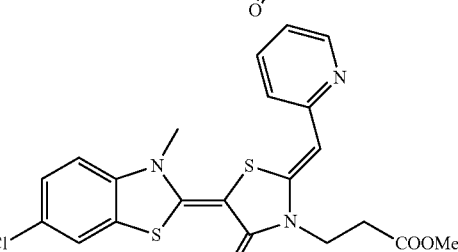
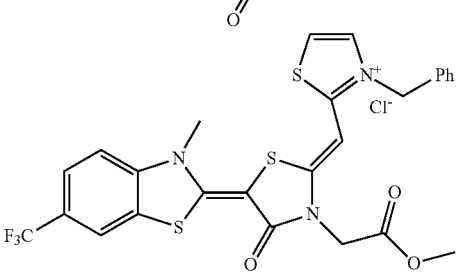

127
-continued
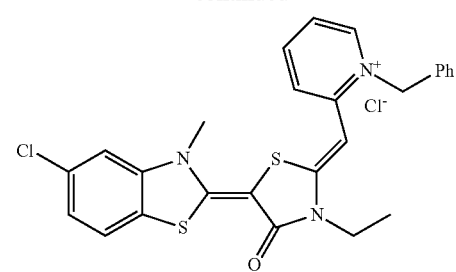
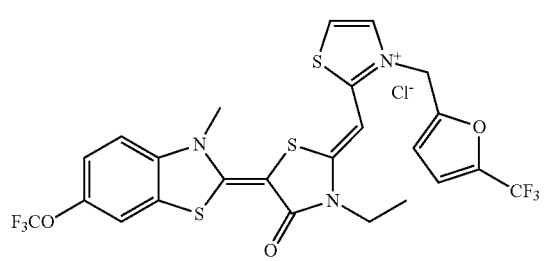
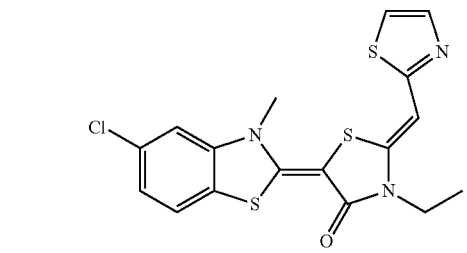
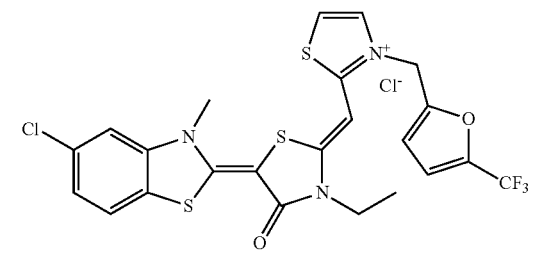
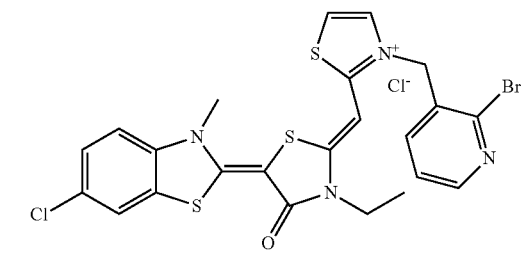
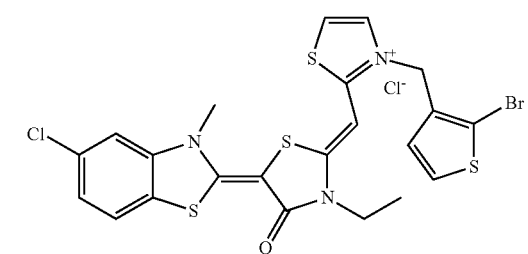
128
-continued
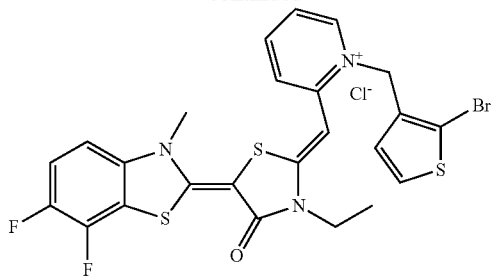
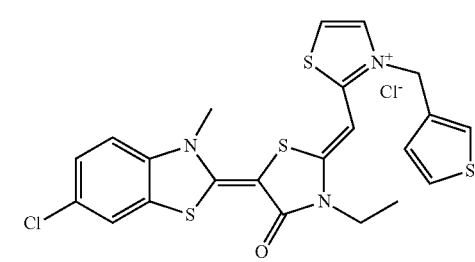
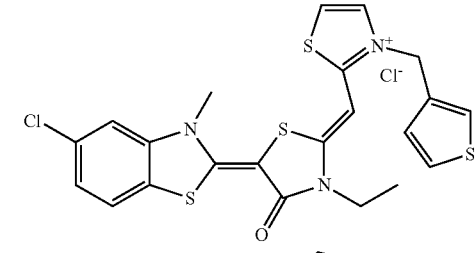
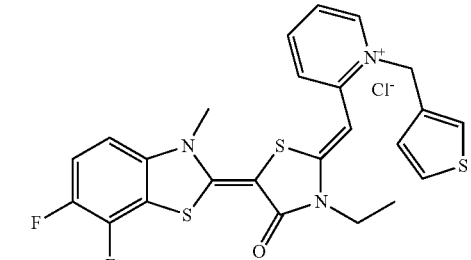
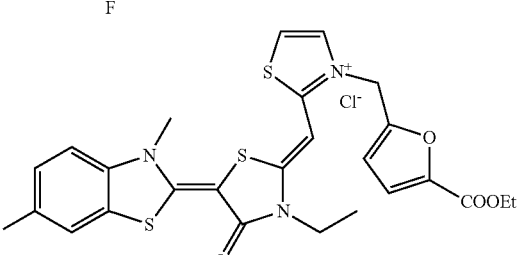
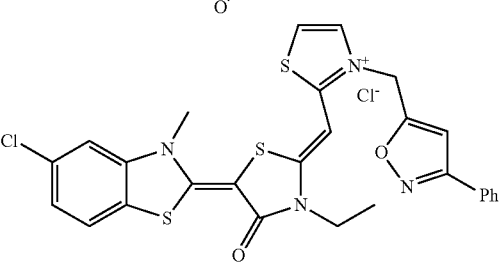

129
-continued
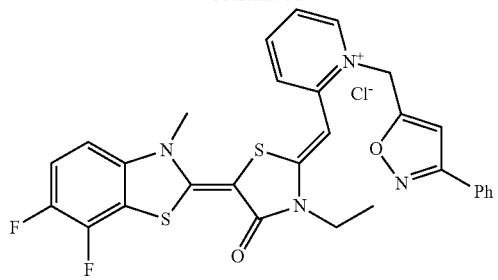
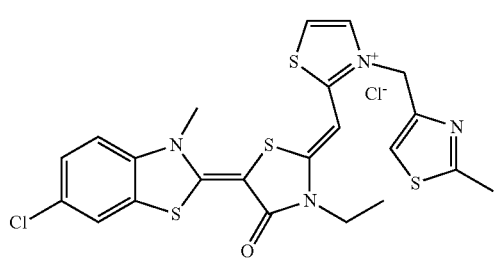
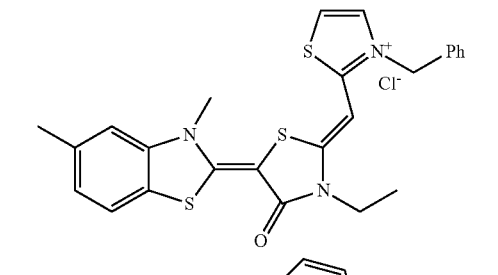
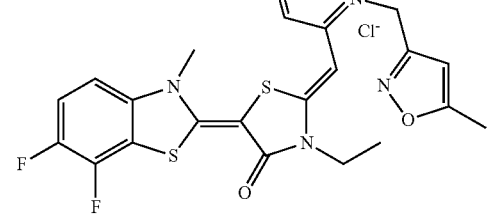
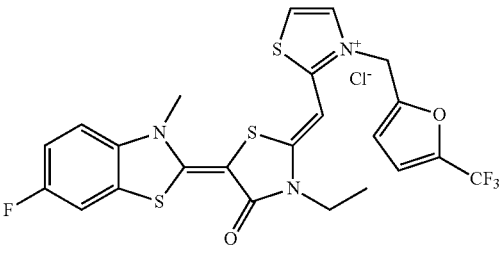
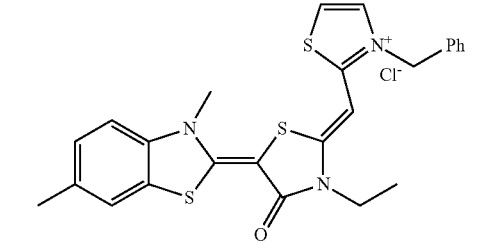
130
-continued
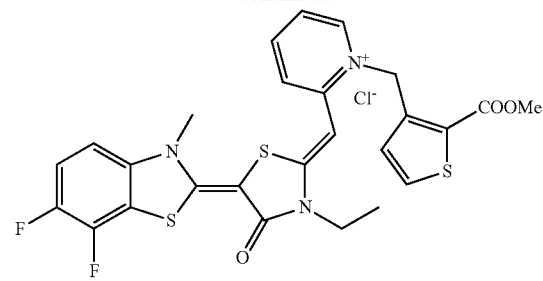
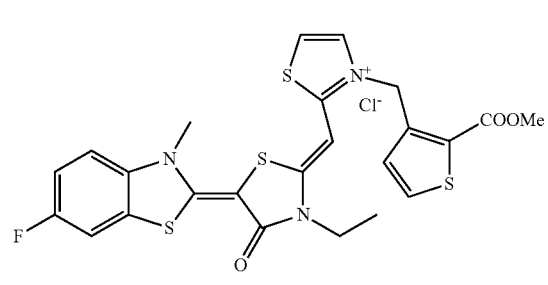
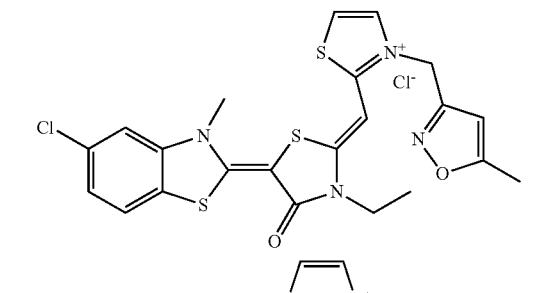
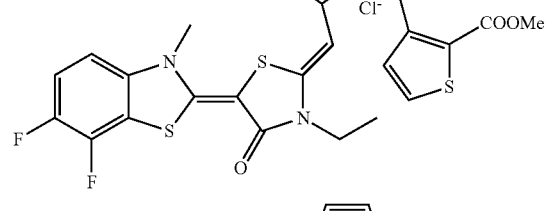
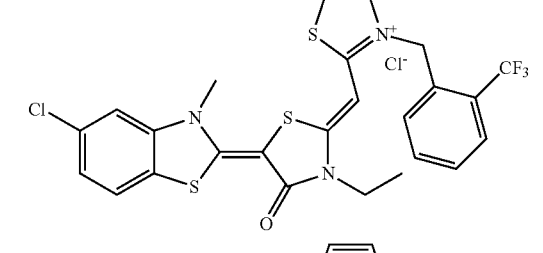
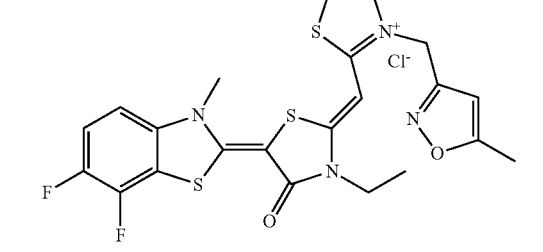

131
-continued
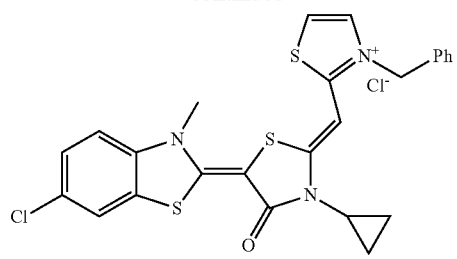
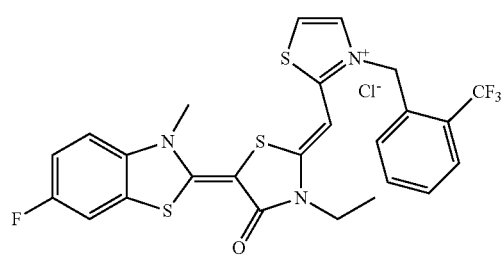
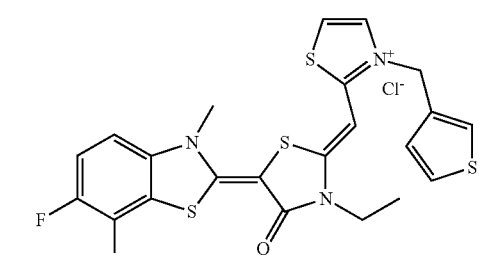
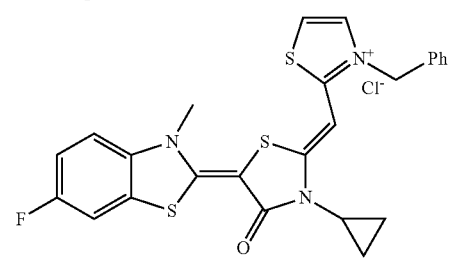
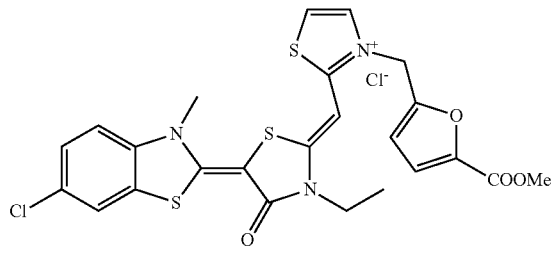
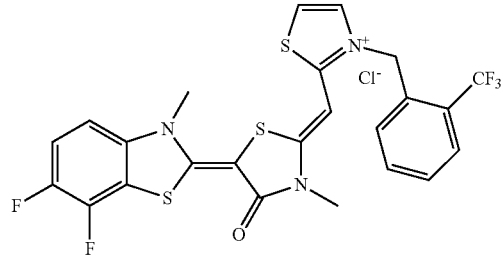
132
-continued
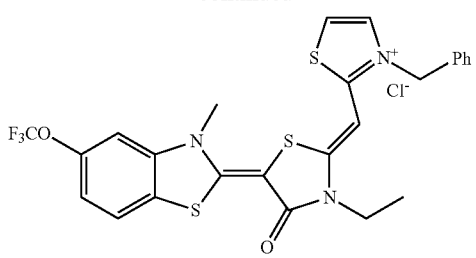
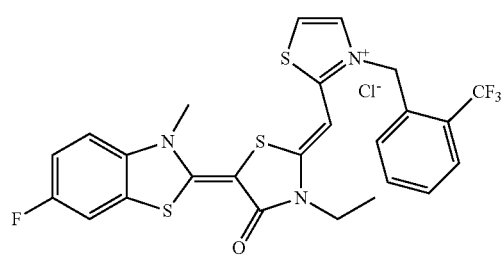
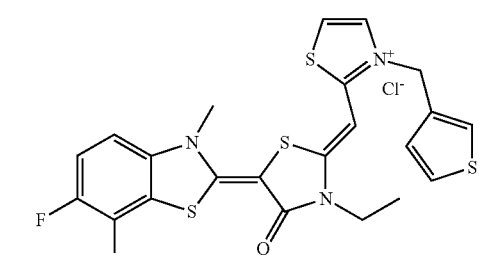
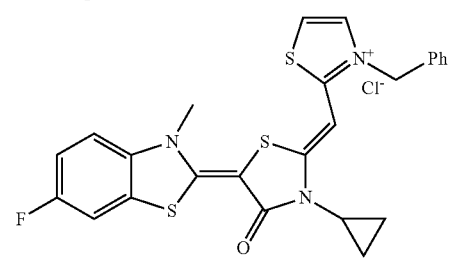
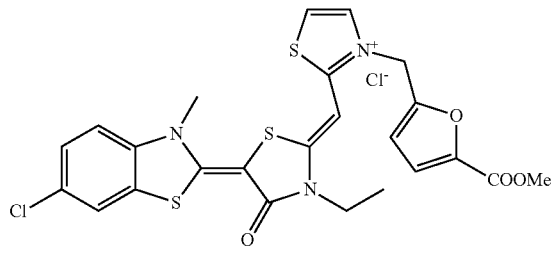
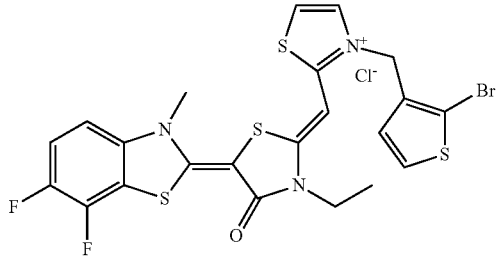

133
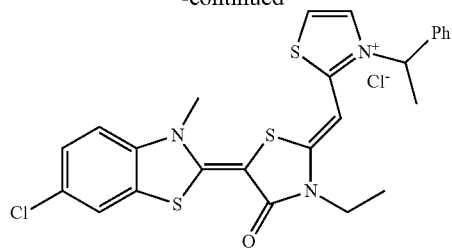
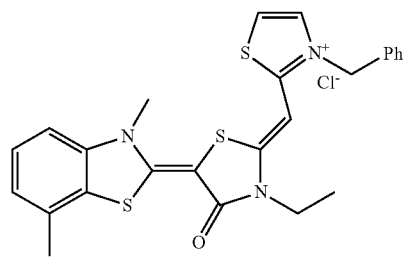
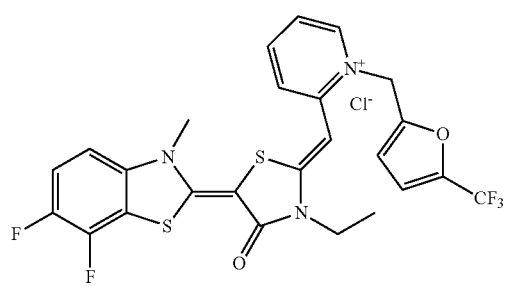
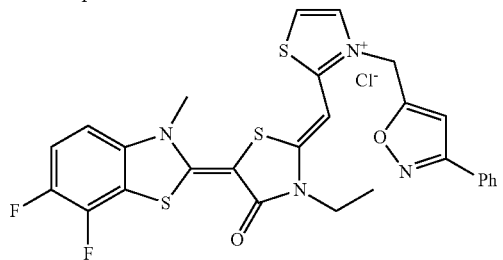
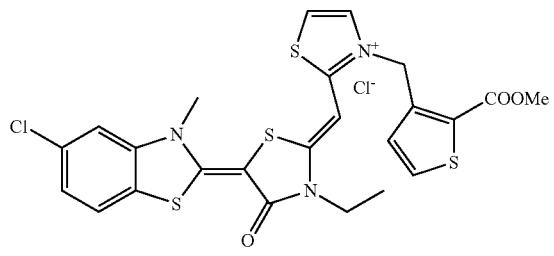
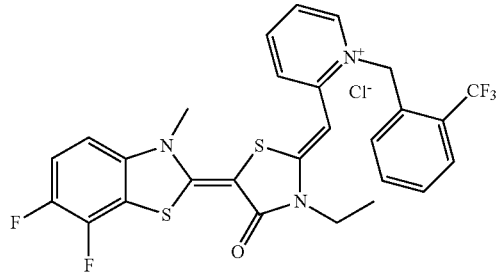
134
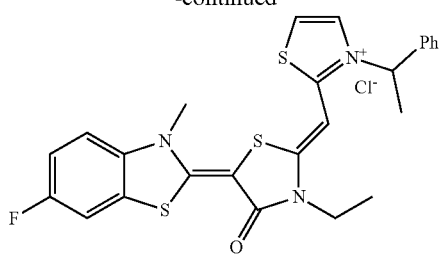
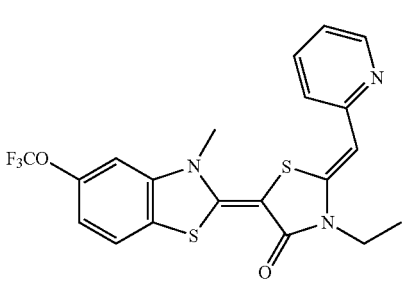
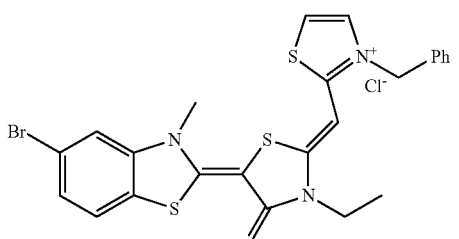
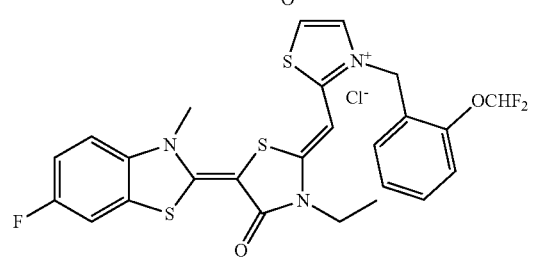
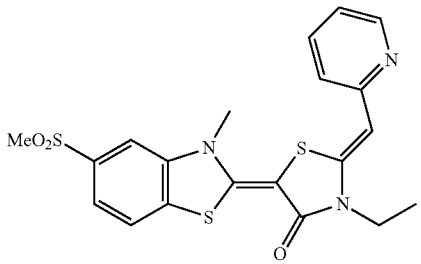
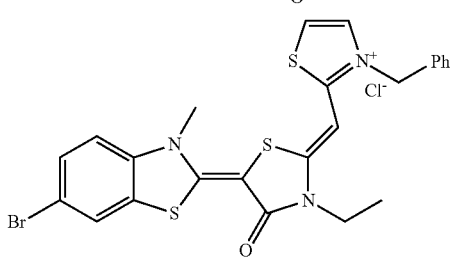

-continued
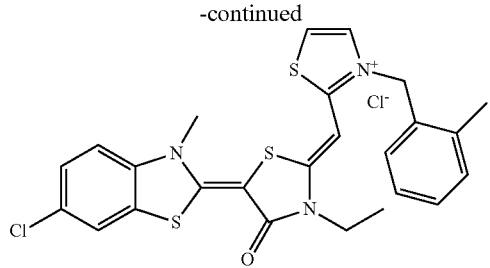
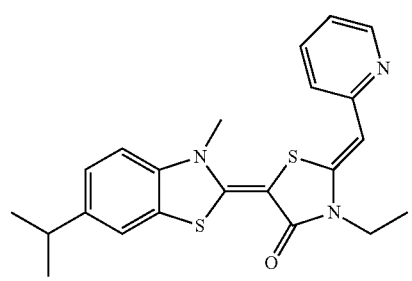
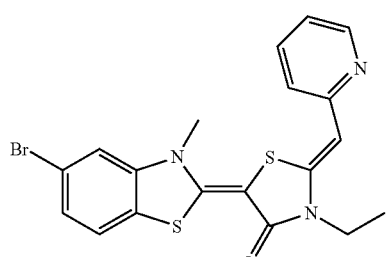
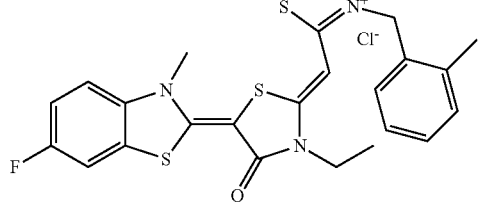
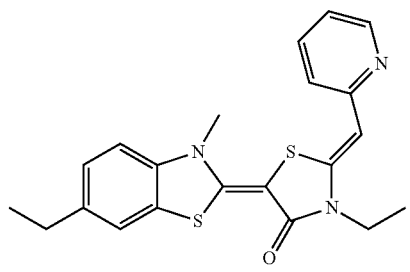
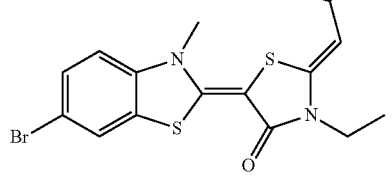
-continued
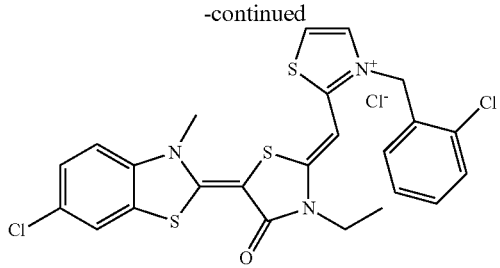
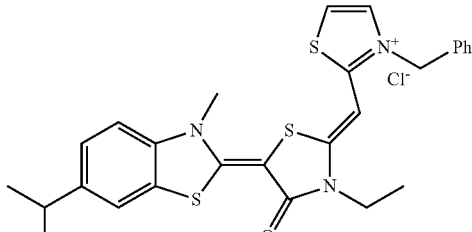
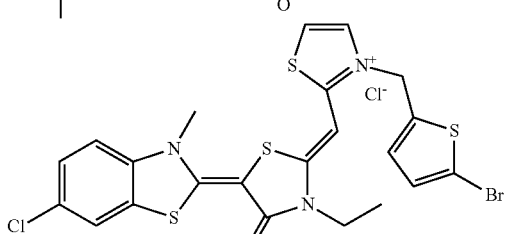
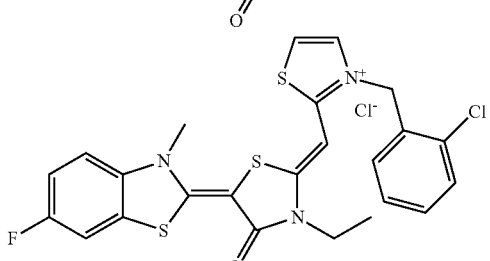
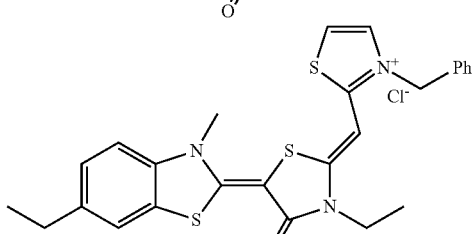
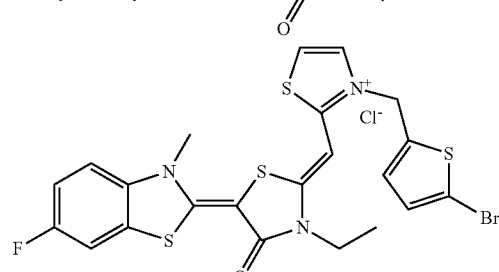
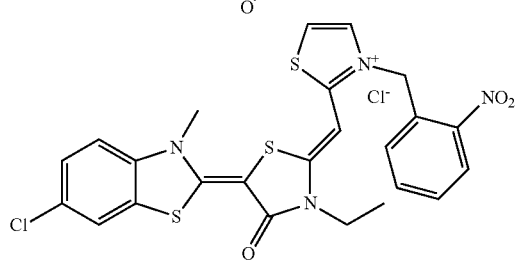

137
-continued
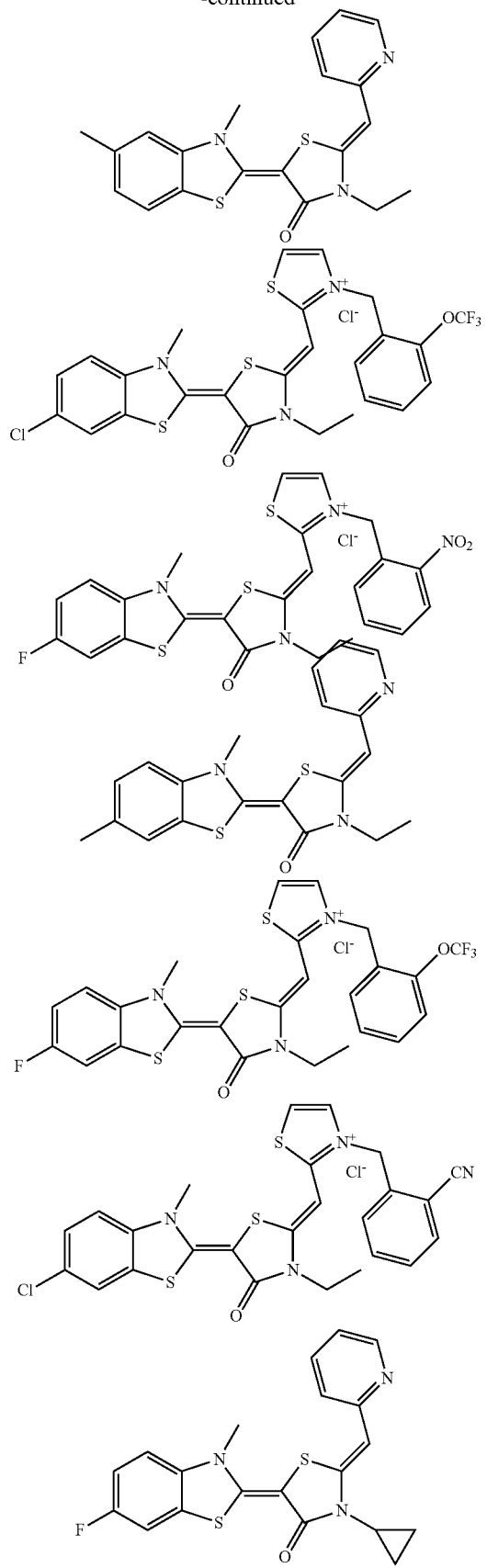
138
-continued
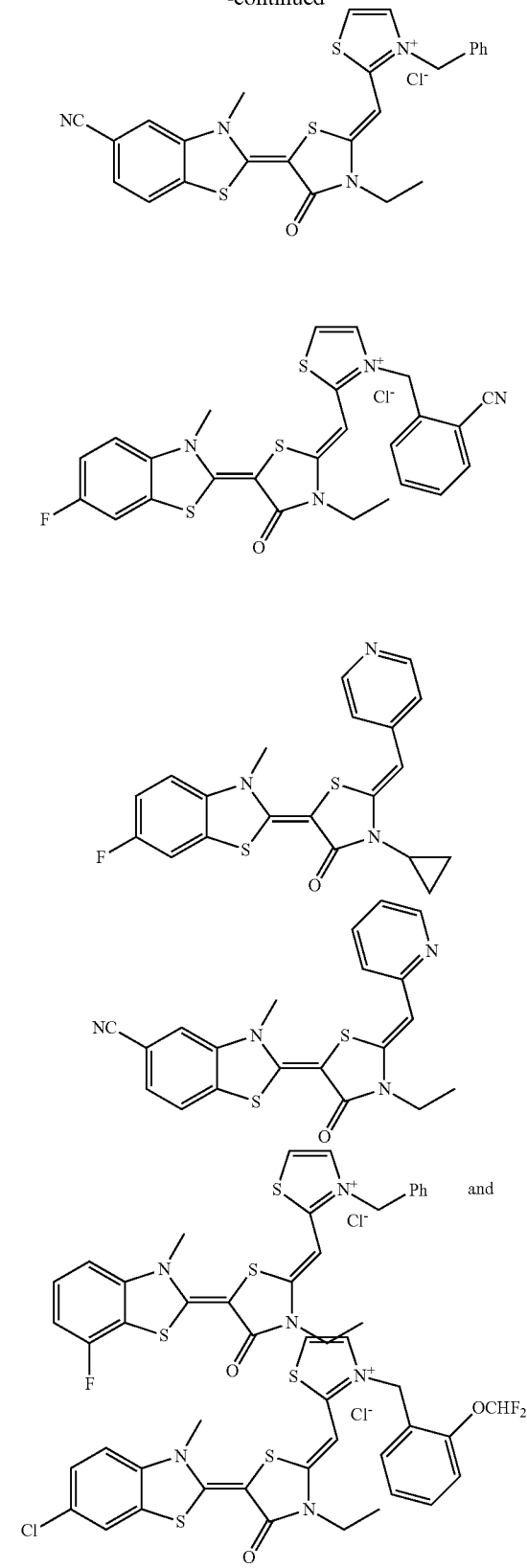
or a salt thereof.
* * * * *

UNITED STATES PATENT AND TRADEMARK OFFICE
CERTIFICATE OF CORRECTION

PATENT NO. : 9,642,843 B2
APPLICATION NO. : 14/770850
DATED : May 9, 2017
INVENTOR(S) : Jason E. Gestwicki et al.

Page 1 of 2

It is certified that error appears in the above-identified patent and that said Letters Patent is hereby corrected as shown below:

In the Claims

At Column 137, Lines 20-37, Claim 6 " 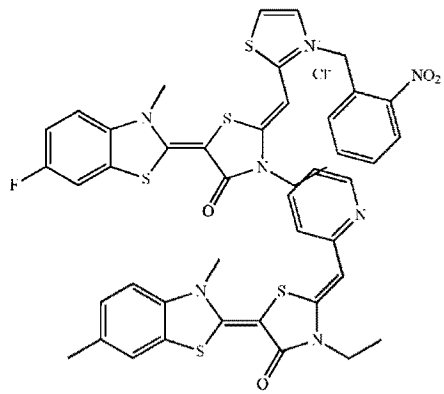 " should be

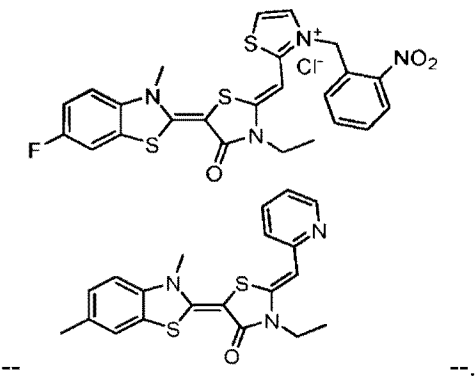

-- --.

Signed and Sealed this
Twentieth Day of November, 2018

Andrei Iancu
*Director of the United States Patent and Trademark Office*

CERTIFICATE OF CORRECTION (continued)
U.S. Pat. No. 9,642,843 B2

At Column 138, Lines 46-63, Claim 6 " 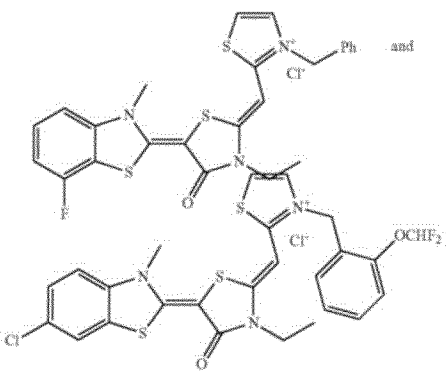 " should be

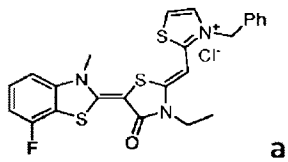 and

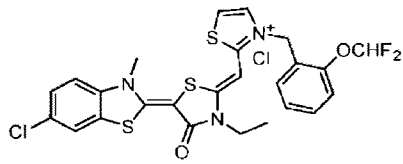 --.